(12) United States Patent
Kamath et al.

(10) Patent No.: US 11,389,090 B2
(45) Date of Patent: Jul. 19, 2022

(54) INTERMITTENT MONITORING

(71) Applicant: DexCom, Inc., San Diego, CA (US)

(72) Inventors: Apurv Ullas Kamath, San Diego, CA (US); Margaret A. Crawford, Encinitas, CA (US); John Michael Gray, San Diego, CA (US); Hari Hampapuram, San Diego, CA (US); Matthew Lawrence Johnson, Solana Beach, CA (US); Subrai Girish Pai, San Diego, CA (US); Shawn Clay Sanders, San Diego, CA (US); Sumitaka Mikami, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

(21) Appl. No.: 16/718,008

(22) Filed: Dec. 17, 2019

(65) Prior Publication Data

US 2020/0196923 A1 Jun. 25, 2020

Related U.S. Application Data

(63) Continuation of application No. 16/717,834, filed on Dec. 17, 2019.
(Continued)

(51) Int. Cl.
*G16H 10/60* (2018.01)
*G16H 40/67* (2018.01)
(Continued)

(52) U.S. Cl.
CPC .......... *A61B 5/14532* (2013.01); *A61B 5/002* (2013.01); *A61B 5/0022* (2013.01);
(Continued)

(58) Field of Classification Search
CPC ... A61B 5/14532; A61B 5/002; A61B 5/0022; A61B 5/1118; A61B 5/14546;
(Continued)

(56) References Cited

U.S. PATENT DOCUMENTS 3,014,603 A 12/1961 Taubmann
8,077,634 B2 12/2011 Maggenti et al.
(Continued)

FOREIGN PATENT DOCUMENTS

WO 2015017996 A1 2/2015
WO 2017011346 A1 1/2017

OTHER PUBLICATIONS

Extended European Search Report for Application No. 17776704.3 dated Oct. 18, 2019, 09 pages.
(Continued)

*Primary Examiner* — Patrick Fernandes
*Assistant Examiner* — Liam A Wallace
(74) *Attorney, Agent, or Firm* — FIG. 1 Patents

(57) ABSTRACT

Various examples are directed to systems and methods for monitoring a patient. For example, patient data of a first type may be monitored with a low-fidelity monitoring technique over a first time period. Patient behavior may be evaluated based on the monitored first type of patient data. Patient data of a second type may be monitored over a second time period with a continuous glucose monitor device. A parameter of the continuous glucose monitor device may be based on the evaluated patient behavior during the monitoring.

20 Claims, 37 Drawing Sheets

Related U.S. Application Data

(60) Provisional application No. 62/782,291, filed on Dec. 19, 2018.

(51) Int. Cl.

| | | |
|---|---|---|
| *A61B 5/1455* | (2006.01) | |
| *A61B 5/0205* | (2006.01) | |
| *G16H 20/17* | (2018.01) | |
| *A61B 5/145* | (2006.01) | |
| *A61B 5/00* | (2006.01) | |
| *A61B 5/11* | (2006.01) | |
| *A61M 5/172* | (2006.01) | |
| *G06F 11/10* | (2006.01) | |
| *A61B 5/024* | (2006.01) | |

(52) U.S. Cl.
CPC .......... *A61B 5/1118* (2013.01); *A61B 5/1455* (2013.01); *A61B 5/14546* (2013.01); *A61B 5/7267* (2013.01); *A61B 5/742* (2013.01); *A61B 5/7475* (2013.01); *A61M 5/1723* (2013.01); *G06F 11/1004* (2013.01); *G16H 10/60* (2018.01); *G16H 40/67* (2018.01); *A61B 5/0205* (2013.01); *A61B 5/02438* (2013.01); *A61B 2560/0209* (2013.01); *A61B 2560/0214* (2013.01); *G16H 20/17* (2018.01)

(58) Field of Classification Search
CPC ..... A61B 5/1455; A61B 5/7267; A61B 5/742; A61B 5/7475; A61B 5/0205; A61B 5/02438; A61B 2560/0209; A61B 2560/0214; A61M 5/1723; G16H 40/67; G16H 10/60; G16H 20/17; G06F 11/1004
See application file for complete search history.

(56) References Cited

U.S. PATENT DOCUMENTS

| | | | |
|---|---|---|---|
| 8,424,007 B1 | 4/2013 | Hernacki et al. | |
| 8,839,266 B1 | 9/2014 | Partridge et al. | |
| 10,596,318 B2 | 3/2020 | Morris et al. | |
| 2003/0012149 A1 | 1/2003 | Maggenti et al. | |
| 2005/0080526 A1 | 4/2005 | Williams et al. | |
| 2007/0047392 A1 | 3/2007 | Parkinson et al. | |
| 2007/0190991 A1 | 8/2007 | Cargille | |
| 2007/0240166 A1 | 10/2007 | Marappan | |
| 2008/0215883 A1 | 9/2008 | Fok et al. | |
| 2008/0309485 A1 | 12/2008 | Raduchel | |
| 2009/0318792 A1 | 12/2009 | Fennell et al. | |
| 2011/0025499 A1 | 2/2011 | Hoy et al. | |
| 2011/0119087 A1* | 5/2011 | Drucker ............. A61B 5/14532 705/3 |
| 2012/0165639 A1 | 6/2012 | Engelhardt et al. | |
| 2012/0232520 A1 | 9/2012 | Sloan et al. | |
| 2013/0035865 A1 | 2/2013 | Mayou et al. | |
| 2014/0068273 A1 | 3/2014 | Sobel et al. | |
| 2014/0068593 A1 | 3/2014 | McErlane et al. | |
| 2014/0095874 A1 | 4/2014 | Desai et al. | |
| 2014/0173625 A1 | 6/2014 | Kumar et al. | |
| 2014/0177839 A1 | 6/2014 | Wagner et al. | |
| 2014/0181842 A1 | 6/2014 | Kim et al. | |
| 2014/0184422 A1 | 6/2014 | Mensinger et al. | |
| 2014/0195639 A1 | 7/2014 | Kamen et al. | |
| 2014/0275852 A1* | 9/2014 | Hong .................. A61B 5/0205 600/301 |
| 2014/0325065 A1 | 10/2014 | Birtwhistle et al. | |
| 2014/0364711 A1 | 12/2014 | Ismail et al. | |
| 2015/0123813 A1 | 5/2015 | Hernandez-Rosas et al. | |
| 2015/0173674 A1 | 6/2015 | Hayes et al. | |
| 2015/0222637 A1 | 8/2015 | Hung et al. | |
| 2015/0282767 A1 | 10/2015 | Stivoric et al. | |
| 2015/0289823 A1* | 10/2015 | Rack-Gomer ....... A61B 5/7435 600/365 |
| 2015/0319143 A1 | 11/2015 | Kim et al. | |
| 2015/0335272 A1 | 11/2015 | Natale et al. | |
| 2016/0117520 A1 | 4/2016 | Safa | |
| 2016/0157733 A1 | 6/2016 | Gil | |
| 2016/0171871 A1 | 6/2016 | Zhang et al. | |
| 2016/0262707 A1 | 9/2016 | DeVries | |
| 2016/0335002 A1 | 11/2016 | Malkin | |
| 2017/0216524 A1 | 8/2017 | Haider et al. | |
| 2017/0286194 A1 | 10/2017 | Morris et al. | |
| 2017/0286614 A1 | 10/2017 | Morris et al. | |
| 2017/0329917 A1* | 11/2017 | McRaith ................ G16H 10/60 |
| 2017/0372017 A1 | 12/2017 | Steffen | |
| 2018/0137939 A1 | 5/2018 | Steiger | |
| 2018/0303417 A1 | 10/2018 | Mensinger et al. | |

OTHER PUBLICATIONS

International Preliminary Report on Patentability for Application No. PCT/US2017/025170 dated Oct. 11, 2018, 13 pages.

International Search Report and Written opinion for Application No. PCT/US2017/025170 dated Jul. 21, 2017, 14 pages.

Office Action for European Application No. 17776704.3, dated Sep. 10, 2020, 4 pages.

Office Action from Canadian Patent Application No. 3014603 dated Jul. 30, 2020, 4 pages.

International Search Report and Written Opinion dated Apr. 21, 2020 for Application No. PCT/US2019/66958, filed Dec. 17, 2019.

Office Action from Canadian Patent Application No. 3014603 dated Jul. 14, 2021, 5 pages.

Examination Report No. 1 for Australian Patent Application No. 2020204573, dated Aug. 26, 2021, 4 pages.

* cited by examiner

| State | Physiologic Condition | Treatment |
|---|---|---|
| Normal | None | None |
| Hyperinsulinaemia | Insulin resistance | Diet and exercise |
| Post-meal glycemia | Impaired glucose tolerance | Oral medication<br>Diet and exercise |
| Fasting hyperglycemia | Impaired fasting glucose | Insulin<br>Oral medication<br>Diet and exercise |
| Fasting hyperglycemia increased | Type 2 diabetes | Intermittent monitoring<br>Insulin<br>Oral medication<br>Diet and exercise |

FIG. 3

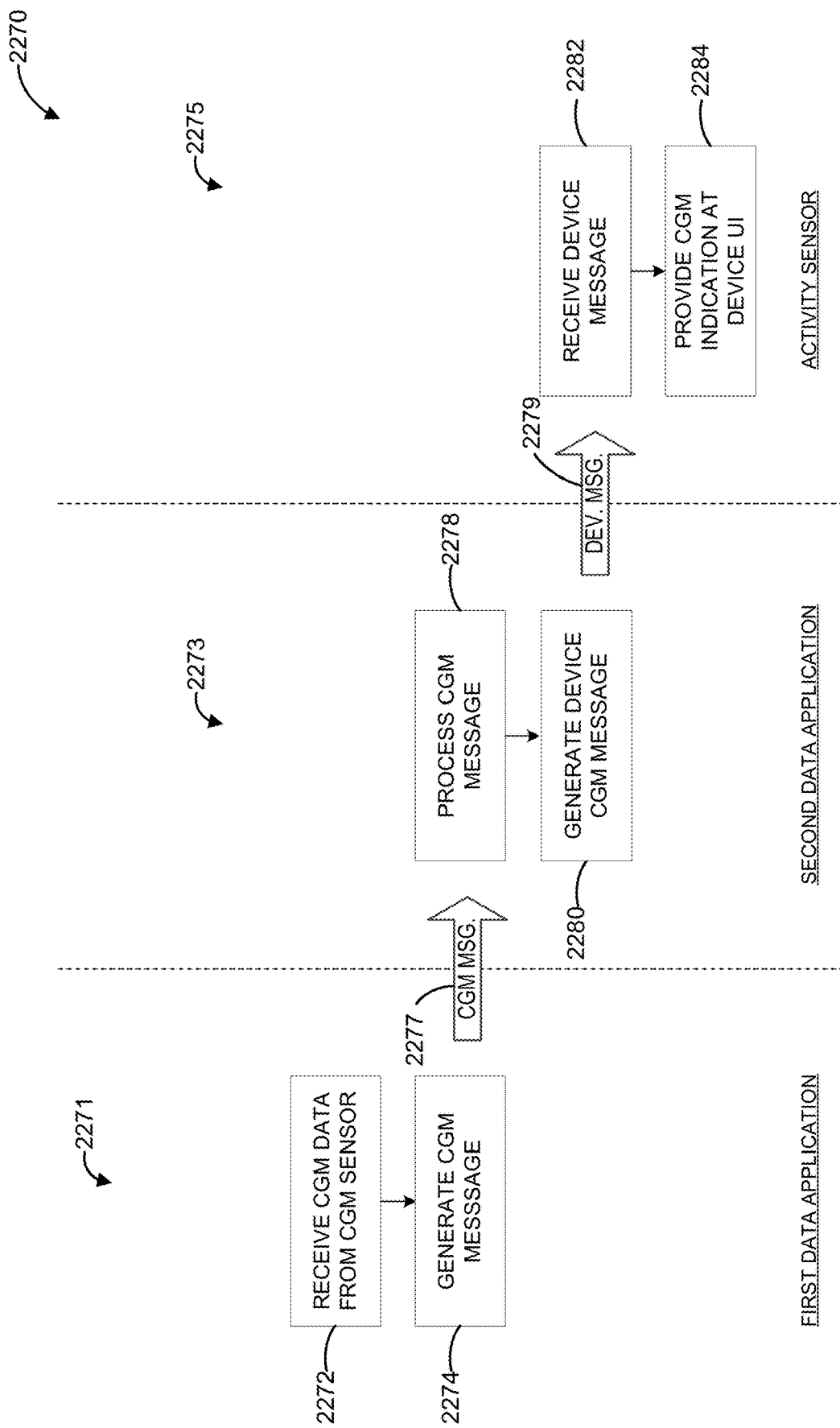

INTERMITTENT MONITORING

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/717,834, filed on Dec. 17, 2019, which claims the benefit of U.S. Provisional Patent Application Ser. No. 62/782,291, filed on Dec. 19, 2018. The aforementioned application is incorporated by reference herein in its entirety, and is hereby expressly made a part of this specification.

TECHNICAL FIELD

The present development relates generally to medical devices such as analyte sensors, and more particularly, but not by way of limitation, to systems, devices, and methods for intermittent use of continuous glucose monitoring systems or other monitoring systems.

BACKGROUND

Diabetes is a metabolic condition relating to the production or use of insulin by the body. Insulin is a hormone that allows the body to use glucose for energy, or store glucose as fat.

When a person eats a meal that contains carbohydrates, the food is processed by the digestive system, which produces glucose in the person's blood. Blood glucose can be used for energy or stored as fat. The body normally maintains blood glucose levels in a range that provides sufficient energy to support bodily functions and avoids problems that can arise when glucose levels are too high, or too low. Regulation of blood glucose levels depends on the production and use of insulin, which regulates the movement of blood glucose into cells.

When the body does not produce enough insulin, or when the body is unable to effectively use insulin that is present, blood sugar levels can elevate beyond normal ranges. The state of having a higher than normal blood sugar level is called "hyperglycemia." Chronic hyperglycemia can lead to several health problems, such as cardiovascular disease, cataract and other eye problems, nerve damage (neuropathy), and kidney damage. Hyperglycemia can also lead to acute problems, such as diabetic ketoacidosis—a state in which the body becomes excessively acidic due to the presence of blood glucose and ketones, which are produced when the body cannot use glucose. The state of having lower than normal blood glucose levels is called "hypoglycemia." Severe hypoglycemia can lead to acute crises that can result in seizures or death.

Diabetes conditions are sometimes referred to as "Type 1" and "Type 2." A Type 1 diabetes patient is typically able to use insulin when it is present, but the body is unable to produce sufficient amounts of insulin, because of a problem with the insulin-producing beta cells of the pancreas. A Type 2 diabetes patient may produce some insulin, but the patient has become "insulin resistant" due to a reduced sensitivity to insulin. The result is that even though insulin is present in the body, the insulin is not sufficiently used by the patient's body to effectively regulate blood sugar levels.

Blood sugar concentration levels may be monitored with an analyte sensor, such as a continuous glucose monitor. A continuous glucose monitor may provide the wearer (patient) with information such as an estimated blood glucose level or a trend of estimated blood glucose levels.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

This document discusses, among other things, systems, devices, and methods for battery management in an analyte sensor, such as a glucose sensor.

An example (e.g., "Example 1") of subject matter (e.g., a method, device or system) may include Example 1 is a method of monitoring a diabetic patient. The method may include receiving first data of a first type of a patient over a first time period. The method may also include receiving second data of a second type of the patient over at least a second time period. The first and second time periods may at least partially overlap for an overlapping time period. The method may include determining a correlation between the first and second data over the overlapping time period and, at a subsequent time, receiving data of the second type and determining diabetic information about the patient based at least in part on the data of the second type at the subsequent time and the determined correlation.

In Example 2, the subject matter of Example 1 optionally includes examples in which the first data includes high-fidelity continuous glucose monitoring data.

In Example 3, the subject matter of any one or more of Examples 1-2 optionally includes examples in which the second data includes single-point glucose monitoring, blinded CGM, data from a wearable monitor, flash glucose monitoring, or an optical monitoring technique.

In Example 4, the subject matter of Example 3 optionally includes examples in which the second data includes single-point glucose monitoring. The method may further comprise calculating a time window to take a single-point glucose measurement based on the first data.

In Example 5, the subject matter of any one or more of Examples 1-4 optionally includes examples in which the diabetic information is selected from the group consisting of: an estimated value for data of the first type at the subsequent time, a state of the patient, or a patient insight.

In Example 6, the subject matter of Example 5 optionally includes examples in which the state of the patient or the patient insight is related to a lifestyle modification relating to diet, exercise, glucose level monitoring, or medication.

In Example 7, the subject matter of Example 6 optionally includes examples in which the state of the patient or the patient insight is related to mealtime management, exercise management, or sleep management.

In Example 8, the subject matter of any one or more of Examples 1-7 optionally includes examples in which the first data is high-fidelity data and the second data is low-fidelity data.

In Example 9, the subject matter of any one or more of Examples 1-8 optionally include receiving a sensor signal from a sensor and processing the sensor signal to generate at least a portion of the second data.

In Example 10, the subject matter of Example 9 optionally includes examples in which the sensing includes activity monitoring by a wearable fitness tracker.

In Example 11, the subject matter of Example 10 optionally includes examples in which the wearable fitness tracker includes a wearable heart rate monitor, a wearable activity monitor, a smart phone, smart glasses, or a smart watch.

In Example 12, the subject matter of any one or more of Examples 1-11 optionally include examples in which determining a correlation includes determining a relation between the obtained first and the second data at corresponding times of day and/or days of a week within the overlapping time period.

In Example 13, the subject matter of any one or more of Examples 1-12 optionally include examples in which the second data includes user input data.

In Example 14, the subject matter of Example 13 optionally includes examples in which the user input data includes medicament data, meal data, exercise data, sleep data, or any combination thereof.

In Example 15, the subject matter of any one or more of Examples 1-14 optionally includes intermittently monitoring the first type of data and determining diabetic information using the second data and the correlation during a period when the first type of data is not available.

In Example 16, the subject matter of Example 15 optionally includes examples in which the intermittently monitoring the first type of data includes intermittent continuous glucose monitoring, and the monitoring data of the second type includes monitoring activity data with a wearable accelerometer, and optionally includes examples in which the wearable accelerometer is configured to at least monitor data when the continuous glucose monitoring is not occurring.

In Example 17, the subject matter of any one or more of Examples 1-16 optionally includes examples in which the first data of a first type includes an estimated glucose concentration level and the data of the second type includes heart rate, oxygen concentration, skin tone, moisture content on skin, activity, activity patterns, blood ketones, urine ketones, respiration, or acoustic information.

In Example 18, the subject matter of any one or more of Examples 1-17 optionally includes monitoring the first data and the second data over a third time period, and updating the correlation based on the first data and second data from the third time period.

In Example 19, the subject matter of any one or more of Examples 1-18 optionally includes administering a treatment based at least in part on the determined diabetic information.

In Example 20, the subject matter of Example 19 optionally includes examples in which the treatment includes a pharmaceutical intervention.

In Example 21, the subject matter of any one or more of Examples 19-20 optionally includes displaying diabetic information about the patient on a user interface of a patient device.

In Example 22, the subject matter of Example 21 optionally includes displaying a recommended dietary modification or lifestyle modification on the user interface.

Example 23 is a method that may include receiving an estimated glucose concentration level of a patient from a continuous glucose monitoring (CGM) system for a first time period and receiving non-CGM information relating to the patient for the first time period. The method may also include determining a relationship between the estimated glucose concentration level and the non-CGM information. The method may also include receiving non-CGM information relating to the patient for a second time period for which estimated glucose concentration levels are not available from the CGM and determining diabetic information about the patient for the second time period based upon the determined relationship and the non-CGM information. The method may further include electronically delivering a notification about the diabetic information.

In Example 24, the subject matter of Example 23 optionally includes examples in which the non-CGM information includes activity information.

In Example 25, the subject matter of any one or more of Examples 23-24 optionally includes examples in which the non-CGM information includes physiologic information about the patient.

In Example 26, the subject matter of Example 25 optionally includes examples in which the physiologic information includes one or more of heart rate, respiration, oxygen concentration, skin tone, moisture content on the skin, activity, activity patterns, blood ketones, urine ketones, respiration, or acoustic information.

In Example 27, the subject matter of any one or more of Examples 23-26 optionally includes examples in which the non-CGM information includes location information.

In Example 28, the subject matter of any one or more of Examples 23-27 optionally includes examples in which receiving non-CGM information includes receiving user input data.

In Example 29, the subject matter of any one or more of Examples 23-28 optionally includes examples in which determining diabetic information about the patient includes determining a patient state.

In Example 30, the subject matter of any one or more of Examples 23-29 optionally includes examples in which determining a patient state includes applying the non-CGM information to a model.

In Example 31, the subject matter of any one or more of Examples 23-30 optionally includes examples in which determining diabetic information includes determining an estimated glucose concentration level.

In Example 32, the subject matter of any one or more of Examples 23-31 optionally includes examples in which determining diabetic information includes determining a qualitative rating.

In Example 33, the subject matter of any one or more of Examples 23-32 optionally includes examples in which determining diabetic information includes determining a quantitative metric.

In Example 34, the subject matter of Example 33 optionally includes examples in which the quantitative metric is an estimate of an amount or percentage of time that a glucose concentration level was in range during a specified time period.

Example 35 is a system comprising an intermittent primary subsystem configured to intermittently collect primary physiologic information from a host and a secondary subsystem configured to collect secondary data of a second type from a host. The system may also include a user interface configured to display guidance that is based upon the secondary data and the primary physiologic information.

In Example 36, the subject matter of Example 35 optionally includes a guidance system configured to receive the secondary data and the primary physiologic information and determine the guidance based at least in part on the secondary data and the primary physiologic information.

In Example 37, the subject matter of Example 36 optionally includes examples in which the guidance system determines a relationship between the secondary data and the primary physiologic information, and during time periods when the intermittent primary physiologic information is not available the guidance system determines the guidance based at least in part on the secondary data and the relationship between the secondary data and the primary physiologic information.

In Example 38, the subject matter of Example 37 optionally includes examples in which the primary subsystem includes a continuous glucose monitor (CGM) and the guidance system determines diabetes management information based at least in part on the secondary data and the relationship between the secondary data and the primary physiologic information.

In Example 39, the subject matter of Example 38 optionally includes examples in which the diabetes management information includes an estimated glucose concentration level.

In Example 40, the subject matter of any one or more of Examples 38-39 optionally includes examples in which the diabetes management information includes a qualitative rating.

In Example 41, the subject matter of any one or more of Examples 38-40 optionally include examples in which the diabetes management information includes a metric.

In Example 42, the subject matter of Example 41 optionally includes examples in which the diabetes management information includes a time-in-range metric that indicates an estimate of an amount or percentage of time that a glucose concentration level was in range during a specified time period.

In Example 43, the subject matter of any one or more of Examples 41-42 optionally includes examples in which the diabetes management information includes statistical feedback.

In Example 44, the subject matter of any one or more of Examples 35-43 optionally includes examples in which the secondary subsystem includes a sensor and a memory circuit, and the secondary subsystem determines the secondary data from data received from the sensor and stores the received sensor data or the secondary data in the memory circuit.

In Example 45, the subject matter of any one or more of Examples 35-44 optionally includes examples in which the primary subsystem includes a continuous glucose monitor (CGM), a memory circuit, and the primary subsystem receives a CGM sensor signal indicative of a glucose concentration in a host, determines an estimated glucose concentration level based at least in part on the CGM sensor signal, and stores a plurality of estimated glucose concentration levels in the memory circuit, and in which the primary physiologic information includes or is based on the plurality of estimated glucose concentration levels.

Example 46 is a patient-management device, comprising a sensor; a user interface; a communication circuit; and a processor. The processor may execute instructions to perform operations. The operations may comprise transmitting information based on input from the sensor to a second device using the communication circuit and receiving, using the communication circuit, an estimate of a physiologic state based at least in part on the input from the sensor. The operations may also include delivering information relating the estimate of the physiologic state using the user interface.

In Example 47, the subject matter of Example 46 optionally includes examples in which the sensor is an activity sensor.

In Example 48, the subject matter of any one or more of Examples 46-47 optionally includes examples in which the estimate of a physiologic state is a glucose concentration level.

In Example 49, the subject matter of any one or more of Examples 46-48 optionally includes examples in which the information about the estimate of the physiologic state is a time-in-range, a glucose concentration level, or a glucose concentration range.

In Example 50, the subject matter of any one or more of Examples 46-49 optionally includes examples in which the estimate of the physiologic state is based upon a correlation between previously-collected glucose concentration information and previously-collected activity information.

In Example 51, the subject matter of any one or more of Examples 46-50 optionally includes examples in which the device is wearable.

In Example 52, the subject matter of Example 51 optionally includes examples in which the device is a watch.

In Example 53, the subject matter of any one or more of Examples 46-52 optionally include examples in which the operations further comprise: generating, by a first application executed by the processor, a sensor message comprising the estimate of the physiologic state and sending, by the first application, the sensor message to a second application executed by the processor; and sending, by the second application, a device message to the second device for display using the user interface.

In Example 54, the subject matter of Example 53 optionally includes examples in which generating the sensor message comprises encrypting the estimate of the physiologic state.

In Example 55, the subject matter of any one or more of Examples 53-54 optionally includes examples in which generating the sensor message comprises generating an error detection code based at least in part on the physiologic state.

Example 56 is a method of monitoring a patient. The method may comprise monitoring patient data of a first type with a low-fidelity monitoring technique over a first time period and evaluating patient engagement or behavior based on the monitored first type of patient data The method may also include monitoring over a second time period patient data of a second type with a high-fidelity monitoring technique using a monitoring device. In some examples, at least one hardware or software functionality of the monitoring device is based on the evaluated patient engagement or behavior during the monitoring.

In Example 57, the subject matter of Example 56 optionally includes examples in which the at least one hardware or software functionality corresponds to operation of a user interface.

In Example 58, the subject matter of any one or more of Examples 56-57 optionally includes examples in which the high-fidelity monitoring technique is continuous glucose monitoring.

In Example 59, the subject matter of any one or more of Examples 56-58 optionally includes examples in which the low-fidelity technique includes: single-point glucose monitoring or blinded CGM or an optical monitoring technique.

In Example 60, the subject matter of any one or more of Examples 56-59 optionally includes examples in which the low-fidelity monitoring technique includes activity monitoring by a wearable fitness tracker.

In Example 61, the subject matter of Example 60 optionally includes examples in which the wearable fitness tracker is a wearable heart rate monitor, activity monitor, smart phone, smart glasses, or smart watch.

In Example 62, the subject matter of any one or more of Examples 56-61 optionally includes examples in which the low-fidelity monitoring technique includes receiving user input data.

In Example 63, the subject matter of Example 62 optionally includes examples in which the received user input data includes medicament data, meal data, exercise data, sleep data, or any combination thereof.

In Example 64, the subject matter of any one or more of Examples 56-63 optionally includes determining for the patient a goal, and wherein the at least one hardware or software functionality of the monitoring device is related to the goal.

In Example 65, the subject matter of Example 64 optionally includes examples in which the goal includes a dietary goal, an exercise goal, a glucose level monitoring goal, or a medication goal.

In Example 66, the subject matter of Example 65 optionally includes examples in which the at least one hardware or software functionality of the monitoring device relates to mealtime glucose management.

In Example 67, the subject matter of any one or more of Examples 65-66 optionally includes examples in which the at least one hardware or software functionality of the monitoring device relates to sleep management.

In Example 68, the subject matter of any one or more of Examples 64-67 optionally includes examples in which the determining for the patient a goal is determined prior to the monitoring over a first time.

In Example 69, the subject matter of any one or more of Examples 64-68 optionally includes examples in which the determining for the patient a goal is determined by the data of a first type monitored over the first time period with the low-fidelity monitoring technique.

In Example 70, the subject matter of any one or more of Examples 56-69 optionally includes monitoring over the first time period patient data of a physiological type, and wherein the basing of the at least one hardware or software functionality of the monitoring device is further based on the patient data of the physiological type.

In Example 71, the subject matter of any one or more of Examples 56-70 optionally includes examples in which the at least one hardware or software functionality relates to frequency or content of an automated coaching routine.

In Example 72, the subject matter of any one or more of Examples 56-71 optionally includes detecting a change in a patient parameter, the change measured as between the first time period and the second time period and using the detected change to further influence at least one hardware or software functionality of the monitoring device.

In Example 73, the subject matter of any one or more of Examples 56-72 optionally includes over the first time period, providing a coaching functionality to the patient, the coaching functionality comprising automated messages transmitted from a server to the monitoring device based on patient profile data or the patient data of the first type or a combination thereof.

In Example 74, the subject matter of any one or more of Examples 56-73 optionally includes after the second time period, determining an amount or frequency of subsequent data, the amount or frequency of subsequent data being determined with the low-fidelity monitoring technique or the high-fidelity monitoring technique, the amount or frequency calculated to increase or maximize a patient parameter.

In Example 75, the subject matter of Example 74 optionally includes examples in which the patient parameter is time-in-range.

In Example 76, the subject matter of Example 75 optionally includes examples in which the amount or frequency of subsequent data is determined with the low-fidelity monitoring technique.

In Example 77, the subject matter of Example 76 optionally includes examples in which the amount or frequency of subsequent data is represented by a number of sensors.

In Example 78, the subject matter of any one or more of Examples 74-77 optionally examples in which the patient parameter is A1c.

In Example 79, the subject matter of Example 78 optionally includes examples in which the amount or frequency of subsequent data is determined with the low-fidelity monitoring technique.

In Example 80, the subject matter of any one or more of Examples 74-79 optionally include displaying on the monitoring device an indication of the increased or maximized patient parameter.

In Example 81, the subject matter of any one or more of Examples 74-80 optionally include after the second time period, determining a patient end goal, the patient end goal at least in part dependent on the patient data of the first type or the patient data of the second type, and displaying a therapy recommendation calculated to cause a transition of a patient state towards the patient end goal.

Example 82 is a system comprising a first system configured to collect a first set of sensor data of a first type relating to a patient and a second system configured to collect a second set of sensor data of a second type of data relating to the patient. The system may further comprise a decision system configured to determine a user parameter for the second system based upon the first set of sensor data.

In Example 83, the subject matter of Example 82 optionally includes examples in which first system includes an activity sensor.

In Example 84, the subject matter of any one or more of Examples 82-83 optionally includes examples in which first system includes a blood glucose meter.

In Example 85, the subject matter of any one or more of Examples 82-84 optionally includes examples in which the second system includes a continuous glucose monitor.

In Example 86, the subject matter of any one or more of Examples 82-85 optionally includes examples in which the user parameter includes a schedule for use of the second system.

In Example 87, the subject matter of any one or more of Examples 82-86 optionally includes examples in which the user parameter is a time to initiate us of the second system.

In Example 88, the subject matter of any one or more of Examples 82-87 optionally includes examples in which the decision system applies the first set of sensor data to a model.

In Example 89, the subject matter of any one or more of Examples 82-88 optionally includes a third system configured to collect a third set of sensor data relating to the patient, wherein the decision system determines the user parameter based at least in part on the first set of sensor data and the third set of data.

Example 90 is a patient-management device. The patient-management device may comprise a sensor, a user interface, a communication circuit, and a processor. The processor may execute instructions to receive, using the communication circuit, information about a subject and deliver, using the user interface, information relating the management of a physiologic condition based upon the received information about the subject and data from the sensor.

In Example 91, the subject matter of Example 90 optionally includes examples in which the sensor is an activity sensor.

In Example 92, the subject matter of any one or more of Examples 90-91 optionally include examples in which the device is wearable device.

In Example 93, the subject matter of Example 92 optionally includes examples in which the device is a watch.

In Example 94, the subject matter of any one or more of Examples 90-93 optionally includes examples in which the processor is further executing instructions to determine a configuration for the user interface using the information about the subject.

In Example 95, the subject matter of Example 94 optionally includes examples in which the device displays a specified set of metrics based upon previously-collected low-fidelity data.

In Example 96, the subject matter of any one or more of Examples 94-95 optionally includes examples in which the device delivers information at a specified time based upon previously-collected low-fidelity data.

In Example 97, the subject matter of any one or more of Examples 94-96 optionally includes examples in which the device informs a patient management facilitator regarding an availability of an estimate of a physiologic state and presents guidance from the patient management facilitator using the user interface.

In Example 98, the subject matter of any one or more of Examples 90-97 optionally includes examples in which the estimate of a physiologic state is a glucose concentration level.

Example 99 is a method for selecting patients who are likely to benefit from intermittent high-fidelity monitoring. The method may comprise performing a first screening algorithm on a pool of participants to determine a group of patients with diabetes or with diabetic risk factors. The method may also include providing a first kit to a participant in the determined group, the kit structured and configured to enable the participant to perform low-fidelity monitoring of their health for a first duration with a first monitoring technique and obtaining first results. The method may include performing a second screening algorithm on the determined group to determine a cohort for participation in intermittent high-fidelity monitoring, the second screening algorithm using at least in part the obtained first results and subsequently providing a second kit to participants in the determined cohort, the second kit structured and configured to enable a participant of the determined cohort to perform high-fidelity monitoring of their health for a second duration with a second monitoring technique and obtaining second results. The method may also include providing a third kit to one or more participants in the determined cohort, the one or more participants determined according to, at least in part, the obtained second results.

In Example 100, the subject matter of Example 99 optionally includes examples in which the high-fidelity monitoring is continuous glucose monitoring.

In Example 101, the subject matter of any one or more of Examples 99-100 optionally includes examples in which performing the second screening includes determining an estimated likelihood that the patient will benefit from the high-fidelity monitoring.

In Example 102, the subject matter of any one or more of Examples 99-101 optionally includes examples in which the second kit is structured and configured based on the obtained first results.

In Example 103, the subject matter of any one or more of Examples 99-102 optionally includes examples in which the third kit is structured and configured based on the obtained second results.

In Example 104, the subject matter of any one or more of Examples 99-103 optionally include performing communications between a server and a device in the first kit during at least the first duration, the communications providing a guidance message to the patient.

In Example 105, the subject matter of any one or more of Examples 99-104 optionally includes examples in which the low-fidelity monitoring includes: single-point glucose monitoring, heart rate monitoring, activity monitoring, blinded continuous glucose monitoring, or any combination thereof.

In Example 106, the subject matter of any one or more of Examples 99-105 optionally include displaying an output to the patient, the displayed output relating to diet, exercise, glucose level monitoring, or medication.

In Example 107, the subject matter of any one or more of Examples 99-106 optionally include displaying an output to the patient, the displayed output indicating an optimized duration of time for which the patient should employ high-fidelity monitoring.

In Example 108, the subject matter of any one or more of Examples 99-107 optionally include examples in which the algorithm employs one or more factors selected from the group consisting of electronic health records, type II diabetes diagnosis codes, family history, weight, BMI, history of metabolic diseases, blood test results, A1c, fasting glucose levels, oral glucose tolerance, prescribed diabetes medications, or any combination thereof.

In Example 109, the subject matter of any one or more of Examples 99-108 optionally includes examples in which the second screening algorithm is based at least in part on a factor of adherence to use of the low-fidelity monitoring during the first duration.

Example 110 is a method of managing a parameter related to patient health, the method including a phase of intermittent high-fidelity monitoring. The method may comprise, first, monitoring a patient for a first duration with a first monitoring technique and obtaining first results. The method may also comprise monitoring the patient for a second duration with a second monitoring technique and obtaining second results. The method may also comprise determining an action that the patient may perform, the action based on the obtained first and second results, the action calculated to increase a likelihood of satisfaction of a management condition. In some examples, either the first monitoring technique or the second monitoring technique includes high-fidelity monitoring.

In Example 111, the subject matter of Example 110 optionally includes examples in which the high-fidelity monitoring includes continuous glucose monitoring.

In Example 112, the subject matter of any one or more of Examples 110-111 optionally includes displaying an output to the patient, the displayed output indicating patient performance in relation to a dietary goal, an exercise goal, a glucose level monitoring goal, or a medication goal.

In Example 113, the subject matter of any one or more of Examples 110-112 optionally includes examples in which the parameter related to patient health is selected from the group consisting of: time-in-range and glycemic variability.

In Example 114, the subject matter of any one or more of Examples 110-113 optionally includes examples in which the satisfaction of the management condition comprises decreasing the parameter related to patient health by greater than a predetermined amount with a confidence greater than a predetermined confidence level.

In Example 115, the subject matter of any one or more of Examples 110-114 optionally includes selecting a patient. In some examples, selecting the patient is performed by determining a patient from a pool of patients likely to benefit from intermittent high-fidelity monitoring, the likelihood greater than a calculated value.

In Example 116, the subject matter of any one or more of Examples 110-115 optionally includes examples in which the first duration is a subset of the second duration.

In Example 117, the subject matter of any one or more of Examples 110-116 optionally includes examples in which the first duration overlaps the second duration.

In Example 118, the subject matter of any one or more of Examples 110-117 optionally includes performing communications between a server and a device associated with the patient during the first duration or the second duration or both, the communications providing a coaching functionality to the patient.

In Example 119, the subject matter of any one or more of Examples 110-118 optionally includes displaying an output to the patient, the displayed output indicating an optimized duration of time for which the patient should employ high-fidelity monitoring.

In Example 120, the subject matter of any one or more of Examples 110-119 optionally includes examples in which the first monitoring technique is a low-fidelity monitoring technique and the second monitoring technique is the high-fidelity monitoring.

In Example 121, the subject matter of Example 120 optionally includes examples in which the low-fidelity monitoring technique includes: single-point glucose monitoring or blinded CGM.

In Example 122, the subject matter of any one or more of Examples 120-121 optionally includes examples in which the low-fidelity monitoring technique includes activity monitoring by a wearable fitness tracker.

In Example 123, the subject matter of Example 122 optionally includes examples in which the wearable fitness tracker is a wearable heart rate monitor, activity monitor, smart phone, smart glasses, or smart watch.

In Example 124, the subject matter of any one or more of Examples 120-123 optionally includes correlating the obtained first and second results, the correlating including determining a relation between the obtained first and second results at corresponding times of day and/or days of a week, and determining an estimated value for a high-fidelity monitoring technique at a given time based at least in part on a correlated value for the given time and a result obtained by the low-fidelity monitoring technique.

In Example 125, the subject matter of Example 124 optionally includes determining the estimated value based at least in part on population data.

In Example 126, the subject matter of any one or more of Examples 120-125 optionally includes examples in which the low-fidelity monitoring technique includes receiving user input data.

In Example 127, the subject matter of Example 126 optionally includes examples in which the received user input data includes medicament data, meal data, exercise data, sleep data, or any combination thereof.

In Example 128, the subject matter of any one or more of Examples 120-127 optionally includes correlating the obtained first and second results, the correlating including determining a relation between the obtained first and second results at corresponding times of day or days of a week, and determining an estimated value for a high-fidelity monitoring technique at a given time based at least in part on the estimation of a correlated value for the given time and a result obtained by the low-fidelity monitoring technique.

In Example 129, the subject matter of Example 128 optionally includes determining the estimated value based at least in part on population data.

Example 130 is a method for measuring a parameter related to patient health. The method may comprise detecting, by an analyte sensor system, that the analyte sensor system has been applied to a host. The method may also comprise storing, by the analyte sensor system, analyte data describing the host; determining, by the analyte sensor system, that sensor use at the analyte sensor system has terminated and uploading, by the analyte sensor system, stored analyte data to an upload computing device.

In Example 131, the subject matter of Example 130 optionally includes, responsive to determining that the sensor use at the analyte sensor system has terminated, broadcasting, by the analyte sensor system, system identification data; receiving, by the analyte sensor system and from the upload computing device, a communication request comprising the system identification data, and establishing, by the analyte sensor system, a communication session with the upload computing device responsive to the communication request, wherein the uploading transmitting the stored analyte data to the upload computing device.

In Example 132, the subject matter of any one or more of Examples 130-131 optionally includes after determining that the sensor use at the analyte sensor system has terminated, receiving, by the analyte sensor system, an upload request from the upload computing device and broadcasting, by the analyte sensor system, system identification data; receiving, from the upload computing device, authentication data. The method may also include establishing, by the analyte sensor system, a communication session with the upload computing device, wherein the uploading transmitting the stored analyte data to the upload computing device.

Example 133 is a method comprising: receiving an estimated glucose concentration level of a patient from a continuous glucose monitoring (CGM) system for a first time period; receiving non-glucose information relating to the patient for the first time period; determining a relationship between the estimated glucose concentration level and the non-glucose information; receiving non-glucose information relating to the patient for a second time period; determining diabetic information about the patient for the second time period based upon the determined relationship and the non-glucose information; and electronically delivering a notification about the diabetic information.

In Example 134, the subject matter of Example 133 optionally includes receiving a plurality of estimated glucose concentration levels from the first time period from the CGM system, and wherein receiving the non-glucose information for the first time period comprises receiving at least one single-point glucose measurement taken during the first time period.

In Example 135, the subject matter of any one or more of Examples 133-134 optionally includes wherein estimated glucose concentration levels are not available from the CGM during the second time period.

In Example 136, the subject matter of any one or more of Examples 133-135 optionally includes receiving second non-glucose information related to the patient for the first time period, wherein the second non-glucose information is different than the non-glucose information, and wherein the relationship is between the estimated glucose concentration level, the non-glucose information, and the second non-glucose information.

In Example 137, the subject matter of any one or more of Examples 133-136 optionally includes wherein the non-glucose information includes physiologic information about the patient.

In Example 138, the subject matter of Example 137 optionally includes wherein the physiologic information includes at least one of heart rate, respiration, oxygen concentration, skin tone, moisture content on the skin, activity, activity patterns, blood ketones, urine ketones, respiration, or acoustic information.

In Example 139, the subject matter of any one or more of Examples 133-138 optionally includes wherein the non-glucose information includes location information.

In Example 140, the subject matter of any one or more of Examples 133-139 optionally includes wherein determining diabetic information includes determining an estimated glucose concentration level.

In Example 141, the subject matter of any one or more of Examples 133-140 optionally includes wherein determining diabetic information includes determining an estimate of an amount or percentage of time that a glucose concentration level was in range during a specified time period.

Example 142 is a system comprising: a primary subsystem configured to intermittently collect primary physiologic information from a host; a secondary subsystem configured to collect secondary data of a second type from a host; a guidance system configured to determine guidance based at least in part on the primary physiologic information and the secondary data; and a user interface configured to display the guidance.

In Example 143, the subject matter of Example 142 optionally includes wherein the guidance system is also configured to: determine a relationship between the secondary data and the primary physiologic information; and determine the guidance during a time period in when primary physiologic information is not collected, wherein determining the guidance is based at least in part on the secondary data and the relationship between the secondary data and the primary physiologic information.

In Example 144, the subject matter of any one or more of Examples 142-143 optionally includes wherein the primary subsystem includes a continuous glucose monitor (CGM) and wherein the guidance system is further configured to determine a patient state based at least in part on the secondary data and a relationship between the secondary data and the primary physiologic information.

In Example 145, the subject matter of Example 144 optionally includes wherein the patient state comprises an estimated glucose concentration level.

In Example 146, the subject matter of any one or more of Examples 144-145 optionally includes wherein the patient state comprises a time in range metric that indicates an estimate of an amount or percentage of time that a glucose concentration level was in range during a specified time period.

In Example 147, the subject matter of any one or more of Examples 142-146 optionally includes wherein the secondary subsystem includes a sensor and a memory circuit, and wherein the secondary subsystem is further configured to: determine the secondary data from sensor data received from the sensor; and store the sensor data or the secondary data in the memory circuit.

In Example 148, the subject matter of any one or more of Examples 142-147 optionally includes wherein the primary subsystem includes a continuous glucose monitor (CGM), and a memory circuit, and wherein the primary subsystem is configured to: receive a CGM sensor signal indicative of a glucose concentration in a host; determine an estimated glucose concentration level based at least in part on the CGM sensor signal; and store a plurality of estimated glucose concentration levels in the memory circuit, wherein the primary physiologic information includes or is based on the plurality of estimated glucose concentration levels.

Example 149 is a computer-readable medium comprising instructions thereon that, when executed by at least one processor, causes the at least one processor to perform operations comprising: receiving an estimated glucose concentration level of a patient from a continuous glucose monitoring (CGM) system for a first time period; receiving non-glucose information relating to the patient for the first time period; determining a relationship between the estimated glucose concentration level and the non-glucose information; receiving non-glucose information relating to the patient for a second time period; determining diabetic information about the patient for the second time period based upon the determined relationship and the non-glucose information; and electronically delivering a notification about the diabetic information.

In Example 150, the subject matter of Example 149 optionally includes wherein the operations further comprise receiving a plurality of estimated glucose concentration levels from the first time period from the CGM system, and wherein receiving the non-glucose information for the first time period comprises receiving at least one single-point glucose measurement taken during the first time period.

In Example 151, the subject matter of any one or more of Examples 149-150 optionally includes the operations further comprising: determining guidance based at least in part on the diabetic information; and displaying the guidance at a user interface.

In Example 152, the subject matter of any one or more of Examples 149-151 optionally includes receiving second non-glucose information related to the patient for the first time period, wherein the second non-glucose information is different than the non-glucose information, and wherein the relationship is between the estimated glucose concentration level, the non-glucose information, and the second non-glucose information.

Example 153 is a patient-management system, comprising: an analyte sensor; and a processor executing instructions to perform operations comprising: receiving, by a first application executing at the processor and from the analyte sensor, sensor data indicating an analyte concentration of a user; transmitting, by the first application and to a second application executing at the processor, a sensor message comprising an indication of the analyte concentration; and delivering, by the second application and to a wearable activity monitor device, a device message, the device message based at least in part on the analyte concentration.

In Example 154, the subject matter of Example 153 optionally includes the wearable activity monitor device, wherein the wearable activity monitor device comprises a motion sensor, and wherein the wearable activity monitor device is programmed to generate a user interface including data based at least in part on the device message and data based at least in part on an output of the motion sensor.

In Example 155, the subject matter of any one or more of Examples 153-154 optionally includes wherein the operations further comprise generating physiologic state data describing an estimate of a physiologic state of the user, the generating based at least in part on the analyte concentration of the user.

In Example 156, the subject matter of Example 155 optionally includes wherein the physiologic state data is generated by the first application, and wherein the sensor message comprises the physiologic state data.

In Example 157, the subject matter of any one or more of Examples 155-156 optionally includes wherein the physiologic state data is generated by the second application, and wherein the device message comprises the physiologic state data.

In Example 158, the subject matter of any one or more of Examples 155-157 optionally includes wherein the physiologic state data comprises a time-in-range, a glucose concentration level, or a glucose concentration range.

In Example 159, the subject matter of any one or more of Examples 155-158 optionally includes wherein the generating of the physiologic state data is based upon a correlation between previously-collected glucose concentration information and previously-collected activity information.

In Example 160, the subject matter of any one or more of Examples 153-159 optionally includes wherein the device message comprises display data for display at a user interface of the wearable activity monitor device.

In Example 161, the subject matter of any one or more of Examples 153-160 optionally includes wherein generating the sensor message comprises encrypting the indication of the analyte concentration.

In Example 162, the subject matter of any one or more of Examples 153-161 optionally includes wherein generating the sensor message comprises generating an error detection code based at least in part on the analyte concentration.

Example 163 is a patient-management method, comprising: receiving, by a first application executing at a patient-management system and from an analyte sensor, sensor data indicating an analyte concentration of a user; transmitting, by the first application and to a second application executing at the patient-management system, a sensor message comprising an indication of the analyte concentration; and delivering, by the second application and to a wearable activity monitor device, a device message, the device message based at least in part on the analyte concentration.

In Example 164, the subject matter of Example 163 optionally includes wherein the wearable activity monitor device comprises a motion sensor, further comprising generating, by the wearable activity monitor device, a user interface including data based at least in part on the device message and data based at least in part on an output of the motion sensor.

In Example 165, the subject matter of any one or more of Examples 163-164 optionally includes generating physiologic state data describing an estimate of a physiologic state of the user, the generating based at least in part on the analyte concentration of the user.

In Example 166, the subject matter of Example 165 optionally includes wherein the physiologic state data is generated by the first application, and wherein the sensor message comprises the physiologic state data.

In Example 167, the subject matter of any one or more of Examples 165-166 optionally includes wherein the physiologic state data is generated by the second application, and wherein the device message comprises the physiologic state data.

In Example 168, the subject matter of any one or more of Examples 165-167 optionally includes wherein the physiologic state data comprises a time-in-range, a glucose concentration level, or a glucose concentration range.

In Example 169, the subject matter of any one or more of Examples 165-168 optionally includes wherein the generating of the physiologic state data is based upon a correlation between previously-collected glucose concentration information and previously-collected activity information.

In Example 170, the subject matter of any one or more of Examples 163-169 optionally includes wherein the device message comprises display data for display at a user interface of the wearable activity monitor device.

In Example 171, the subject matter of any one or more of Examples 163-170 optionally includes wherein generating the sensor message comprises generating an error detection code based at least in part on the analyte concentration.

Example 172 is a machine-readable medium comprising instructions thereon that, when executed by at least one processor, cause the at least one processor to perform operations comprising: receiving, by a first application executing at a patient-management system and from an analyte sensor, sensor data indicating an analyte concentration of a user; transmitting, by the first application and to a second application executing at the patient-management system, a sensor message comprising an indication of the analyte concentration; and delivering, by the second application and to a wearable activity monitor device, a device message, the device message based at least in part on the analyte concentration.

Example 173 is a method of monitoring a patient, comprising: monitoring patient data of a first type with a low-fidelity monitoring technique over a first time period; evaluating patient behavior based on the monitored first type of patient data; and monitoring over a second time period patient data of a second type with a continuous glucose monitor device, wherein a parameter of the continuous glucose monitor device is based on the evaluated patient behavior during the monitoring.

In Example 174, the subject matter of Example 173 optionally includes wherein the parameter of the continuous glucose monitor device corresponds to operation of a user interface.

In Example 175, the subject matter of any one or more of Examples 173-174 optionally includes wherein the low-fidelity monitoring technique comprises at least one of single point glucose monitoring, blinded continuous glucose monitoring, or an optical monitoring technique.

In Example 176, the subject matter of any one or more of Examples 173-175 optionally includes wherein the low-fidelity monitoring technique comprises activity monitoring by a wearable fitness tracker.

In Example 177, the subject matter of Example 176 optionally includes wherein the wearable fitness tracker comprises at least one of a wearable heart rate monitor, activity monitor, smart phone, smart glasses, or smart watch.

In Example 178, the subject matter of any one or more of Examples 173-177 optionally includes wherein the low-fidelity monitoring technique comprises receiving user input data comprising at least one of medicament data, meal data, exercise data, or sleep data.

In Example 179, the subject matter of any one or more of Examples 173-178 optionally includes determining a goal for the patient, and wherein the parameter of the continuous glucose monitor device is related to the goal.

In Example 180, the subject matter of Example 179 optionally includes wherein the goal includes a dietary goal, an exercise goal, a glucose level monitoring goal, or a medication goal.

In Example 181, the subject matter of any one or more of Examples 179-180 optionally includes wherein the determining the goal for the patient is based at least in part on the data of the first type monitored over the first time period with the low-fidelity monitoring technique.

In Example 182, the subject matter of any one or more of Examples 173-181 optionally includes determining the parameter of the continuous glucose monitor device at least in part by determining at least one parameter for an automated coaching routine.

In Example 183, the subject matter of any one or more of Examples 173-182 optionally includes detecting a change in a patient parameter between the first time period and the second time period; and determining the parameter of the continuous glucose monitor device using the detected change in the patient parameter.

In Example 184, the subject matter of any one or more of Examples 173-183 optionally includes providing a coaching functionality to the patient over the first time period, the coaching functionality comprising automated messages transmitted from a server to the continuous glucose monitor device, wherein the coaching functionality is based on patient profile data or the patient data of the first type or a combination thereof.

Example 185 is a system comprising: a low-fidelity system configured to collect a first set of sensor data of a first type relating to a patient over a first time period; a continuous glucose monitor device configured to collect a second set of sensor data of a second type of data relating to the patient; and a decision system configured to determine a parameter for the continuous glucose monitor device based upon the first set of sensor data.

In Example 186, the subject matter of Example 185 optionally includes wherein low-fidelity system includes an activity sensor.

In Example 187, the subject matter of any one or more of Examples 185-186 optionally includes wherein low-fidelity system includes a blood glucose meter.

In Example 188, the subject matter of any one or more of Examples 185-187 optionally includes wherein the continuous glucose monitor device includes a continuous glucose monitor.

In Example 189, the subject matter of any one or more of Examples 185-188 optionally includes wherein the parameter includes a schedule for use of the continuous glucose monitor device.

In Example 190, the subject matter of any one or more of Examples 185-189 optionally includes wherein the parameter is a time to initiate us of the continuous glucose monitor device.

In Example 191, the subject matter of any one or more of Examples 185-190 optionally includes a third system configured to collect a third set of sensor data relating to the patient, wherein the decision system determines the parameter based at least in part on the first set of sensor data and the third set of sensor data.

Example 192 is a machine-readable medium comprising instructions thereon that, when executed by at least one processor, cause the at least one processor to perform operations comprising: monitoring patient data of a first type with a low-fidelity monitoring technique over a first time period; evaluating patient behavior based on the monitored first type of patient data; and monitoring over a second time period patient data of a second type with a continuous glucose monitor device, wherein a parameter of the continuous glucose monitor device is based on the evaluated patient behavior during the monitoring.

Example 193 is a method for measuring a parameter related to patient health, the method comprising: detecting, by an analyte sensor system, that the analyte sensor system has been applied to a host; storing, by the analyte sensor system, analyte data describing the host; determining, by the analyte sensor system, that sensor use at the analyte sensor system has terminated; and uploading, by the analyte sensor system, stored analyte data to an upload computing device.

In Example 194, the subject matter of Example 193 optionally includes after determining that the sensor use at the analyte sensor system has terminated, broadcasting, by the analyte sensor system, system identification data; receiving, by the analyte sensor system and from the upload computing device, a communication request comprising the system identification data; and establishing, by the analyte sensor system, a communication session with the upload computing device responsive to the communication request, wherein the uploading is performed using the communication session.

In Example 195, the subject matter of any one or more of Examples 193-194 optionally includes after determining that the sensor use at the analyte sensor system has terminated, receiving, by the analyte sensor system, an upload request from the upload computing device; and receiving, from the upload computing device, authentication data.

In Example 196, the subject matter of any one or more of Examples 193-195 optionally includes after determining that the sensor use at the analyte sensor system has terminated, receiving, by the analyte sensor system, an upload request from the upload computing device; broadcasting, by the analyte sensor system, system identification data; receiving, from the upload computing device, authentication data; and establishing, by the analyte sensor system, a communication session with the upload computing device, wherein the uploading transmitting the stored analyte data to the upload computing device.

In Example 197, the subject matter of any one or more of Examples 193-196 optionally includes wherein detecting that the analyte sensor system has been applied to a host comprises determining that the analyte sensor system has provided sensor readings above a threshold value.

In Example 198, the subject matter of any one or more of Examples 193-197 optionally includes wherein detecting that the analyte sensor system has been applied to a host comprises determining that the analyte sensor system has provided sensor readings above a threshold value for more than a threshold time.

In Example 199, the subject matter of any one or more of Examples 193-198 optionally includes wherein determining that sensor use at the analyte sensor system has terminated comprises determining that more than a threshold time has elapsed since the analyte sensor system was applied to the host.

In Example 200, the subject matter of any one or more of Examples 193-199 optionally includes uploading the stored analyte sensor data to a server system by the upload computing device.

Example 201 is a system for measuring a parameter related to patient health, the system comprising: an analyte sensor system configured to perform operations comprising: detecting that the analyte sensor system has been applied to a host; storing, by the analyte sensor system, analyte data describing the host; determining, by the analyte sensor system, that sensor use at the analyte sensor system has terminated; and uploading, by the analyte sensor system, stored analyte data to an upload computing device.

In Example 202, the subject matter of Example 201 optionally includes the operations further comprising: after determining that the sensor use at the analyte sensor system has terminated, broadcasting, by the analyte sensor system, system identification data; receiving, by the analyte sensor system and from the upload computing device, a communication request comprising the system identification data; and establishing, by the analyte sensor system, a communication session with the upload computing device responsive to the communication request, wherein the uploading is performed using the communication session.

In Example 203, the subject matter of any one or more of Examples 201-202 optionally includes the operations further comprising: after determining that the sensor use at the analyte sensor system has terminated, receiving, by the analyte sensor system, an upload request from the upload computing device; and receiving, from the upload computing device, authentication data.

In Example 204, the subject matter of any one or more of Examples 201-203 optionally includes the operations further comprising: after determining that the sensor use at the analyte sensor system has terminated, receiving, by the analyte sensor system, an upload request from the upload computing device; broadcasting, by the analyte sensor system, system identification data; receiving, from the upload computing device, authentication data; and establishing, by the analyte sensor system, a communication session with the upload computing device, wherein the uploading transmitting the stored analyte data to the upload computing device.

In Example 205, the subject matter of any one or more of Examples 201-204 optionally includes wherein detecting that the analyte sensor system has been applied to a host comprises determining that the analyte sensor system has provided sensor readings above a threshold value.

In Example 206, the subject matter of any one or more of Examples 201-205 optionally includes wherein detecting that the analyte sensor system has been applied to a host comprises determining that the analyte sensor system has provided sensor readings above a threshold value for more than a threshold time.

In Example 207, the subject matter of any one or more of Examples 201-206 optionally includes wherein determining that sensor use at the analyte sensor system has terminated comprises determining that more than a threshold time has elapsed since the analyte sensor system was applied to the host.

In Example 208, the subject matter of any one or more of Examples 201-207 optionally includes the upload computing device, wherein the upload computing device is configured to perform operations comprising uploading the stored analyte sensor data to a server system.

Example 209 is a machine-readable medium comprising instructions thereon that, when executed by at least one processor, cause the at least one processor to perform operations comprising: detecting that an analyte sensor system has been applied to a host; storing analyte data describing the host; determining that sensor use at the analyte sensor system has terminated; and uploading stored analyte data to an upload computing device.

In Example 210, the subject matter of Example 209 optionally includes the operations further comprising: after determining that the sensor use at the analyte sensor system has terminated, broadcasting system identification data; receiving from the upload computing device a communication request comprising the system identification data; and establishing a communication session with the upload computing device responsive to the communication request, wherein the uploading is performed using the communication session.

In Example 211, the subject matter of any one or more of Examples 209-210 optionally includes the operations further comprising: after determining that the sensor use at the analyte sensor system has terminated, receiving an upload request from the upload computing device; and receiving, from the upload computing device, authentication data.

In Example 212, the subject matter of any one or more of Examples 209-211 optionally includes the operations further comprising: after determining that the sensor use at the analyte sensor system has terminated, receiving an upload request from the upload computing device; broadcasting system identification data; receiving authentication data; and establishing a communication session with the upload computing device, wherein the uploading transmitting the stored analyte data to the upload computing device.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3 is table that shows example patient states, physiologic conditions, and example treatments.

FIG. 22C is a flowchart showing one example of a process that can be executed in the system of FIG. 22B to display CGM data at the activity sensor.

DETAILED DESCRIPTION

Figure 1:
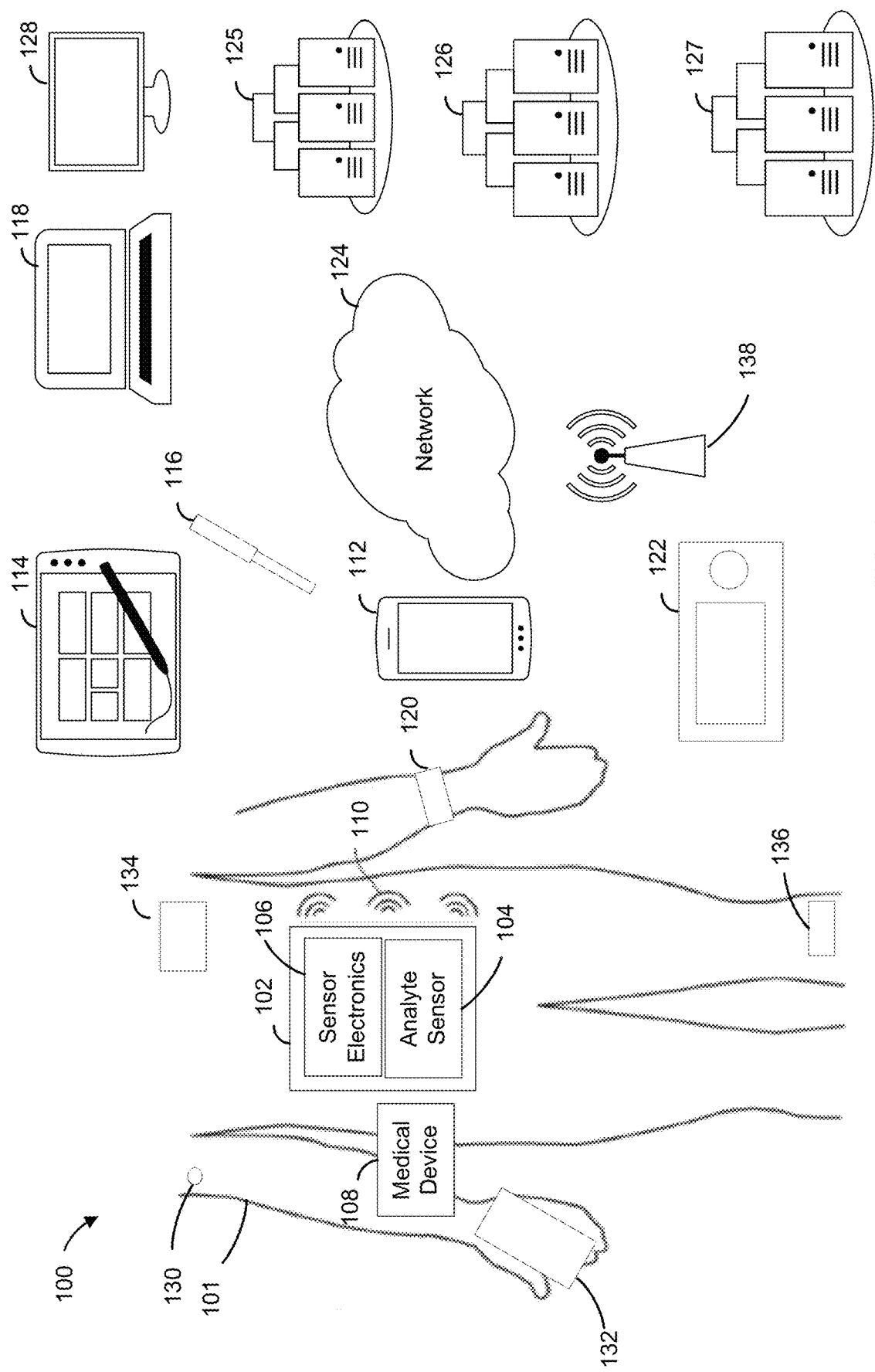
FIG. 1 is an illustration of an example medical device system.

The present inventors have recognized, among other things, that a patient may advantageously be monitored or managed with a combination of techniques that have differing patterns of information collection. Typically, to enhance patient management, higher-fidelity and greater quantities of data is desired to inform patient management decisions. A counter-intuitive approach uses less data or lower-fidelity data, in combination with information learned from high-fidelity data (e.g., a correlation between the types of data) to guide patient management. For example, a relationship between the different types of collected data may be used to inform management of the patient during time periods when one or more of the types of data is not available. In some examples, analyte information that is automatically collected by a sensor from a host on a schedule ("continuous analyte monitoring"), such as glucose information that is automatically collected by a glucose sensor ("continuous glucose monitoring" or "CGM") may be correlated to other types of information (e.g., activity captured by a wearable activity sensor), which may allow for estimation of an estimated glucose concentration level (or level of another analyte) based on the correlation. In some examples, two or more types of data (e.g., CGM data and activity data) may be collected from a patient, and data obtained during a period when both CGM and activity data are collected may be used to develop or tune a system or algorithm to infer a first type of data (e.g., glucose concentration level) from a second type of data (e.g., activity or heart rate) or from the second type of data and an auxiliary input (e.g., administration of a medication or consumption of a meal.) In other words, a non-CGM sensor system may be "calibrated" to estimated glucose values using contemporaneously-obtained CGM data and non-CGM data. In some examples, continuous glucose monitoring may be performed intermittently: during collection periods, glucose concentration levels may be collected on a schedule (e.g., every 5 minutes), but the CGM data collection may only occur during certain time periods, such as when a patient is wearing an activated CGM sensor, which may occur, for example, for a one-week or ten day period each month or every 3 months.

In some examples, a need or desire to implement a second type of data collection (e.g., intermittent CGM data collection) or a collection parameter (e.g., periodicity for intermittent collection), may be determined based upon a first type of data (e.g., blood glucose meter data or activity data). In some examples, a relationship or aspects of intermittent collection may be used to determine a collection parameter for a different monitoring technique. For example, CGM data may be used to determine a time or schedule for one or more blood glucose meter tests. In another example, blood glucose meter test results or activity data may be used to determine a CGM monitoring scheme (e.g., a schedule for intermittent CGM data collection or a number of sensors to be used in CGM monitoring.) In some examples, an oral medication therapy or injected insulin therapy (e.g., basal insulin) may be determined (or evaluated or redetermined) based in part on CGM information, such as intermittent CGM monitoring. While CGM information is referenced as an example throughout this description, the described examples are also applicable to other types of analytes (e.g., references to continuous glucose monitoring are applicable generally to continuous analyte monitoring.)

Overview

Patient management may be more effective when informed by timely information about the patient. For example, physiologic information, environmental information, or behavioral information may be used to determine guidance (e.g., dietary or exercise guidance) or therapy (e.g., oral medication regime) for the patient or to determine changes or improvements to a patient management scheme. Patients who have a blood glucose control condition such as type 2 diabetes may especially benefit from a patient management scheme that uses timely information. Some monitoring systems or devices, such as a continuous glucose monitor, may provide a strong signal about the glucose control condition (e.g., high glucose concentration level, normal level, or low level) of a patient, but continuous use of such systems may not be desired due to expense (e.g., the expense of CGM sensors and monitoring) or a burden on the patient (e.g., the need to wear and manage a CGM on the body.) Other systems and devices (e.g., wearable activity monitor, smart watch, smart phone) may be less burdensome or less expensive but tend to provide information that may have less direct relation to blood glucose levels. For example, activity tends to be helpful in controlling blood glucose levels, but an actual blood glucose concentration level cannot be easily inferred from activity information alone, and the effect of activity on blood glucose may vary widely among patients, or types of patients (e.g., amongst subgroups in a population.)

To balance cost and the need for accurate information about glucose management, different types of patient data may be collected for one or more overlapping time periods, which may allow for determination of patient management information based on relationships between different types of data. Such a relationship may be used to guide patient management when one of the types of data is not available. For example, a continuous glucose monitor and an activity monitor may be used during an overlapping time period, and a relationship between glucose concentration level information and activity information may be learned from the CGM and activity data. In some examples, a user may be instructed to wear an activity sensor (e.g., watch) continuously (e.g., at least a portion of each day), and the user may be instructed to wear a continuous glucose sensor for a defined time period (e.g., two-week trial period) or continuously (e.g., for a two-week session every three months). The data may be collected by a system (e.g., using a mobile device and server) and analyzed to determine a relationship between glucose levels and activity. In various examples, activity may be correlated with a glucose concentration level or range, or may be correlated with an impact on glucose concentration (e.g., a particular amount of activity causes a determined impact on glucose, which may vary based on glucose level due to lower insulin sensitivity (i.e., insulin resistance) at higher glucose levels) or may be correlated with a glucose level trend (e.g., rate of change of the glucose level associated with an amount, intensity, or type of activity), any of which may be used to infer an estimated glucose concentration level (e.g., 120 mg/dL), range (e.g., 120-160 mg/dL), status (e.g., out of target range, or in range), or other estimate of glucose level management. One or more of these glucose estimates, or information based on an estimate (e.g., time-in-range for a day) may be delivered to the patient, which, in various examples, may occur in real time, or on demand, or recurrently (e.g., hourly, daily, weekly, three times a day, or before or after meals.)

To facilitate determination of relationships amongst types of data, different types of data (e.g., CGM data and activity data) may be correlated with one or more of time (e.g., to allow matching of CGM data with corresponding activity data), location, day, patient-input data (e.g., meals or activity), or other information. The correlations with time, location, day, patient-input data, or other information may also be used to determine a relationship between types of data.

In some examples, the collected sensor data may be used in combination with population-based data, such as gender, age, location, ethnicity, job type, A1C, BMI, weight, or other demographic information to determine a glucose control estimate (e.g., estimated glucose level, range, or status.) In some examples, a system may build up population cohorts segmented by glucose profile behavior, and a user matched up to a specific cohort may receive statistical feedback. Based on this type of population information, a glucose estimate may be used to determine population-based guidance, which may be delivered (e.g., presented on a smart device) to the patient. For example, a patient may receive guidance: "70% of people like you are estimated to be out of range around this time. Have you considered going for a walk?"

In some examples, a model may be developed (e.g., learned from collected data), and relationships may be reflected in the model. For example, a state, such as glucose state, may be determined by applying one or more inputs (e.g., activity), to the model.

While specific types of patient management information (e.g., CGM and activity data) may be the subject of specific examples for purpose of explanation, it is understood that the techniques and methods, and system herein may be applied to other differing types of information, such as different types of monitored analytes (other than glucose), or different types of physiologic information (e.g., heart rate, respiration, galvanic skin response or other skin qualities, blood ketones, urine ketones, oxygen concentration) or types of ambient information (e.g., location, environment, temperature) and relationships among two or more types of information may be used to determine health (e.g., diabetic) information about the patient when one or more types of information are not available.

Example System

FIG. 1 is an illustration of an example system 100 that may include a variety of sensor systems of devices. The system 100 may include an analyte sensor system 102 that may be coupled to a host 101. The host 101 may be a human patient. The patient may, for example, be subject to a temporary or permanent diabetes condition or other health condition for which data-driven patient management or analyte monitoring may be useful.

The analyte sensor system 102 may include an analyte sensor 104, which may for example be a glucose sensor. The glucose sensor may be any device capable of measuring the concentration of glucose. For example, the analyte sensor 104 may be fully implantable, or the analyte sensor may be wearable on the body (e.g., on the body but not under the skin), or the analyte sensor may be a transcutaneous device (e.g., with a sensor residing under or in the skin of a host). It should be understood that the devices and methods described herein can be applied to any device capable of detecting a concentration of glucose and providing an output signal that represents the concentration of glucose (e.g., as a form of analyte data).

The analyte sensor system 102 may also include sensor electronics 106. In some examples, the analyte sensor 104 and sensor electronics 106 may be provided as an integrated package. In other examples, the analyte sensor 104 and sensor electronics 106 may be provided as separate components or modules. For example, the analyte sensor system 102 may include a disposable (e.g., single-use) base that may include the analyte sensor 104, a component for attaching the sensor to a host (e.g., an adhesive pad), or a mounting structure configured to receive another component. The system may also include a sensor electronics package, which may include some or all of the sensor electronics 106 shown in FIG. 2. The sensor electronics package may be reusable.

An analyte sensor may use any known method, including invasive, minimally-invasive, or non-invasive sensing techniques (e.g., optically excited fluorescence, microneedle, transdermal monitoring of glucose), to provide a data stream indicative of the concentration of the analyte in a host. The data stream may be a raw data signal, which may be converted into a calibrated and/or filtered data stream that is used to provide a useful value of the analyte (e.g., estimated blood glucose concentration level) to a user, such as a patient or a caretaker (e.g., a parent, a relative, a guardian, a teacher, a doctor, a nurse, or any other individual that has an interest in the wellbeing of the host).

Analyte sensor 104 may, for example, be a continuous glucose sensor, which may, for example, include a subcutaneous, transdermal (e.g., transcutaneous), or intravascular device. In some embodiments, such a sensor or device may recurrently (e.g., periodically or intermittently) analyze sensor data. The glucose sensor may use any method of glucose-measurement, including enzymatic, chemical, physical, electrochemical, spectrophotometric, polarimetric, calorimetric, iontophoretic, radiometric, immunochemical, and the like. In various examples, the analyte sensor system 102 may be or include a continuous glucose monitor sensor available from DexCom™ (e.g., the DexCom G5™ sensor or Dexcom G6™ sensor or any variation thereof), from Abbott™ (e.g., the Libre™ sensor), or from Medtronic™ (e.g. the Enlite™ sensor).

In some examples, analyte sensor 104 may be an implantable glucose sensor, such as described in U.S. Pat. No. 6,001,067 and U.S. Patent Publication No. US-2005-0027463-A1. In some examples, analyte sensor 10 may be a transcutaneous glucose sensor, such as described in to U.S. Patent Publication No. US-2006-0020187-A1. In some examples, analyte sensor 10 may be configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007. In some examples, the continuous glucose sensor may include a transcutaneous sensor such as described in U.S. Pat. No. 6,565,509 to Say et al., for example. In some examples, analyte sensor 10 may be a continuous glucose sensor that includes a subcutaneous sensor such as described in U.S. Pat. No. 6,579,690 to Bonnecaze et al. or U.S. Pat. No. 6,484,046 to Say et al., for example. In some examples, the continuous glucose sensor may include a refillable subcutaneous sensor such as described in U.S. Pat. No. 6,512,939 to Colvin et al., for example. The continuous glucose sensor may include an intravascular sensor such as described in U.S. Pat. No. 6,477,395 to Schulman et al., for example. The continuous glucose sensor may include an intravascular sensor such as described in U.S. Pat. No. 6,424,847 to Mastrototaro et al., for example.

The system 100 may also include a second medical device 108, which may, for example, be or include a wearable monitor or a drug delivery device. For example, the second medical device 108 may be or include a drug delivery device such as an insulin pump, insulin pen, or similar device. In some examples, the medical device 108 may be or include a sensor, a heart rate sensor, a respiration sensor, a motion sensor (e.g. accelerometer), posture sensor (e.g. 3-axis accelerometer), acoustic sensor (e.g. to capture ambient sound or sounds inside the body, such as respiration), or another analyte sensor. In some examples, medical device 108 may be wearable, e.g. on a watch, glasses, contact lens, patch, wristband, ankle band, or other wearable item, or may be incorporated into a handheld device (e.g., a smartphone). In some examples, the medical device 108 may include a multi-sensor patch that may, for example, detect one or more of an analyte level (e.g. glucose, lactate, insulin or other substance), heart rate, respiration (e.g., using impedance), activity (e.g. using an accelerometer), posture (e.g. using an accelerometer), galvanic skin response, tissue fluid levels (e.g. using impedance or pressure).

The analyte sensor system 102 may communicate with the second medical device 108 via a wired connection, or via a wireless communication signal 110. For example, the analyte sensor system may be configured to communicate using via radio frequency (e.g. Bluetooth, Bluetooth Low Energy (LE), Medical Implant Communication System (MICS), Wi-Fi, NFC, RFID, Zigbee, Z-Wave or other communication protocols), optically (e.g. infrared), sonically (e.g. ultrasonic), or a cellular protocol (e.g., CDMA (Code Division Multiple Access) or GSM (Global System for Mobiles), or wired connection (e.g. serial, parallel, etc.).

The system 100 may also include a wearable sensor 130, which may include a sensor circuit (e.g., a sensor circuit configured to detect a glucose concentration or other analyte concentration) and a communication circuit, which may, for example, be a near field communication (NFC) circuit. In some examples, information from the wearable sensor 130 may be retrieved from the wearable sensor 130 using a user device 132 such as a smart phone that is configured to communicate with the wearable sensor 130 via NFC when the user device 132 is placed near the wearable sensor 130 (e.g., swiping the user device 132 over the sensor retrieves sensor data from the wearable sensor using NFC.) The use of NFC communication may reduce power consumption by the wearable sensor, which may reduce the size of a power source (e.g., battery or capacitor) in the wearable sensor or extend the usable life of the power source. In some examples, the wearable sensor 130 may be wearable on an upper arm as shown. In some examples, a wearable sensor 134 may additionally or alternatively be on the upper torso of the patient (e.g. over the heart or over a lung), which may, for example, facilitate detecting heart rate, respiration, or posture. A wearable sensor 136 may also be on the lower body (e.g., on a leg).

In some examples, an array or network of sensors may be associated with the patient. For example, one or more of the analyte sensor system 102, medical device 108, wearable device 120 and an additional sensor 130 may communicate with one another via wired or wireless (e.g., Bluetooth, Bluetooth LE, MICS, NFC, or any of the other options discussed above) communication. The additional sensor 130 may be any of the examples discussed above with respect to medical device 108. The analyte sensor system 102, medical device 108, and additional sensor 130 on the host 101 are provided for the purpose of illustration and discussion and are not necessarily drawn to scale.

The system 100 may also include one or more peripheral devices, such as a hand-held smart device (e.g., smartphone) 112, a tablet 114, a smart pen 116 (e.g., insulin delivery pen with processing and communication capability), a computer 118, a wearable device such as a wearable device 120, or a peripheral medical device 122 (which may be a proprietary device such as a proprietary user device available from DexCom), any of which may communicate with the analyte sensor system 102 via a wireless communication signal, and may also communicate over a network 124 with a server system (e.g., remote data center) 125 or with a remote terminal 128 to facilitate communication with a remote user (not shown) such as a technical support staff member or a clinician.

The wearable device 120 may include an activity sensor, a heart rate monitor (e.g., light based sensor or electrode based sensor), a respiration sensor (e.g., acoustic or electrode based), a location sensor (e.g., GPS), or other sensors.

The system 100 may also include a wireless access point (WAP) 138 that may be used to communicatively couple one or more of analyte sensor system 102, network 124, one or more server systems 126, 125, 127, medical device 108 or any of the peripheral devices described above. For example, WAP 138 may provide Wi-Fi and/or cellular connectivity within system 100. Other communication protocols (e.g., Near Field Communication (NFC) or Bluetooth) may also be used among devices of the system 100.

In some examples, a first server system 125 may be used to collect analyte data from analyte sensor system 102 and/or the plurality of other devices, and to perform analytics on collected data, generate or apply universal or individualized models for glucose levels, and communicate such analytics, models, or information based thereon back to one or more of the devices in the system 100. The system may include one or more additional servers 126, 127. For example, the first server system 125 may handle (e.g., receive or store or send) CGM data, and a second server system 126 may house general patient information or medical data (e.g., insurance information). The first server system 125 or second server system 126 may include a decision-support system, which may, for example, determine guidance for a patient, determine an estimated blood glucose level (e.g., based on a surrogate data) or may determine other information (e.g., a correlation with other types of information) using any of the various techniques described herein. The guidance, glucose concentration level, or other information may be transmitted via a network 124 and delivered to a patient or caretaker device, such as hand-held device 112 or tablet 114. In some examples, CGM information may be delivered to both a patient device (such as hand-held device 112) and shared with a device of a caretaker or family member. Information about remote monitoring of analyte measurements is provided in U.S. patent application Ser. No. 15/632,181, which is published as U.S. publication number 20170293732A1, and which is incorporated by reference.

The system 100 may also include a third server system 127, which may receive or store a second type of patient information or information from another source, such as sensor data from a wearable sensor. In various examples, two or more of the servers 125, 126, 127 may be combined, or all three servers may be combined, or the operations may be distributed differently amongst the servers or sub-tasks may be delegated to additional servers or other resources. In some examples, a smart device such as wearable device 120 or hand-held device 112 may run a single application that collects, processes, or transmits (e.g., to a server or another smart device) two types of data (e.g., high-fidelity data and low-fidelity data, or CGM data and activity data). In another example, a smart device may run two separate applications that each collect, processes, or transmits a type of data. In some examples, a smart device may run separate applications for collection of data, and one application may receive data from the other applications (e.g., a CGM application may receive activity information collected by an activity app.) Information about inter-application communications is described in U.S. patent application Ser. No. 15/474,886, U.S. publication number 20170286194A1, which is incorporated by reference.

In some examples, one smart device may collect information from another smart device, e.g., the hand-held device 112 may collect activity information from wearable device 120. In some examples, a correlation between types of data (further described below) may be determined by a smart device, or by a server (e.g., server 125), or both or a combination thereof.

Figure 2:
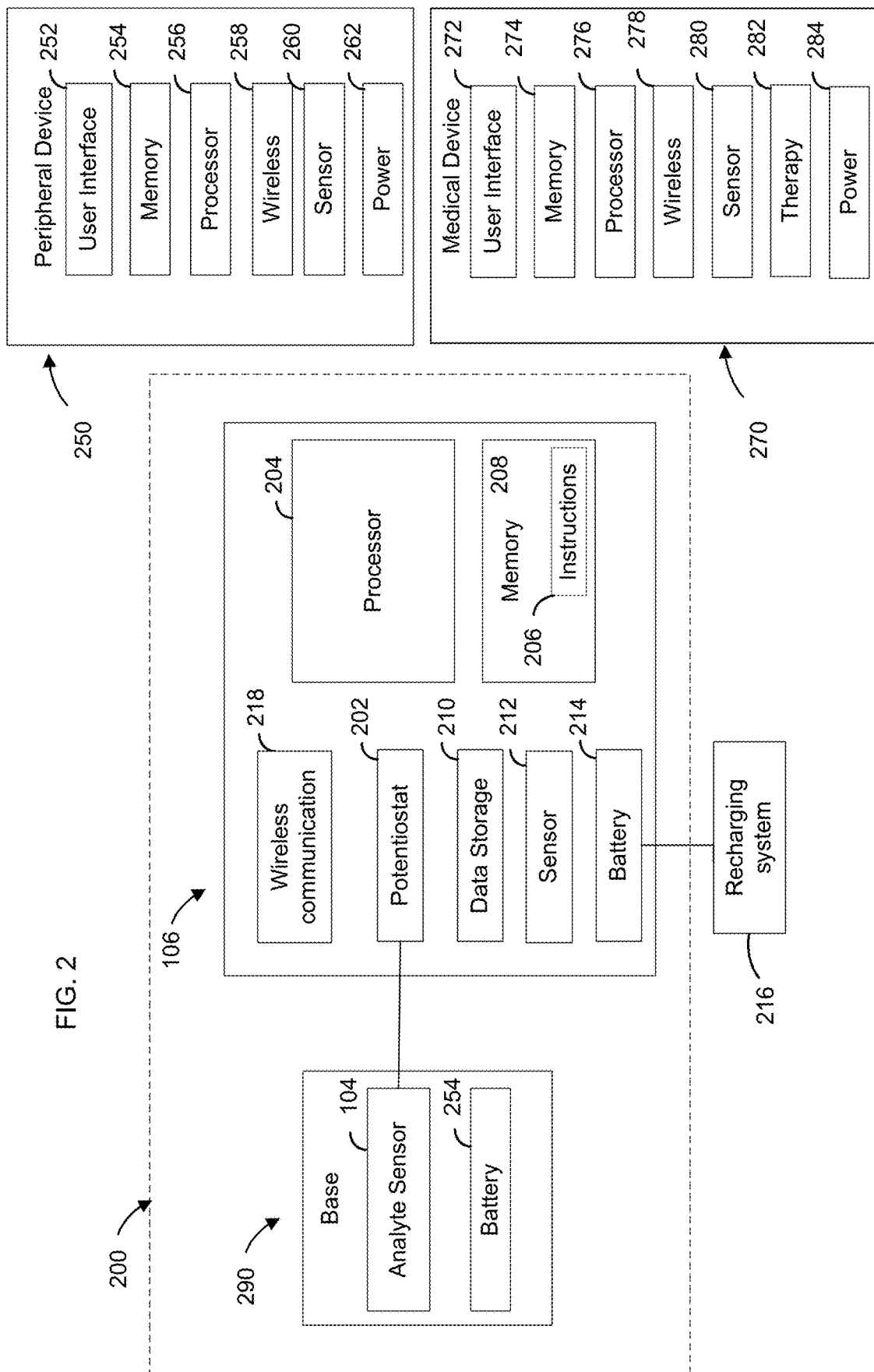
FIG. 2 is a schematic illustration of various example electronic components that may be part of the medical device system shown in FIG. 1.

FIG. 2 is a schematic illustration of various example electronic components that may be part of a medical device system 200. In an example, the system may include a sensor electronics 106 and a base 290. While a specific example of division of components between the base and sensor electronics is shown, it is understood that some examples may include additional components in the base 290 or in the sensor electronics 106, and some of the components that are shown in the sensor electronics 106 may be alternative or additionally (e.g., redundantly) provided in the base. In an example, the base 290 may include the analyte sensor 104 and a battery 292. In some examples, the base may be replaceable, and the sensor electronics 106 may include a debouncing circuit (e.g., gate with hysteresis or delay) to avoid, for example, recurrent execution of a power-up or power down process when a battery is repeatedly connected and disconnected or avoid processing of noise signal associated with removal or replacement of a battery.

The sensor electronics 106 may include electronics components that are configured to process sensor information, such as sensor data, and generate transformed sensor data and displayable sensor information. The sensor electronics 106 may, for example, include electronic circuitry associated with measuring, processing, storing, or communicating continuous analyte sensor data, including prospective algorithms associated with processing and calibration of the sensor data. The sensor electronics 106 may include hardware, firmware, and/or software that enables measurement of levels of the analyte via a glucose sensor. Electronic components may be affixed to a printed circuit board (PCB), or the like, and can take a variety of forms. For example, the electronic components may take the form of an integrated circuit (IC), such as an Application-Specific Integrated Circuit (ASIC), a microcontroller, and/or a processor.

As shown in FIG. 2, the sensor electronics 106 may include a potentiostat 202, which may be coupled to the analyte sensor 104 and configured to recurrently obtain analyte sensor readings using the analyte sensor, for example by continuously or recurrently placing a voltage bias across sensor electrodes and measuring a current flow indicative of analyte concentration. The sensor electronics may also include a processor 204, which may retrieve instructions 206 from memory 208 and execute the instructions to determine control application of bias potentials to the analyte sensor 104 via the potentiostat, interpret signals from the sensor, or compensate for environmental factors. The processor may also save information in data storage memory 210 or retrieve information from data storage 210. In various examples, data storage memory 210 may be integrated with memory 208, or may be a separate memory circuit, such as a non-volatile memory circuit (e.g., flash RAM). Examples of systems and methods for processing sensor analyte data are described in more detail herein and in U.S. Pat. Nos. 7,310,544 and 6,931,327.

The sensor electronics 106 may also include a sensor 212, which may be coupled to the processor. The sensor 212 may, for example, be a temperature sensor or an accelerometer. The sensor electronics 106 may also include a power source such as a capacitor or battery 214, which may be integrated into the sensor electronics, or may be removable, or part of a separate electronics package. The battery 214 (or other power storage component, e.g., capacitor) may optionally be rechargeable via a wired or wireless (e.g., inductive or ultrasound) recharging system 216. The recharging system may harvest energy or may receive energy from an external source or on-board source. In various examples, the recharge circuit may include a triboelectric charging circuit, a piezoelectric charging circuit, an RF charging circuit, a light charging circuit, an ultrasonic charging circuit, a heat charging circuit, a heat harvesting circuit, or a circuit that harvests energy from the communication circuit. In some examples, the recharging circuit may recharge the rechargeable battery using power supplied from a replaceable battery (e.g., a battery supplied with a base component.)

The sensor electronics 106 may also include a wireless communication circuit 218, which may for example include a wireless transceiver operatively coupled to an antenna. The wireless communication circuit 218 may be operatively coupled to the processor and may be configured to wirelessly communicate with one or more peripheral devices or other medical devices, such as an insulin pump or smart insulin pen.

The peripheral device 250 may, for example, be a wearable device (e.g., activity monitor), such as a wearable device 120. In other examples, the peripheral device 250 may be a hand-held device 112 (e.g., smartphone or other device such as a proprietary handheld device available from Dexcom), a tablet 114, a smart pen 116, or special-purpose computer 118 shown in FIG. 1.

The peripheral device 250 may include a user interface 252, a memory circuit 254, a processor 256, a wireless communication circuit 258, a sensor 260, a power source 262 (e.g., battery or capacitor) or any combination thereof. The peripheral device may not necessarily include all of the components shown in FIG. 2. The user interface 252 of the peripheral device 250 may, for example, include a touch-screen interface, a microphone (e.g., to receive voice commands), or a speaker, a vibration circuit, or any combination thereof, which may receive information from a user (e.g., glucose values) or deliver information to the user such as glucose values, glucose trends (e.g., an arrow, graph, or chart), or glucose alerts. The processor 256 may be configured to present information to a user, or receive input from a user, via the user interface 252. The processor 256 may also be configured to store and retrieve information, such as communication information (e.g., pairing information or data center access information), user information, sensor data or trends, or other information in the memory circuit 254. The wireless circuit communication circuit 258 may include a transceiver and antenna configured communicate via a wireless protocol, such as Bluetooth, MICS, or any of the other options discussed above. The sensor 260 may, for example, include an accelerometer (e.g., in an activity monitor such as a watch), a temperature sensor, a location sensor, biometric sensor, or blood glucose sensor, blood pressure sensor, heart rate sensor, respiration sensor, or another physiologic sensor. The device may include a plurality of sensors of differing types.

The peripheral device 250 may be configured to receive and display sensor information that may be transmitted by sensor electronics 106 (e.g., in a customized data package that is transmitted to the display devices based on their respective preferences). Sensor information (e.g., blood glucose concentration level) or an alert or notification (e.g., "high glucose level", "low glucose level" or "fall rate alert" may be communicated via the user interface 252 (e.g., via visual display, sound, or vibration). In some examples, the peripheral device 250 may be configured to display or otherwise communicate the sensor information as it is communicated from the sensor electronics module (e.g., in a data package that is transmitted to respective display devices). For example, the peripheral device 250 may transmit data that has been processed (e.g., an estimated analyte concentration level that may be determined by processing raw sensor data), so that a device that receives the data may not be required to further process the data to determine usable information (such as the estimated analyte concentration level.) In other examples, the peripheral device 250 may process or interpret the received information (e.g., to declare an alert based on glucose values or a glucose trend. In various examples, the peripheral device 250 may receive information directly from sensor electronics 106, or over a network (e.g., via a cellular or Wi-Fi network that receives information from the sensor electronics or from a device that is communicatively coupled to the sensor electronics 106.)

Referring again to FIG. 2, the medical device 270 may include a user interface 272, a memory circuit 274, a processor 276, a wireless communication circuit 278, a sensor 280, a therapy circuit 282, or any combination thereof. In some examples, the medical device 270 may not include all of the components illustrated in FIG. 2. For example, the medical device may not include a user interface 272, or may not include a therapy circuit 282, or may not include a sensor 280.

The user interface 272 may, for example, include a touch-screen interface, a microphone, or a speaker, a vibration circuit, or any combination thereof, which may receive information from a user (e.g., glucose values, alert preferences, calibration coding) or deliver information to the user, such as e.g., glucose values, glucose trends (e.g., an arrow, graph, or chart), or glucose alerts. The processor 276 may be configured to present information to a user, or receive input from a user, via the user interface 272. The processor 276 may also be configured to store and retrieve information, such as communication information (e.g., pairing information or data center access information), user information, sensor data or trends, or other information in the memory circuit 274. The wireless circuit communication circuit 278 may include a transceiver and antenna configured to communicate via a wireless protocol, such as Bluetooth, Medical Implant Communication System (MICS), Wi-Fi, Zigbee, or a cellular protocol (e.g., CDMA (Code Division Multiple Access) or GSM (Global System for Mobiles). The sensor 280 may, for example, include an accelerometer, a temperature sensor, a location sensor, biometric sensor, or blood glucose sensor, blood pressure sensor, heart rate sensor, respiration sensor, or another physiologic sensor. The medical device 270 may include two or more sensors (or memories or other components), even though only one is shown in the example in FIG. 2. In various examples, the medical device 270 may be a smart handheld glucose sensor (e.g., blood glucose meter), a drug pump (e.g., insulin pump), or any other physiologic sensor device (e.g., wearable device 120), therapy device, or combination thereof. In various examples, the medical device 270 may be the medical device 108, peripheral device 122, wearable device 120, wearable sensor 130, wearable sensor 134, or wearable sensor 136 shown in FIG. 1. In examples where the medical device 270 is an insulin pump, the pump and analyte sensor system may be in two-way communication (e.g., so the pump can request a change to an analyte transmission protocol, e.g., request a data point or request data on a more frequency schedule), or the pump and analyte sensor system may communicate using one-way communication (e.g., the pump may receive analyte concentration level information from the analyte sensor system. In one-way communication, a glucose value may be incorporated in an advertisement message, which may be encrypted with a previously-shared key. In a two-way communication, a pump may request a value, which the analyte system may share, or obtain and share, in response to the request from the pump, and any or all of these communications may be encrypted using one or more previously-shared keys. An insulin pump may receive and track analyte (e.g., glucose) values transmitted from analyte sensor system 102 using one-way communication to the pump for one or more of a variety of reasons. For example, an insulin pump may suspend or activate insulin administration based on a glucose value being below or above a threshold value.

In some examples, the system 100 shown in FIG. 1 may include two or more peripheral devices that each receive information directly or indirectly from the analyte sensor system 102. Because different display devices may provide different user interfaces, the content of the data packages (e.g., amount, format, and/or type of data to be displayed, alarms, and the like) may be customized (e.g., programmed differently by the manufacture and/or by an end user) for each particular device. For example, in the embodiment of FIG. 1, a plurality of different peripheral devices may be in direct wireless communication with a sensor electronics module (e.g., such as an on-skin sensor electronics 106 that is physically connected to the continuous analyte sensor 104) during a sensor session to enable a plurality of different types and/or levels of display and/or functionality associated with the displayable sensor information, or, to save battery power in the sensor system 102, one or more specified devices may communicate with the analyte sensor system and relay (i.e., share) information to other devices directly or through a server system (e.g., network-connected data center) 125.

FIG. 3 shows a table 301 that shows example patient states 305, physiologic conditions 310, and example treatments 315. The table is arranged to reflect a typical progression of a patient from a normal state into pre-diabetes and eventually into a diabetic state (e.g., Type 2 diabetes), which may occur over days, weeks, months, or years, depending on the circumstances. The alignment of states, conditions, and treatments in the table is provided for purpose of explanation and may not be the same for each patient. In some patients, insulin resistance or insufficient insulin production by pancreatic β-cells may contribute to the progression of a patient into pre-diabetes and eventually into Type 2 diabetes. Type 2 diabetes and high blood glucose levels are associated with risks of myocardial infarction, stroke, vascular problems and mortality.

A patient in a normal state may have no problematic physiologic conditions to be managed, and consequently may need no treatment. A patient may become insulin resistant due to one or more of a variety of factors, such as age, diet, lifestyle, pregnancy, genetic factors, or other factors.

As a patient becomes insulin resistant, the patient may begin to experience higher than normal circulating levels of insulin, known as "hyperinsulinemia." To manage hyperinsulinemia and insulin resistance, a patient may begin a patient management regimen, which may include diet and exercise modifications, such as consumption of fewer calories or fewer carbohydrates (especially simple sugars and other carbohydrates that may be quickly processed by the body into glucose) and an increase in activity or amount of exercise.

As a patient's condition worsens, the patient may develop higher than normal blood glucose concentration levels, which is known as "hyperglycemia." For example, a patient may initially exhibit post-meal hyperglycemia, in which glucose levels spike to higher-than-normal levels after consumption of a meal, and then trend back down as time passes after the meal. Glucose levels that are higher than normal, but not high enough to trigger a Type 2 diabetes diagnosis may be referred to as "impaired glucose tolerance." The patient continues with diet and exercise modifications to address post-meal glycemia or impaired glucose tolerance, and the patient may also be prescribed an oral medication. An oral medication may, for example, stimulate the production of insulin by pancreatic beta cells (e.g., sulfonylureas or meglitinides), decrease glucose production by the liver (e.g., biguanides), improve the operation of circulating insulin (e.g., thiazolindinediones), reabsorb glucose in the kidneys (e.g., SGLT2 inhibitors) block the breakdown of starches in the intestine (e.g., alpha-glucosidase inhibitors), or prevent the breakdown of glucose-lowering compounds (e.g., DPP-4 inhibitors). Other oral medications and combinations of complimentary or compatible medications are also possible treatments.

Impaired glucose intolerance can progress into impaired fasting glucose, in which a patient may have abnormally high glucose concentration levels not just soon after a meal, but also when fasting ("fasting hyperglycemia.") For example, a fasting blood glucose level over 100 mg/dL may be considered prediabetes. A patient may continue with diet and exercise treatments and oral medication. The patient may also be prescribed insulin to attempt to lower glucose levels.

Information about the patient may also be used to assist with management of a patient's condition. For example, sensor data, such as activity data or physiological data (e.g., heart rate or respiration) may be used to develop guidance for the patient about management of their health. Information about a patient may be of a particular physiological type (e.g., glucose information, heart rate information, respiration information, pulse information, etc.).

Despite efforts to control glucose or insulin levels, the condition of some patients may continue to decline, and they may eventually progress into Type 2 diabetes. For example, when fasting (overnight) glucose levels are 126 mg/dL or higher, a patient may be considered to have type 2 diabetes. Some patients may progress deeper into diabetes, with glucose levels that continue to increase, which tends to raise the risk of complications such as cardiovascular disease, vascular problems, or stroke.

To help manage glucose levels, prediabetes, or Type 2 diabetes, a patient may benefit from monitoring using a physiological sensor, such as a continuous glucose monitor. In some examples, information from other sources, such as data or data patterns from an activity sensor or blood glucose meter, may be used to determine whether to begin use of a physiological sensor, such as a continuous glucose monitor.

In some examples, a continuous glucose monitor (or other physiologic sensor) may be used for a trial period (e.g., 3 days, 7 days, 10 days, 14 days, 30 days, or 3 months). In some examples, information about management of glucose levels may be learned from a trial period. The learned information from the trial period may be subsequently applied, optionally in combination with other information such as activity, location, heart rate, user input information, or other glucose information (e.g., single-point glucose data such as blood glucose meter data, glucose data from an NFC enabled sensor, optical glucose data, or glucose information collected with another technique) to better manage a patient's condition. For example, the relationship of patient's activity or behavior (as deduced from activity, location, heart rate, or user input information or other information) on a patient's glucose concentration level may be learned during the trial period, and this relationship may be later used to determine guidance for the patient.

In some situations, a continuous glucose monitor may be used intermittently. For example, glucose concentration levels may be collected from a patient using a continuous glucose monitor on a specified schedule, e.g., a specified number of days, weeks, or series of days (e.g., 10 days) per quarter month, or year. Intermittently collected CGM information may be used to actively manage glucose levels (e.g., in real time), or may be used to update or refine learned relationship between estimated glucose levels from a CGM and other information, such as activity.

Figure 4:
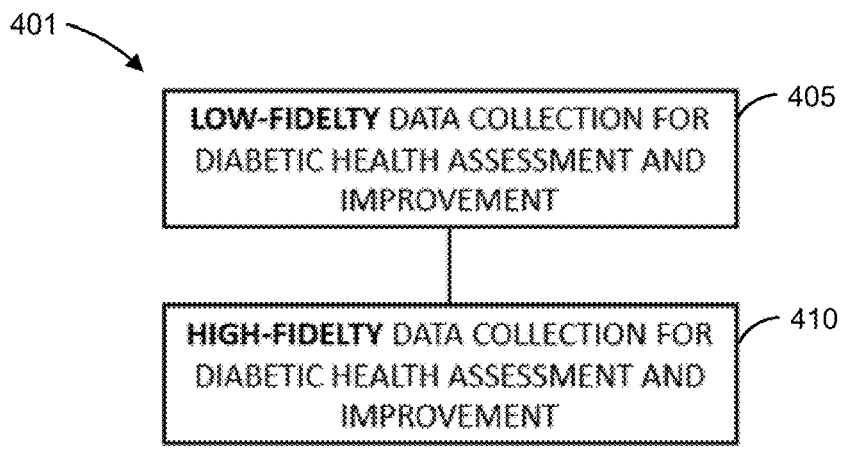
FIG. 4 is a flowchart illustration of an example method of progressing from a low-fidelity data collection technique to a high-fidelity data collection technique.

FIG. 4 is a flowchart illustration of a method 401 of progressing from a low-fidelity data collection technique to a high-fidelity data collection technique. At 405, low-fidelity data is collected. The low-fidelity data may provide information that is related to management of a health condition, such as diabetic health (e.g., control of glucose concentration levels.) In some examples, the low-fidelity data may provide information that indirectly relates to diabetic health. The low-fidelity data may, for example, be activity data (e.g., from a smartwatch or other wearable sensor), which may indicate the amount of exercise or movement by a patient. The activity data may be accurate with respect to activity level, but may be considered low-fidelity in the sense that it does not provide a high degree of precision about the condition of a patient from a glucose management or diabetic condition management perspective, for example because the low-fidelity data is indirectly related to glucose control or has a relatively weak correlation with glucose levels, compared to high-fidelity data. Low-fidelity data may additionally or alternatively include location, user-input, or other physiological data (e.g., heart rate or respiration.) In some examples, low-fidelity data may glucose concentration data, such as single-point glucose data (e.g., blood glucose meter data), glucose data from an NFC enabled sensor, optical glucose data, or glucose information collected with another technique. Low-fidelity data may also include test results, such as fasting glucose level, or hemoglobin A1C. The low-fidelity data may be used to conduct a diabetic health assessment or to provide guidance to a patient to improve or control their diabetic health condition.

Additional information may also be collected during low-fidelity data collection. For example, a system may collect information regarding use of an activity tracker, food tracker, or self-monitoring of blood glucose. Patient engagement may also be collected, such as level of engagement or success in coaching or goal-setting programs. Preference information may also be collected, such as a preferred method for viewing and reviewing health data (e.g. type and timing of app views, chats, and coaching calls, or a style of learning (e.g. reviewing patterns versus real-time tracking and interaction), or a preferred graphical style (e.g., analyzing user interface screen views for examples of specific types of details examined, or a preference for qualitative versus quantitative viewing), or a communication style (short messaging versus videos or reading), or a preferred health metric (e.g. number of steps, exercise streaks, daily carbs, current app configuration). One or more goals may also be determined (e.g. meals choices, exercise, basal or drug titration, or hypo avoidance). A risk metric for the patient may also be determined, for example based upon demographics, medical records, average or fasting glucose levels or post-meal glucose excursion characteristics. In some examples, a patient may be assigned to a goal or risk metric based at least in part on a cohort of previous subjects that had similar starting situations, goals, or characteristics.

At 410, high-fidelity data may be collected. During high-fidelity data collection, low-fidelity data collection may be suspended, or both low-fidelity and high-fidelity data may be collected. The high-fidelity data may provide information that is highly related to management of a patient health condition. For example, the high-fidelity data may be data from a continuous glucose monitor. High-fidelity data may be more expensive, burdensome, or invasive to collect than low-fidelity data, so it may be necessary to determine a justification for the collection of high-fidelity data.

In an example, a determination that the high-fidelity data collection is needed, or otherwise justified, based at least in part upon low-fidelity data. For example, low-fidelity information may be used to determine or identify subjects that are likely to gain health benefits by transitioning to intermittent or continuous high-fidelity data collection. Such a determination may be based, for example, on a risk metric as described above, or another assessment of a diabetes or cardiovascular risk, or an identification of glucose concentration patterns that may benefit from high-resolution information (e.g. high-resolution data for post-meal rise in glucose concentration, as well as peaks, and duration or glucose excursions, may be used to understand a meal's glycemic load and glycemic load), or an identification of a subject with significant meal-to-meal or day-to-day variation (e.g., high-fidelity (e.g., CGM and activity) could correlate glucose patterns with activity or sleep patterns). A determination to engage in high-fidelity monitoring may also be based on identification of a subjects with an upcoming medication change, or a subject making progress in a coaching plan, or a recommendation from a coach or other health care providers.

In some examples, a machine learning technique is used to determine whether high-fidelity data collection is needed or justified based at least in part on the low-fidelity data. Any suitable machine learning technique can be used such as, for example, a supervised learning model, an unsupervised learning model, and/or a reinforcement learning model.

According to a supervised learning technique, a model is trained using a set of labeled training data. In this example, labeled training data can include sets of low-fidelity data and labels indicating whether each set of low-fidelity data justifies high-fidelity data collection. A trained supervised learning model can receive low-fidelity data and generate an output indicating whether the received low-fidelity data indicates high-fidelity data collection is needed or justified. Example supervised learning models that can be used include classification algorithms such as logistic regression algorithms, naive Bayes classifiers, support vector machines, decision tree algorithms, boosted tree algorithms, random forest algorithms, some neural networks, nearest neighbor algorithms, and so on.

According to an unsupervised learning technique, a model is generated using low-fidelity training data that may not be labeled. The model identifies instances of low-fidelity data that are similar to one another. The model can then be used to identify low-fidelity data that is similar to previous instances of low-fidelity data that needed or justified high-fidelity data collection. Examples of unsupervised learning algorithms that can be used include clustering algorithms, anomaly detection algorithms, latent variable models, and some neural networks.

According to a reinforcement learning technique, a reinforcement learning model can be provided with low-fidelity data and can make a determination of whether the low-fidelity data justifies high-fidelity data collection. The reinforcement learning model can bet provided with feedback indicating whether the determination is correct and can use the feedback to improve its performance. Example reinforcement learning models that can be used include Q-learning algorithms, Sarsa algorithms, Markov decision process algorithms, and so on.

A determination to initiate collection of high-fidelity data may be based at least in part on collection of information from an activity sensor worn on the patient. For example, the determination to initiate collection of high-fidelity data may be based upon satisfaction of an activity condition. For example, the activity condition may include evidence that a patient exhibits activity in excess of a threshold, or that the patient periodically participates in some kind of exercise (e.g., walking, running, or activity in excess of a specified baseline) on a sufficiently frequent basis). In other examples, a determination to initiate high-fidelity data collection may be based on blood glucose meter data (e.g., satisfaction of a blood glucose condition, such as determinization that an average blood glucose level exceeds a threshold, or a specified number of glucose readings over a threshold) or location (e.g., frequent visits to an exercise facility or an unhealthy restaurant). A determination may also be based on a combination of two or more types of low-fidelity data. For example, activity and blood glucose meter data may be used in combination, or activity and location may be used in combination, or blood glucose meter data and location may be used in combination. In an example, a determination that blood glucose levels (as determined for example by a blood glucose meter) respond to a secondary factor such as activity (e.g., activity reduces blood glucose levels) or a location (e.g., blood glucose levels fall or are more controlled after a visit to a park or gym, or blood glucose levels rise or are less controlled after a visit to fast food restaurant.)

A characteristic of the high-fidelity data collection 410 may be based at least in part on the low-fidelity data collection. For example, a system may estimate a duration or schedule (e.g., intermittent period) for high-fidelity monitoring and may initiate shipment of required supplies (e.g., a CGM sensor) according to the schedule, or determine a quantity for shipment (e.g., how many CGM sensors to ship). In some examples, a high-fidelity system (e.g., CGM system) may be preconfigured, based at least in part on low-fidelity data, to match a subject's needs. For example, one or more preferred metrics for a current health goal or goals may be selected or ranked, or a system may automatically reconfigure a coaching system (e.g., a chat bot or other coaching application running on a smart device, such as a watch) with preferred or specified information, such as enhanced glucose metrics. In some examples, a system may integrate enhanced glucose metrics (e.g. meal metrics) to one or more specified (e.g., most viewed) application screens or devices (e.g. display on a watch). A system may inform a patient management facilitator, such as a human coach or a chat bot, about patient-management related information, such as when high-fidelity data is available, or specified metrics to highlight for a subject. A system may also determine guidance or other patient management factors based on behavioral learnings about a subject, such as timing and types of messaging, such as delivery of information about a post-meal recap (e.g., extent or nature of glucose level control or loss of control), an exercise benefit, an improvement with medicine changes, or adherence, or to conduct an information-gathering period. A system may also determine a goal (e.g., target for time-in-range) based upon low-fidelity data. Any of the guidance examples described above or below may be employed in the method 401.

Figure 5:
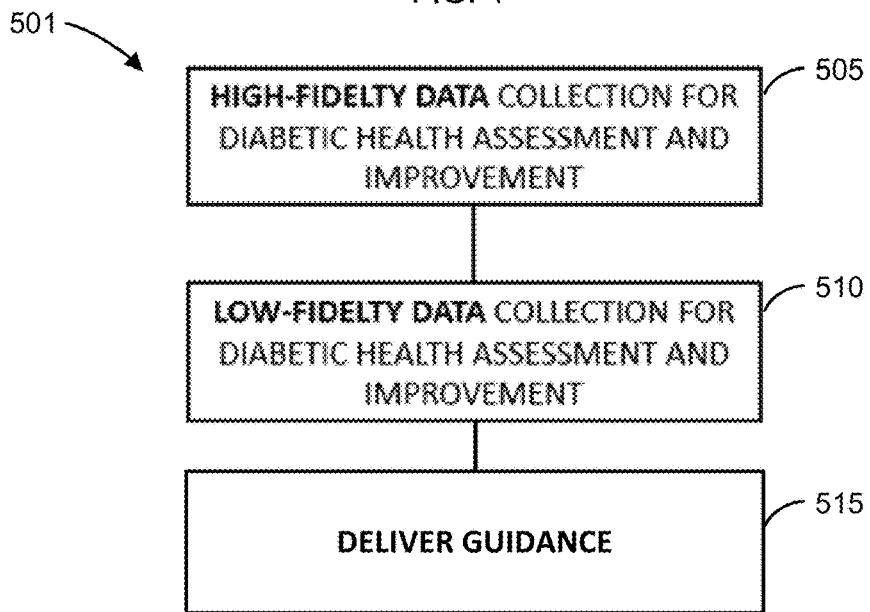
FIG. 5 is a flowchart illustration of a method of collecting high-fidelity data and collecting low-fidelity data.

FIG. 5 is a flowchart illustration of a method 501 of collecting high-fidelity data and collecting low-fidelity data. At 505, high-fidelity may be collected. The high-fidelity data may be used for a diabetic health assessment or for improvement of diabetic health (e.g., to obtain better control of glucose concentration levels or patterns), or both. The high-fidelity data may be CGM data, or any of the other examples of high-fidelity data described above or below.

At 510, low-fidelity data may be collected for diabetic health assessment or improvement of diabetic health (or both). The low-fidelity data may be activity data, or any of the other examples of low-fidelity data described above or below. In some examples, the low-fidelity data collection may be based at least in part on the high-fidelity data collection. In some examples, an insight from high-fidelity data collection may be used to inform app functionality, graphic and phone apps. For example, a time to obtain low-fidelity data (e.g., check glucose level using a meter) may be determined, for example to capture high or low glucose concentration values.

In some examples, at 515 guidance may be delivered to the patient to improve diabetic health. For example, a subject (e.g., patient) may be educated or reminded about the importance of exercise or dietary choices, or a patient may be congratulated or otherwise recognized for an achievement such as an exercise goal or glucose control condition (e.g., maintain a glucose level in a specified range.) Patient guidance may be based in part on the high-fidelity data. For example, a patient may be informed that glucose levels tend to rise or fall, or tend to rise or fall a certain amount, at a particular time of day (e.g., a glucose level may tend rise in the morning) or around the time of a particular event (e.g., a glucose level may peak a certain amount of time after a meal.)

In some examples, high-fidelity data collection stage may personalize metrics, guidance or other information relating to management of a physiologic condition of a patient, such as glycemic health. For example, an insight based on high-fidelity monitoring may be used to inform app functionality, graphic or a smart device application. In some examples, health concepts (e.g., potential guidance or action to be taken by a subject may be ranked or quantified for potential health impact, a list of patient management options may be formed into a personalized list for a subject, e.g., by determination of one or more estimates of a quantifiable benefit on a physiological outcome (e.g., achievement of a glucose concentration range, goal, time-in-range, or A1C.) For example, one or more patterns (e.g., dietary choice, exercise or activity, or sleep) that result in a benefit (e.g., better glucose control) may be determined based at least in part on high-fidelity data. In some examples, a correlation may be determined between a glucose concentration level and one or more lifestyle factors (e.g., activity (e.g., steps), meal timing, or food choice.)

Guidance may be based on a correlation determined at least in part from high-fidelity data, such as a correlation between glycemic health and another measurable feature or pattern. For example, guidance may be based on a correlation with exercise and activity amount and intensity with glucose improvements (e.g. how many minutes or steps were shown to reduce glucose by 20 mg/dL), or a correlation with food and dietary choices and glucose improvements (e.g. which foods caused large glucose spikes).

In some examples, a glucose metric, glucose excursion (e.g., deviation from a desired range) or glucose profile (e.g., glucose concentration pattern) may be determined from low-fidelity data and previously-collected high-fidelity data (e.g., using a correlation between the low-fidelity data and high-fidelity data).

The use of high-fidelity data as described can increase the performance of devices that measure and/or utilize low-fidelity data. For example, low-fidelity data alone may be used to provide generalized guidance to a user, for example, by comparing activity levels or other low-fidelity data to generalized guidelines or standards. Using high-fidelity data in conjunction with low-fidelity data, as described herein, can allow the devices to provide user guidance that is tailored to the individual user and, therefore, more likely to provide meaningful results, such as achievement of a glucose concentration range, goal, time-in-range, or A1C.

Figure 6:
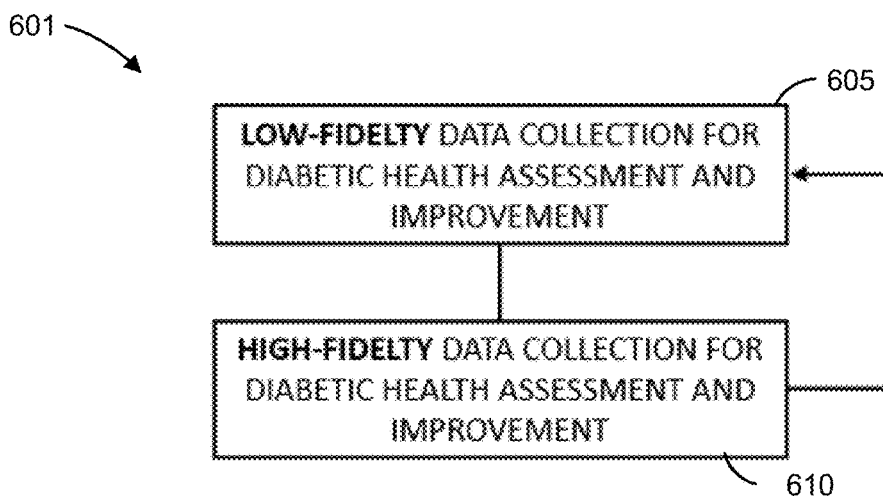
FIG. 6 is a flowchart illustration of a method of collecting low-fidelity data and intermittently collected high-fidelity data.

FIG. 6 is a flowchart illustration of a method 601 of collecting low-fidelity data and intermittently collected high-fidelity data. At 605, low-fidelity data is collected. The low-fidelity data may be activity, blood glucose meter data, or any of the low-fidelity examples identified above or below.

At 610, high-fidelity data is collected. During a period in which high-fidelity data is collected, collection of low-fidelity data may continue, or collection of low-fidelity data may be suspended. Preferably, collection of low-fidelity continues during for at least a portion of the high-fidelity data collection period, so that both high and low-fidelity data are collected during an overlapping period. A relationship (e.g., correlation) between low-fidelity data and high-fidelity data may be determined from data collected during the overlapping period. For example, the relationship between low-fidelity data and high-fidelity data can be found using a machine learning technique, such as, for example, the techniques described herein.

The method may return to low-fidelity data collection 605 during a subsequent low-fidelity data collection period, during which time guidance for a patient may be determined based upon the low-fidelity data and a determined relationship between the high-fidelity data and the low-fidelity data. In some examples, the low-fidelity data may be used as a surrogate for the high-fidelity data in determining patient guidance. The process may cycle between a low-fidelity collection period at 605 and a high-fidelity collection period at 610, so that high-fidelity data is intermittently collected. The intermittent high-fidelity data may be used to refine or update (e.g., recalibrate) a determined relationship between the high-fidelity data and low-fidelity data. In some examples, the process may return to high-fidelity collection at 610 responsive to a detected or reported change in health (e.g., a change in glucose concentration levels, weight, activity, or a new diagnosis.) In some examples, high-fidelity data is collected periodically (e.g., once a quarter, once a year, etc.). Upon the collection of a new set of high-fidelity data, the relationship or correlation between low-fidelity data and high-fidelity data can be updated and patient guidance revised.

Figure 7:
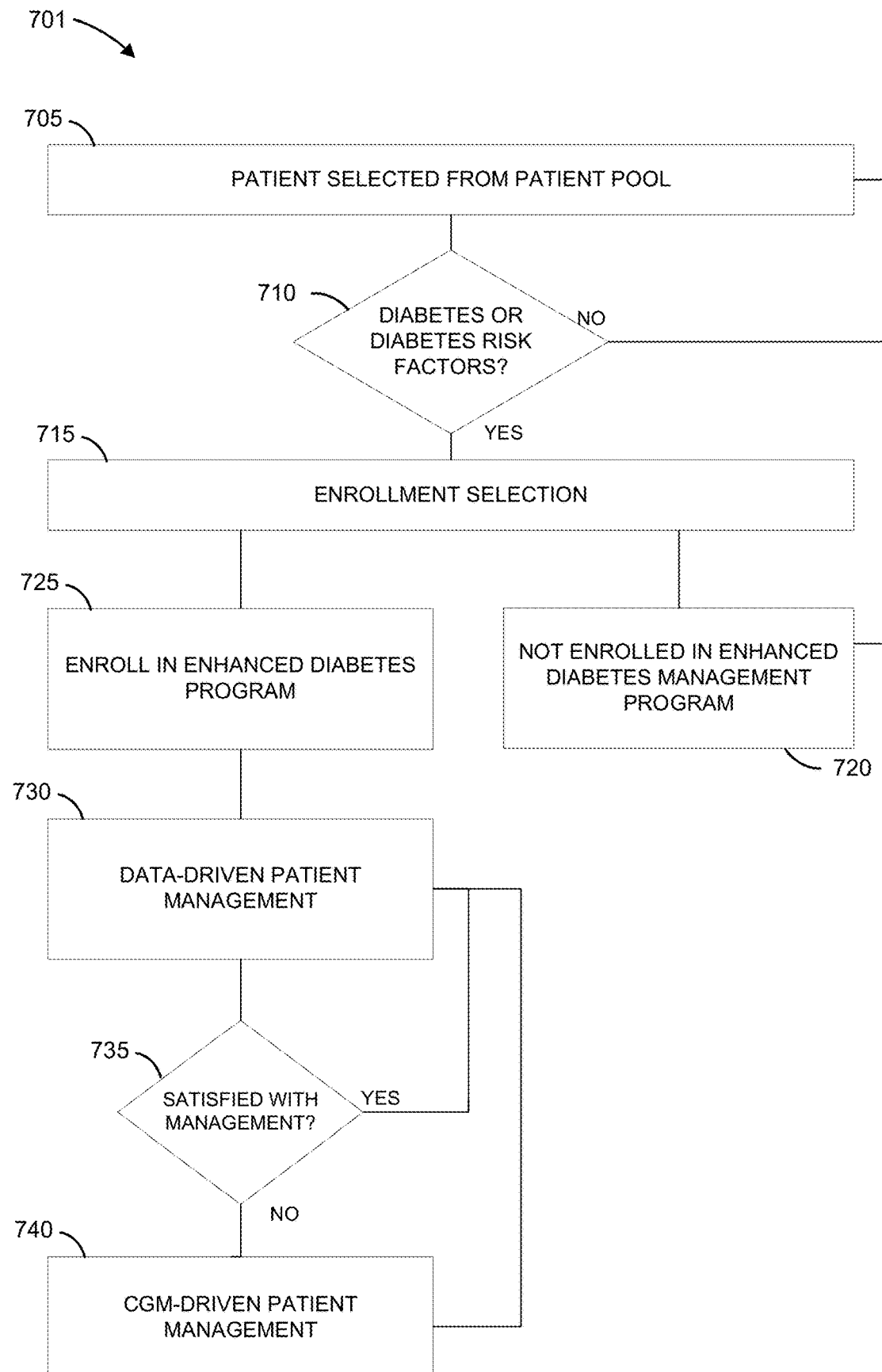
FIG. 7 is a flowchart illustration of a method of managing a patient condition.

FIG. 7 is a flowchart illustration of a method 701 of managing a patient condition. At 705 a patient is identified for screening from a patient pool. The patient pool may, for example, include a group of patients at a clinical practice, or in a specified insurance pool or program, or in a geographic location, or at a workplace, or any combination thereof. For example, a pool of 100, 10,000, or 100,000 patients may be identified.

At 710, the patient's condition or health history is evaluated for diabetes or diabetes risk factors. For example, the patient's weight, body mass index, family history, genetic markers, prescription history (e.g., prescribed medications), medical history (e.g., diagnosis of type 2 diabetes or another metabolic disease, which may be determined for example from electronic health record codes or other data) test results (e.g., A1C, fasting glucose level, oral glucose tolerance), other metabolic diseases, or other factors may be evaluated to identify a potential for diabetes, prediabetes, or risk factors that may indicate a vulnerability to development of diabetes. Exclusion criteria may also be applied, such as a type 1 diabetes diagnosis, or type 2 diagnosis with intensive insulin therapy. In some examples, the screening may generate a simple yes/no output. In some examples, a subset of 10% of patients in the pool (e.g., 10,000 out of 100,000) may be identified as candidates for enrollment in an enhanced diabetes management program. In other examples, more granular output may be provides, such as a classification as type 1 diabetes, type 2 diabetes, gestational diabetes, or a classification of type 2 diabetes in terms of disease progression or glycemic control (e.g., prediabetes, early type 2, or full type 2), or quantification of disease progression (e.g., on a scale of 0 (normal glucose tolerance) to 9 (persistent uncontrolled hypoglycemia or hyperglycemia.)

At 715, an enrollment selection is performed to determine whether the patient will be enrolled in a diabetes management program. An enrollment selection may occur, for example, in response to satisfaction of an enrollment condition, which may be based upon additional screening input, an additional review of current or previous medications, diabetes progression, effectiveness of previous treatments, predicted disease progression, adherence or participation in previous health promotion programs (e.g., exercise or medication compliance), or any of the factors described above (weight, BMI, family history, etc.). In some examples, a score or other prediction may be determined based on a future diabetes risk or a cost if the patient were to continue on a current diabetes management program. Additionally, or alternatively, a score or other prediction may be determined based upon a calculated potential benefit or prediction of success of an enhanced diabetes program. In some examples, a weighted score may be determined based upon a combination of a potential health risk or cost (or both) and a potent benefit (e.g., cost savings or impact on patient heath). Based on the scores or other information described above, the enrollment selection may determine a patient assignment for enrollment at 725 in an enhanced diabetes patient management program or for continuation of a current diabetes management program at 720. The identification at 705, evaluation at 710, and enrollment selection at 715 may be performed by one or more decision systems, such as execution of an algorithm on a computer system or mobile device, such as one or more of the devices shown in FIGS. 1 and 2. If the patient is not selected for enhanced diabetes management program at 720, the method returns to patient selection from the patient pool.

At 725, a patient may be enrolled in an enhanced diabetes management program. In an example, a diabetes management system may enroll the patient in the enhanced diabetes management program, e.g., in response to satisfaction of an enrollment condition. At 730, a data-driven patient management process may be performed. For example, data such as activity (e.g., using a wearable device), blood glucose meter data, user-input data (e.g., food or drink selection), location, or physiological data (e.g., heart rate or respiration) may be used to determine guidance for a patient regarding management of their physiologic condition. Activity data measured by a wearable device can include, for example, data captured using an accelerometer of other motion sensor associated with the wearable device. The guidance may, for example, educate or remind a patient about exercise or dietary selection, or may congratulate or otherwise recognize a patient for an achievement (e.g., completion of exercise, or exercising on a specified number of consecutive days, or a specified number of days in a time period (e.g. three times per week or 10 times per month), or congratulate or otherwise acknowledge a positive dietary choice (e.g., selection of a healthy meal or a restriction of caloric intake.) In some examples, the enhanced diabetes management may include collection and correlation of low-fidelity and high-fidelity data, such as described above in reference to FIG. 4, 5, or 6 and described below in reference to FIGS. 8B and 8C.

At 735, a determination is made as to the data-driven patient management. For example, the determination may be based on satisfaction of a diabetes management condition. The diabetes management condition may, for example, be based on one or more of an amount (e.g., percentage) of time that a blood glucose (e.g., as determined by a blood glucose meter) is in a target range (e.g., 70-160 mg/dL), a level of glycated hemoglobin or hemoglobin A1c in the blood (e.g., A1C test result), other diagnostic tests, a change in BMI, weight, or body composition (e.g., body fat percentage), cardiovascular health, or other factors or diagnostic tests. The determination may be made, for example, by a computer system that is configured to determine from collected data whether the diabetes management condition is satisfied. In some examples, the computer system may apply data inputs to a model, which may be based upon a particular patient, or a population. The model output may include a satisfaction state (e.g., satisfied or not satisfied) or a prediction about a future health state (e.g., patient health likely to improve, or patient health likely to be steady, or patient health likely to deteriorate.)

If the diabetes management condition is satisfied, the method may return to data-driven patient management at 730, and a system may continue with a previous patient management scheme, or may implement an improvement (e.g., more frequent data collection or more aggressive guidance), which may be based upon the determination at 735 or information used in making the determination.

If the diabetes management condition is not satisfied at 735, the process may progress to a stronger patient management scheme at 740. For example, the process may begin collecting or receiving continuous glucose monitoring information. For example, information from a continuous glucose monitor on a patient may be used to determine patient guidance. The CGM data may be combined with other sources of data to determine guidance. In some examples, the CGM-driven patient management scheme may use intermittent CGM data. For example, CGM data may be collected during a first period, and data collected during the first period may be used (optionally in combination with other non-CGM data) to determine guidance for a patient for a second time period in which CGM data is not available. In some examples, the CGM-driven patient management may include an ongoing cycle of intermittent CGM usage, such as implementing CGM data collection for a specified number of times per a specified time period (e.g., one week or ten days or two weeks per month, per quarter, or per year.) Intermittent CGM usage may reduce the cost of managing the patient. For example, intermittent CGM usage may be less expensive than non-intermittent (e.g., continuous) use of a CGM, because intermittent CGM data collection requires fewer sensors and only intermittent monitoring service via a CGM server. Intermittent CGM usage may also reduce the cost of managing the patient, compared to no CGM usage, by providing additional insights on management of glucose concentration levels for the patient and slowing or stopping the progression into Type 2 diabetes, which may both reduce overall health care expenses and improve the outcome (e.g., improve health) for the patient.

In some examples, after a period of CGM-driven patient management, the process may return to data-driven patient management at 730, at which point the collection of CGM data may be stopped, and the patient may be managed based upon non-CGM information. Information collected during the CGM-driven patient management 740 may be used to manage the patient (e.g., to determine guidance for the patient) during the data-driven patient management 730 in which CGM data is not available. For example, a relationship (e.g., correlation) between CGM information and non-CGM information may be used to infer an estimated glucose concentration level or range from non-CGM data.

In various examples, all of the steps in the process may be performed by a patient management system, which may collect, store, and analyze data about a patient. In some examples, data-driven patient management 730 may include collection of low-fidelity data, and the second stage of patient management 740 may include collection of high-fidelity data. While CGM data is provided as an example, it is understood that other sources of high-fidelity data may also be used, and that the example method may also be adapted to management of other diseases in addition to or instead of managing a diabetes or pre-diabetes condition.

Figure 8A:
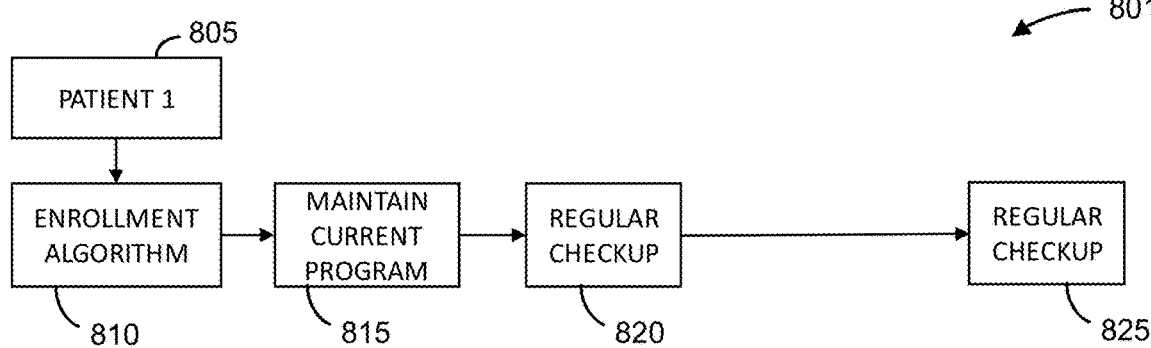
FIG. 8A-8C are flowchart illustration of example processes of management of a patient.

FIG. 8A is a flowchart illustration of a process 801 of management of a first patient. At 805, Patient 1 is selected. At 810, an enrollment determination is made, for example by application of an enrollment algorithm by a computer system, which may use health data as described above (e.g., height, weight, body mass index, blood glucose levels). At 815, a determination is made to maintain a current patient management program, which may for example include periodic testing and delivery of guidance at regular checkups, without ongoing data collection between checkups. The regular checkup may be a doctor's office visit or may be an electronic checkup based upon known or periodically (e.g., semi-annually or annually) collected information about the patient. In some examples, each of the steps in the management of Patient 1 may be conducted by a patient management system, which may receive or collect information about the patient and make one or more determinations based on patient data (e.g., apply an algorithm or apply data to a model).

Figure 8B:
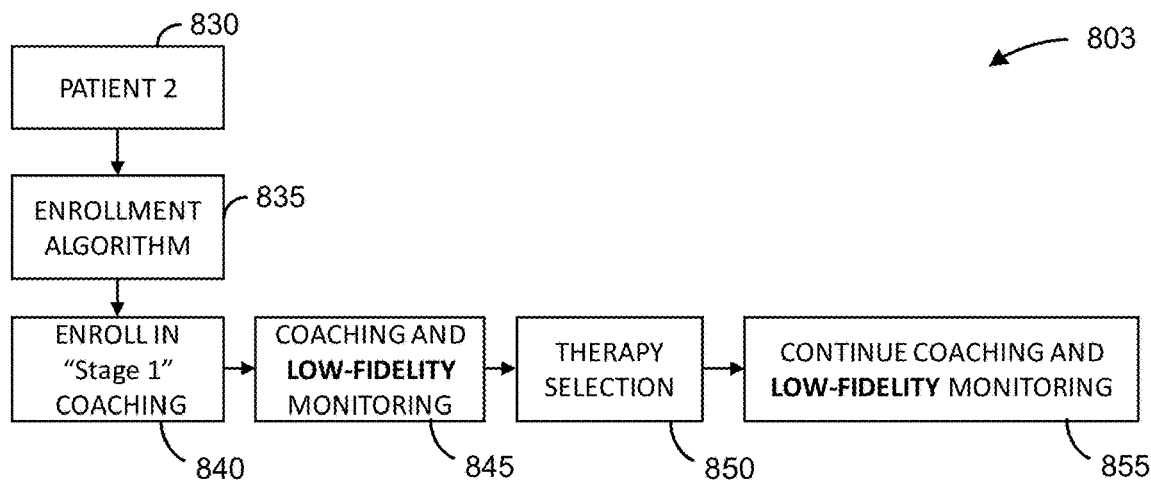

FIG. 8B is a flowchart illustration of an example process 803 of management of a second patient. At 830, Patient 2 is selected for evaluation. At 835, an enrollment determination is made, for example by application of an enrollment algorithm by a computer system, which may use health data as described above (e.g., height, weight, body mass index, blood glucose levels). At 840, Patient 2 is enrolled in a stage 1 coaching scheme in which, for example, guidance may be provided to the patient, e.g., via a handheld device or watch, based on low-fidelity data. For example, a chat bot functionality, as described herein, can be used to provide guidance to the patient. At 845, low-fidelity data is collected, and coaching or other guidance is determined based at least in part on the low-fidelity data. At 850, a therapy selection is made. The therapy selection 850 may be based at least in part on the low-fidelity data. The therapy may, for example, include initiation of a therapy, such as insulin delivery (e.g., via a smart insulin pen) or initiation of an oral medication. In some examples, the therapy selection may include guidance to deliver a specific bolus of medication (e.g., consider an insulin injection now) or to partake in an activity (e.g., take a walk or run to lower your glucose level.) At 855, low-fidelity monitoring and coaching is continued for Patient 2.

Figure 8C:
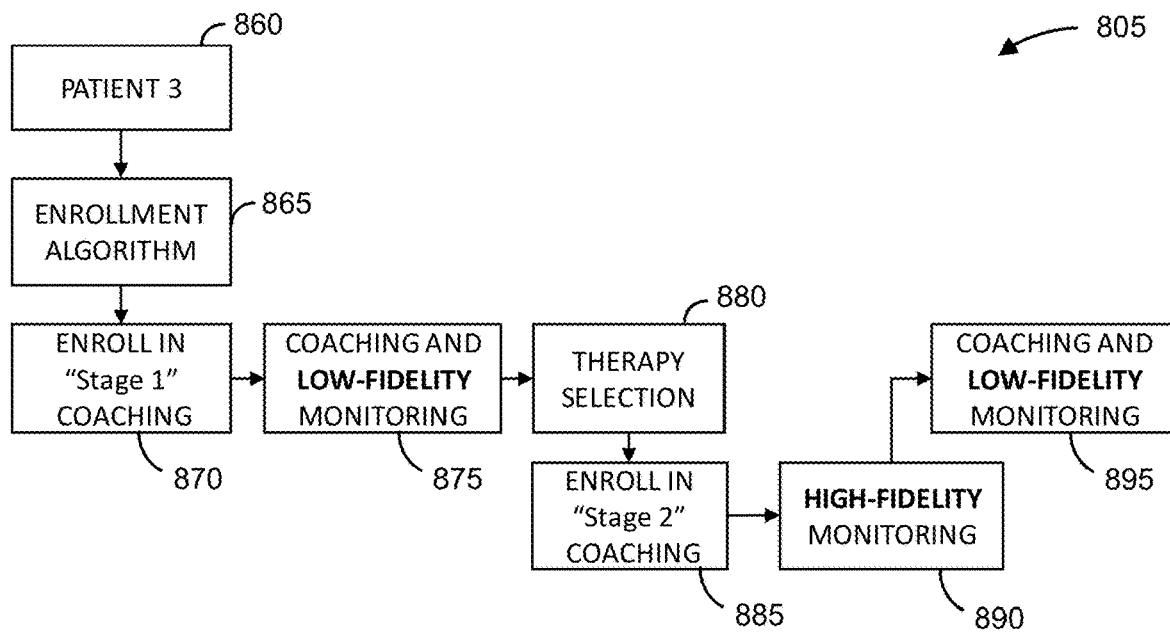

FIG. 8C is a flowchart illustration of an example process 805 of management of a third patient. At 860, Patient 3 is selected for evaluation. At 865, an enrollment determination is made, for example by application of an enrollment algorithm by a computer system, which may use health data as described above (e.g., height, weight, body mass index, blood glucose levels). At 870, Patient 3 is enrolled in a stage 1 coaching scheme in which guidance may be provided to the patient, e.g., via a handheld device or watch. At 875, low-fidelity data is collected for Patient 3, and coaching or other guidance for Patient 3 is determined based at least in part on the low-fidelity data. The coaching and/or other guidance can be provided to Patient 3 via the hand-held device 112, for example, utilizing a chat bot, video, animation, or other user interface mode. At 880, a therapy selection is made. The therapy selection 880 may be based at least in part on the low-fidelity data. The therapy selection may be an initiation of a therapy such as an insulin injection program or oral medication. The therapy selection may in some cases be a determination to engage the patient in a stage 2 coaching scheme that may be based at least in part on collected high-fidelity data (e.g., CGM data) regarding the patient. For example, the factors or process steps described above in reference to FIG. 4 may be applied in the low-fidelity monitoring 875 or therapy selection 880.

At 885, the patient may be enrolled in the stage 2 coaching program. At 890, high-fidelity monitoring may be performed. For example, CGM data may be received or collected. In some examples, high-fidelity data may be analyzed to determine whether the data satisfies a condition (e.g., statistical metric) for correlation or identification of a pattern or one or more correlations. In some examples, a machine learning technique may be used, as described herein. At 895, low-fidelity monitoring may be performed, and coaching or other guidance may be delivered to a patient (e.g., via an interface on a user device such as smart phone or watch.) In some examples, the guidance at 895 may be based at least in part on high-fidelity data (e.g., CGM data) collected during a high-fidelity data collection period or based on a relationship between high-fidelity data and low-fidelity data.

Figure 9:
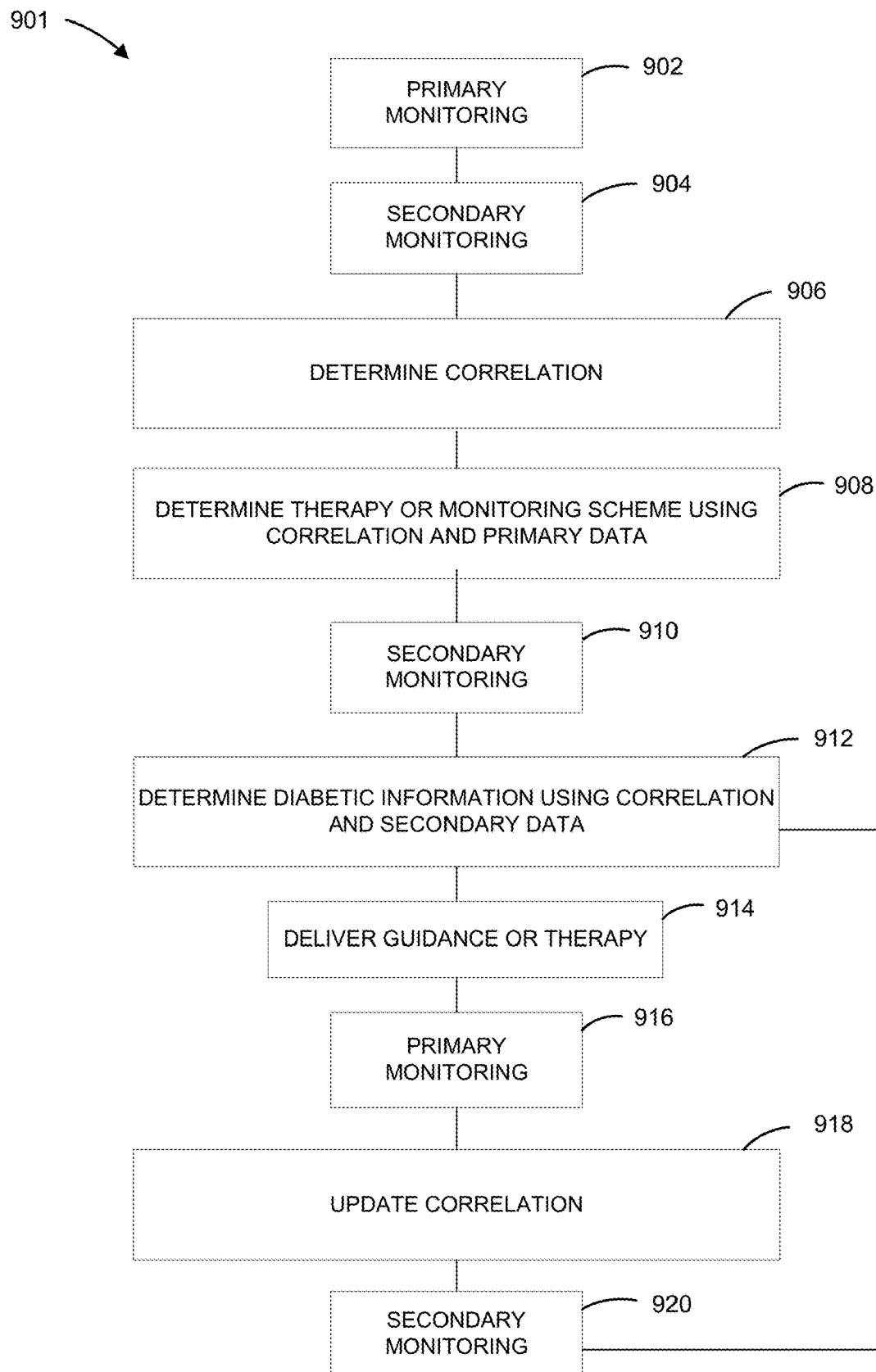
FIG. 9 is a flowchart illustration of a process for monitoring a patient using a primary monitoring technique and a secondary monitoring technique.

FIG. 9 is a flowchart illustration of a process for monitoring a patient using a primary monitoring technique and a secondary monitoring technique. The primary technique may include receipt or collection of a first type of data ("primary data" or "first data"), and the secondary technique may include receipt or collection of a second type of data ("secondary data" or "second data"). For example, the primary monitoring may include collection or receipt of high-fidelity information about a patient and the secondary monitoring may include collection or receipt of low-fidelity information about the patient. In an example where the patient is a diabetic patient, the primary technique may, for example, include continuous glucose monitoring. The secondary technique may, for example, include receipt or collection of activity information, location information, user input information, or glucose concentration information (e.g., single-point glucose data such as blood glucose meter data, glucose data from an NFC enabled sensor, optical glucose data, or glucose information collected with another technique).

At 902, primary monitoring is performed to collect first data of a first type during a primary monitoring period. In some examples, the monitoring may include receiving the first data from a sensor system, such as a continuous glucose monitoring system. In some examples, the monitoring may include receiving a sensor signal from a sensor circuit and processing the sensor signal to generate at least a portion of the first data.

At 904, secondary monitoring is performed to collect second data of a second type during a secondary monitoring period. The secondary monitoring period may overlap, in an overlapping time period, with all or a portion of the primary monitoring period. In some examples, the monitoring may include receiving the second data from a second sensor system. In some examples, the secondary monitoring may include receiving a sensor signal from a sensor and processing the sensor signal to generate at least a portion of the second data.

In some examples, the secondary monitoring may include monitoring activity using a wearable fitness tracker. The wearable fitness tracker may include, for example, a wearable heart rate monitor, a wearable activity monitor, a smart phone, smart glasses, or a smart watch.

In some examples, the second data may include user input data. For example, the user input data may include medicament data, meal data, exercise data, sleep data, or any combination thereof.

In some examples, the first data may include an estimated glucose concentration level, and the data of the second type may include one or more detected physiologic signals, such as heart rate, oxygen concentration, skin tone, moisture content on skin, activity, activity pattern, blood ketone concentration level, urine ketone concentration level, respiration.

At 906, a correlation between the first data and the second data is determined. The correlation may be a positive correlation, or a negative correlation. The correlation may be determined, for example, by determining a pattern or relationship between a plurality of data points in the first data and a plurality of data points in the second data that corresponds to the first data (e.g., corresponding to the same point in time, or time-shifted such to recognize a change in the first data after a change or event in the second data, or time-shifted such to recognize a change in the second data after a change or event in the first data.) In various examples, the correlation may be calculated, e.g., using a processor and data retrieved from storage in a memory circuit. In some examples, the correlation may be determined using a processor by retrieving stored data from memory and using a machine learning technique based upon at least some of the stored data. In some examples, determining a correlation may include determining a relationship between the obtained first and the second data at corresponding times of day and/or days of the week within the overlapping time period. For example, a processor may determine from stored data that a glucose concentration level tends to trend high (e.g., over 150 mg/dL during morning hours (e.g., 7-10 AM or for three hours after waking), but that the glucose concentration does not trend high, or trends less high (e.g. glucose concentration under 126 mg/DL), on days where a patient takes an early morning walk.

In some examples, a correlation is based on multiple types of secondary data. For example, a model may be learned to determine a relationship between activity, heart rate, and estimated glucose concentration level (e.g., as determined using a CGM system).

In some examples, the method may include, at 908, determining a therapy or a monitoring scheme using the correlation and the primary data. For example, the secondary data may include single-point glucose monitoring (e.g., a blood glucose meter reading), and the method may include calculating, based at least in part on the primary data, a time window (e.g., optimal window or recommended window) to take a single-point glucose measurement. In some examples, obtaining one or more well-timed single-point glucose measurements may allow for an accurate determination of one or more estimated glucose concentration levels (e.g. a specific level or a range) between measurements, e.g., based on or more of: an interpolation technique, the determined correlation, additional types of secondary data (e.g., heart rate or activity), or any combination thereof. In some examples, the method may include determining a time window for obtaining or using non-glucose information, such as activity information, heart rate information, or user input. The method may further include prompting a user (e.g., patient) to obtain a measurement (e.g., check blood glucose with a blood glucose meter) or attach a sensor (e.g. put on a wearable activity monitor). The prompt may be delivered through a smart device such as a watch or handheld device.

At 910, the process may include an additional period of secondary monitoring. The secondary monitoring 910 may occur during a time period when primary monitoring is not occurring. The secondary monitoring may include obtaining a single-point glucose measurement (or other sensor information or user input) at a time determined in step 908.

At 912, the process may include determining diabetic information using the determined correlation (from step 906) and secondary data (from step 908.) In various examples, the diabetic information may include an estimated value for data of the first type at the subsequent time, a state of the patient, or a patient insight. The state of the patient or the patient insight may, for example, be related to a lifestyle modification relating to diet, exercise, glucose level monitoring, or medication. In some examples, the state of the patient or the patient insight may be related to mealtime management, exercise management, or sleep management.

In an example, when the primary data is an estimated glucose concentration level (e.g., from a CGM), an estimated glucose concentration level may be determined from the secondary data based on the determined (e.g., learned) relationship between the secondary data and the estimated glucose concentration level. In an example, the secondary data is or includes physiologic information (e.g., activity data, heart rate data), or both, and an estimated glucose concentration level or range (real time or average for a specified time period) is determined using the determined relationship and the physiologic information.

In some examples, the method may include intermittently monitoring the first type of data (e.g., CGM data) and determining diabetic information using the second data (e.g., activity or single-point blood glucose, or both) and the correlation during one or more periods of time when the first type of data is not available. For example, the monitoring 902 data of the first type may include continuous glucose monitoring, and the monitoring data 904 of the second type may include monitoring activity data with a wearable accelerometer. The wearable accelerometer may be configured to monitor data when the continuous glucose monitoring is not occurring.

At 914, the method may include delivering guidance or therapy. For example, the method may include displaying diabetic information about the patient on a user interface of a patient device, such as a handheld device, a watch, or on a display on wearable glasses. Displaying diabetic information may include, for example, displaying a recommended dietary modification or lifestyle modification on a user interface.

In some examples, the method may include at 914 administering a treatment based at least in part on the determined diabetic information. The treatment may include, for example, a pharmaceutical intervention, such as an oral medication or a medication delivered through a pump.

In some examples, the method may include primary monitoring during a third time period at 916.

At 918, the correlation may be updated based at least in part on primary data gathered during the primary monitoring during the third time period at 916. In some examples, the secondary monitoring step 910 may extend at least part way through the primary monitoring during the third period 916, and the correlation may be updated based upon the secondary monitoring 910 and the primary monitoring 916.

At 920, the method may include secondary monitoring 920 during a fourth time period. The method may return to step 912, and diabetic information may be determined using the updated correlation (from step 918) and the secondary monitoring data from step 920. The process may deliver guidance or therapy at 914, perform primary monitoring at 916, update the correlation at 918, again perform secondary monitoring 920, and return again to step 912, resulting in intermittent primary monitoring as the process cycles through the method steps.

In various examples, any of the steps in the method 901 may be omitted or combined with other steps. For example, step 912 may be omitted, or may be combined with step 910, or step 910 may occur after step 912.

Figure 10:
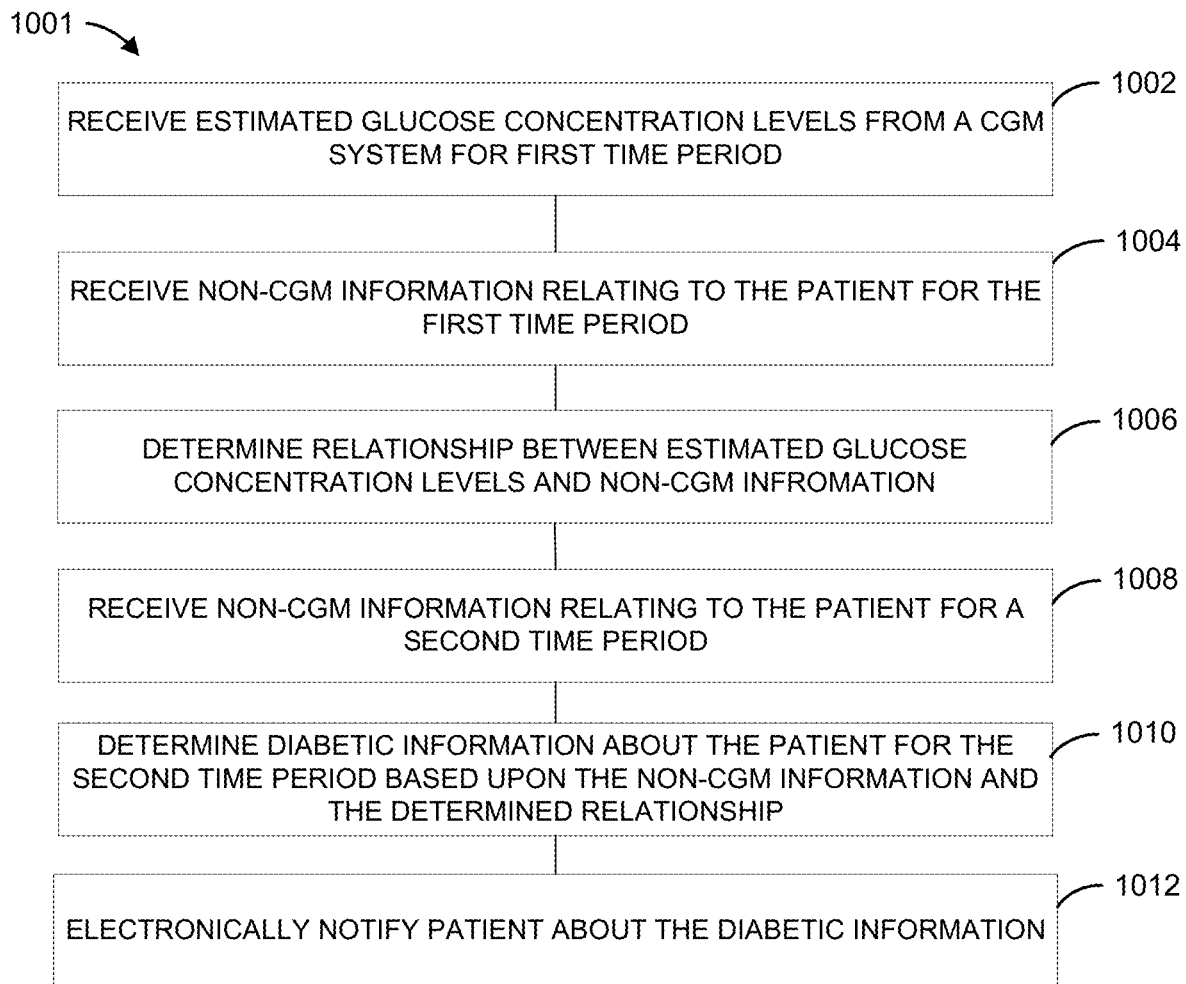
FIG. 10 is a flowchart illustration of an example method 1001 of determining and notifying a patient about diabetic information.

FIG. 10 is a flowchart illustration of an example method 1001 of determining and notifying a patient about diabetic information. The method 1001 may be executed on a system, such as the system 100 shown in FIG. 1. At 1002, an estimated glucose concentration level may be received from a continuous glucose monitoring (CGM) system for a first time period. The method may optionally include detecting the estimated glucose concentration level using a CGM sensor. The first time period may, for example, be a number of days (e.g., 7 days, 10 days, or 14 days) or weeks (e.g., four weeks or ten weeks). For example, a patient may be enrolled in a CGM study to gather information about the patient's response to various stimuli, such as oral medication, exercise, or activity.

At 1004, non-CGM information relating to the patient may be received for the first time period. The method may optionally include detecting the non-CGM information using a sensor. In some examples, the non-CGM information may include activity information, location information, or user input data. In some examples, the non-CGM information may include physiologic information about the patient. The physiologic information may, for example, include one or more of heart rate, respiration, oxygen concentration, skin tone, moisture content on the skin, activity, activity patterns, blood ketones, urine ketones, respiration, or acoustic information.

At 1006, a relationship between the estimated glucose concentration levels and the non-CGM information is determined. For example, a correlation may be calculated between the non-CGM information and the estimated glucose concentration levels. In some examples, a model may be learned from collected CGM and non-CGM data, such that an estimated glucose concentration level may be determined from non-CGM data by applying the non-CGM data to the model.

At 1008, non-CGM information relating to the patient for a second time period may be received. The second period may be a period in which estimated glucose concentration levels are not available from a CGM. At 1010, diabetic information about the patient for the second time period may be determined based upon the determined relationship and the non-CGM information. Determining diabetic information about the patient may include determining a patient state. Determining a patient state may include applying the non-CGM information to a model. In some examples, determining diabetic information may include determining an estimated glucose concentration level. For example, an algorithm may infer an estimated glucose concentration level from activity information that is calibrated to glucose concentration levels at an individual level (e.g., based on information about the patient) or at a population level, or both (e.g., using a predictive learning model.)

In some examples, determining diabetic information may include determining a qualitative rating, such as green, yellow, red, or "good control," "moderate control," poor control."

In some examples, determining diabetic information may include determining a quantitative metric. The quantitative metric may, for example, be an estimate of an amount or percentage of time that a glucose concentration level was in range during a specified time period. In some examples, a quantitative metric may not be available in real time. For example, a quantitative metric may include time-in-range for a specified period of time (e.g., a day, or a number of hours), which may be reported at the end of the day or intermittently, such as, for example, hourly, daily, weekly, etc.

At 1012, the system may electronically notify the patient about the diabetic information. For example, the system may present a notification (e.g., word(s) or symbol) on display of a hand-held device, smart watch, glasses, or other wearable electronic item, or the system may present a sound notification (e.g., verbal message or sound) or tactile notification (e.g., vibration) on a speaker of such a device. In examples in which a sound notification is used, the sound notification can be provided by a chat bot implemented, as described herein. In some examples, the notification is related to the severity of the diabetic information. Consider an example in which the non-CGM information is indicative of a hypoglycemic condition. The system may present a notification that is more severe to indicate urgency. For example, the system may present a high frequency or high duration sound, a verbal message presented at increased cadence or volume and/or a tactile notification of a high duration and/or amplitude. Consider another example, in which the non-CGM information is indicative of a normal or favorable blood glucose level. The system may present a notification that is less severe such as, for example, a lower frequency or lower duration sound, a verbal message presented at a reduced cadence or volume, and/or a tactile notification of a shorter duration and/or amplitude.

The system may improve patient management by, for example, managing the cost incurred by continuous glucose monitoring, or enabling glucose estimation to motivate a user (e.g. patient) to take steps to manage glucose levels. For example, utilizing low and high-frequency data in the manner described, by example, with respect to the example method 1001, can provide the benefits of high-fidelity data collection at reduced cost. For example, because the performance of the system during low-fidelity data collection may be comparable to the performance during high-fidelity data collection, it may not be necessary to perform higher-cost high-fidelity data collection as often. Also, glycemic control for the patient can be improved, for example, with the cost of full-time high-fidelity data collection.

Figure 11:
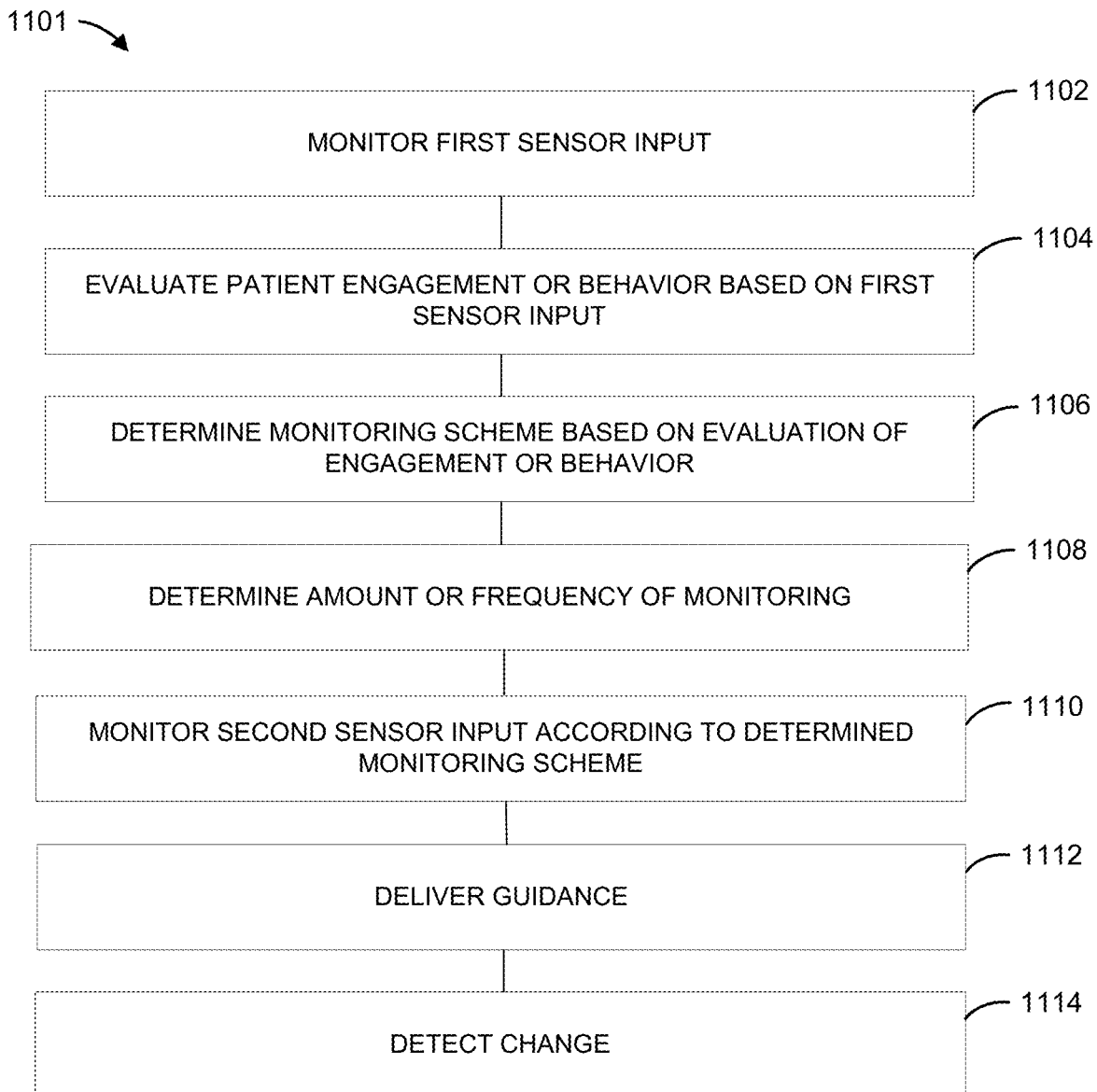
FIG. 11 is a flowchart illustration of an example method of determining a monitoring scheme based on collected sensor information.

FIG. 11 is a flowchart illustration of an example method of determining a monitoring scheme based on collected sensor information, which may for example indicate qualities about the engagement or behavior of a patient. For example, a decision to use CGM sensing, a CGM sensing parameter (e.g., a schedule or quantity of CGM sensing), a user interface parameter (e.g., type or content of guidance), or a goal (e.g., glucose target range or A1C target) may be determined based on activity data or other collected information.

The method 1101 may include, at 1102, monitoring a first sensor input to obtain first data of a first type. For example, the method 1101 may include monitoring patient data of a first type with a low-fidelity monitoring technique over a first time period. In various examples, the low-fidelity technique may include receiving user input data, such as medicament data, meal data, exercise or activity data, sleep data, or any combination thereof.

The monitoring of the first sensor input may include, for example, activity monitoring, single point blood glucose monitoring (e.g., monitoring using blood glucose meter information), optical glucose monitoring (e.g., using a watch with an optical sensor), or "blinded CGM" (e.g., continuous glucose monitoring where estimated glucose levels are not presented to a patient, e.g., glucose levels are transmitted to a server or stored in memory of a CGM or device local to the patient, for later analysis.) In some examples, monitoring the first sensor input may include activity monitoring by a wearable fitness tracker, such as a wearable heart rate monitor, activity monitor, smart phone, smart glasses, or smart watch.

The method 1101 may further include at 1104 evaluating patient engagement or behavior based on the monitored first type of patient data. For example, a remote system (e.g., server executing algorithms) or local system (e.g., handheld device) may evaluate a user's aptitude or preferences with respect to the complexity or number of features available on the user interface. A sophisticated or highly-engaged user may prefer a more complex or full-feature interface than a less-sophisticated or less-engaged user. Such a determination may be made, for example, based on the frequency of interactions with a device (e.g., handheld device or watch), timeliness of interactions, relevancy of interactions (e.g., responsiveness to alerts), compliance with guidance (e.g., partaking in exercise in response to guidance to do so), or interaction with another application (e.g., based on an interaction with a fitness tracker application.)

The method may include at 1106 determining a monitoring scheme based on an evaluation of patient engagement or behavior. For example, the method may include determining a hardware or software functionality of a device. The hardware or software functionality may, for example, correspond to operation of a user interface. In some examples, the determined functionality may include a simple or light-featured interface, which may be applied in response to identifying, as part of the evaluation, a low-engagement patient or a patient who may benefit from a less complex interaction. The determined functionality may also include a relatively complex or full-featured interface, which may be applied in response to identification of a highly-engaged user, or a user (e.g., sophisticated user) who may prefer a more complex interface (e.g., an interface that includes more features or provides more configuration options, such as programmable alerts or more frequent guidance.) In some examples, the user interface may additionally or alternatively adapt based at least in part on the age or date (e.g., year) of birth of a user. For example, the user interface may use larger fonts or user interface elements (e.g., buttons) or a different presentation scheme (e.g., more contrast or a specified color scheme) for older users. In some examples, a user interface may provide a visual challenge to ascertain whether a user has difficulty differentiating or selecting user interface elements or may prompt a user for information about visual acuity, and the user interface may adapt based on the response to the challenge or prompt.

In some examples, the determined hardware or software functionality may relate to a frequency (e.g., how often the device communicates with a user) or content (e.g., the subject matter of a communication to a user) of an automated coaching routine. For example, if a user is contacted too often, the user can become fatigued and may disengage. On the other hand, if a user is not contacted often enough, the user may not receive sufficient guidance to achieve desired results. The method 1101 can include correlating patient behaviors to different contact frequencies.

In some examples, determining the monitoring scheme may include determining a goal for a patient. The method may include determining a hardware or software functionality of a monitoring device (e.g., handheld device or body-worn device) related to or in furtherance of the goal. In various examples, the goal may include, a dietary goal, an exercise goal, a glucose level monitoring goal, or a medication goal. In some examples, the at least one hardware or software functionality of the monitoring device may relate to mealtime glucose management (e.g., strategies to manage glucose levels before, during, or after a meal, or any combination thereof, for example by exercising before or after a meal or delivery of insulin before a meal (a "pre-bolus" strategy). In some examples, the at least one hardware or software functionality of the monitoring device may relate to sleep management (e.g., strategies to control glucose levels during sleep or to avoid or minimize interruptions of sleep to address a glucose level problem).

In some examples, a goal for a patient may be determined at least in part based upon the first sensor input (e.g., data monitored with a low-fidelity monitoring technique.)

The method 1101 may further include, at 1108, determining an amount or frequency of monitoring. In some examples, the amount or frequency of subsequent data (e.g., second sensor input or high-fidelity data) may be determined based at least in part on the first sensor input, e.g., based on data collected by the low-fidelity monitoring technique. The amount or frequency of data may include a volume of data points, or a number of high-fidelity sensors to be used (e.g., number of CGM sensors to be sequentially or intermittently used to gather CGM data), or a periodicity (a consistent or irregular periods) between data collection events. The amount or frequency of subsequent data may also be based at least in part on a specified goal or result. For example, the amount or frequency of data may be calculated to increase or maximize a patient parameter, such as an amount or percentage of time in a specified range of glucose concentration levels, or a patient A1c level.

The method 1101 may include at 1110 monitoring a second sensor input according to the determined monitoring scheme. For example, the method may include monitoring, over a second time period, patient data of a second type with a high-fidelity monitoring technique using a monitoring device. The high-fidelity monitoring may, for example, include continuous glucose monitoring.

The method 1101 may further include, at 1112 providing a guidance to the patient, e.g., via the system 100 shown in FIG. 1. For example, the system may provide automated messages transmitted from a server to the monitoring device based on patient profile data or the first sensor input. In some examples, the guidance may be provided using a fitness tracker application, a meal tracking application, or a dedicated CGM or guidance application. For example, an application may deliver (e.g., display) CGM data, information based on CGM data (e.g., time-in-range), guidance for a subject (e.g., "consider an exercise session"), a predicted, estimated, or measured exercise benefit on glucose control. In some examples, an application may educate a user about food choices and resulting post-meal glucose control (e.g., excursions), or may educate a user or quantify a relationship between exercise and glucose-lowering effect of exercise. For example, the application may indicate that the user's selected activity is estimated to bring the user's glucose level to a desired value or range (e.g., "Your recent activity should bring your glucose level into a desired range."). In another example, the application may indicate that a suggested activity is likely to bring the user's glucose level to a desired value or range (e.g., "We estimate that one hour of running will lower your glucose by 15 mg/dl."). In some examples, guidance can be provided by chatbot functionality provided as described herein.

The method 1101 may further include, at 1114, detecting a change in a patient parameter (e.g., improvement in glucose concentration control at a specified time or in a specified condition, or an improvement in A1C.) The change may be measured between the first time period during which the first sensor input is collected, and the second time period during which the second sensor input is collected. The detected change may be used to further influence at least one hardware or software functionality of the monitoring device. In some examples, machine learning techniques can be used to relate characteristics of the monitoring or guidance scheme to changes in patient parameters. For example, a positive change may be correlated with a particular aspect of the monitoring scheme or guidance, and the hardware or software functionality of the monitoring device may be modified to emphasize the aspects that are correlated with the positive change. Such iterative changes may improve the performance of the monitoring system in guiding the patient to positive clinical outcomes or achievement of a management goal. (e.g., toward better controlled glucose levels or a lower A1c test results). In some examples, an indication of the increased or maximized patient parameter may be displayed on the monitoring device.

The method may be repeated to provide ongoing guidance for the patient. For example, after step 1114, the method may return to step 1102, 1106, or 1110. In some examples, one or more steps of the method may be omitted every time, or when the method is repeated.

In some examples, the method may include determining a patient end goal. The patient end goal may be based at least in part on the patient data of the first type or the patient data of the second type, or both. The method may further include displaying a therapy recommendation (e.g., displayed as guidance) calculated to cause a transition of a patient state towards the patient end goal.

Figure 12A:
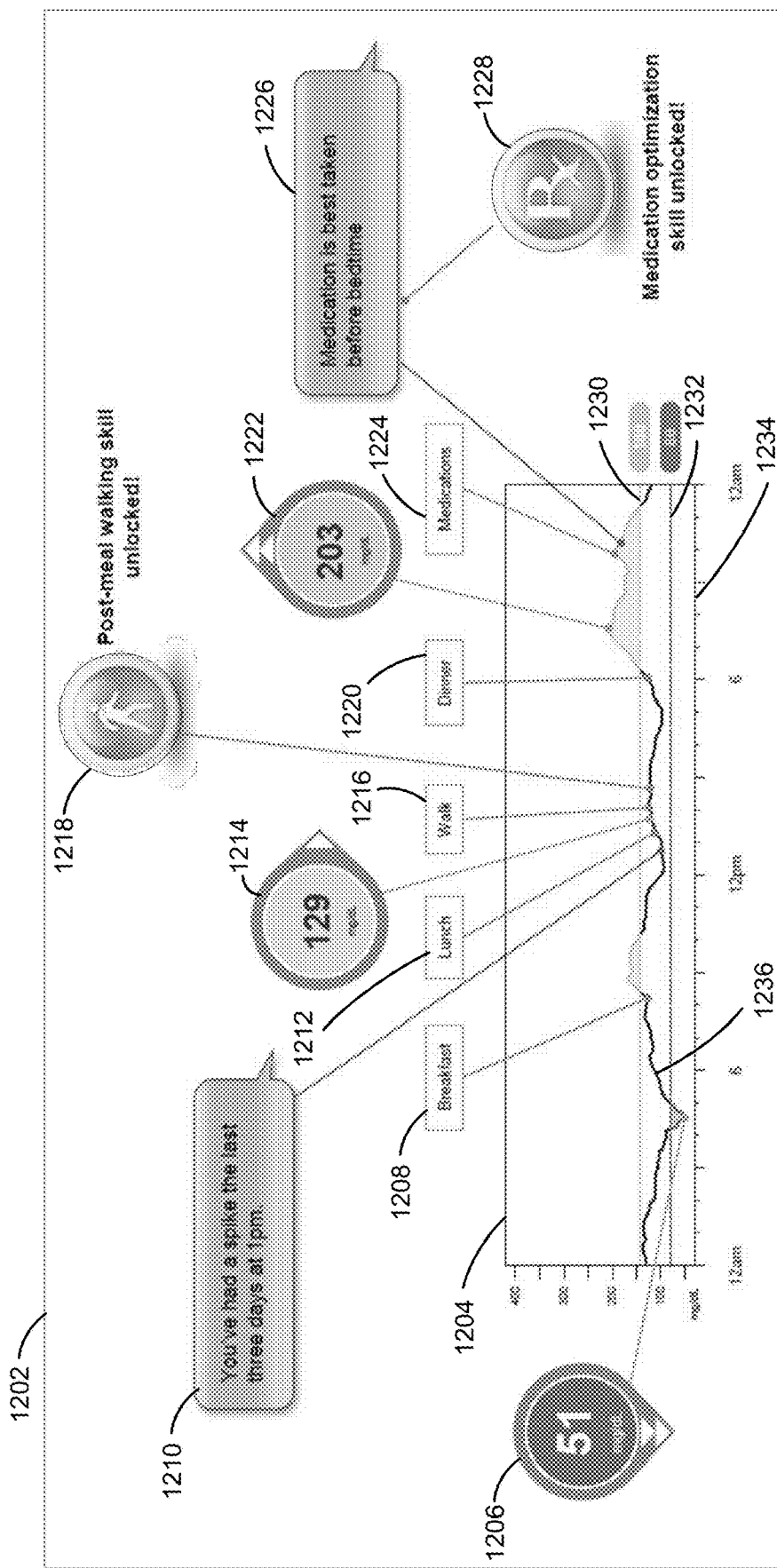
FIG. 12A is an illustration of an example user interface.

FIG. 12A is an illustration of an example user interface 1202, which may be presented on a user device, such as user device 132, or additionally or alternatively may be presented on hand-held smart device (e.g., smartphone) 112, tablet 114, computer 118, a wearable device 120, a peripheral medical device 122, or remote terminal 128.

Figure 12B:
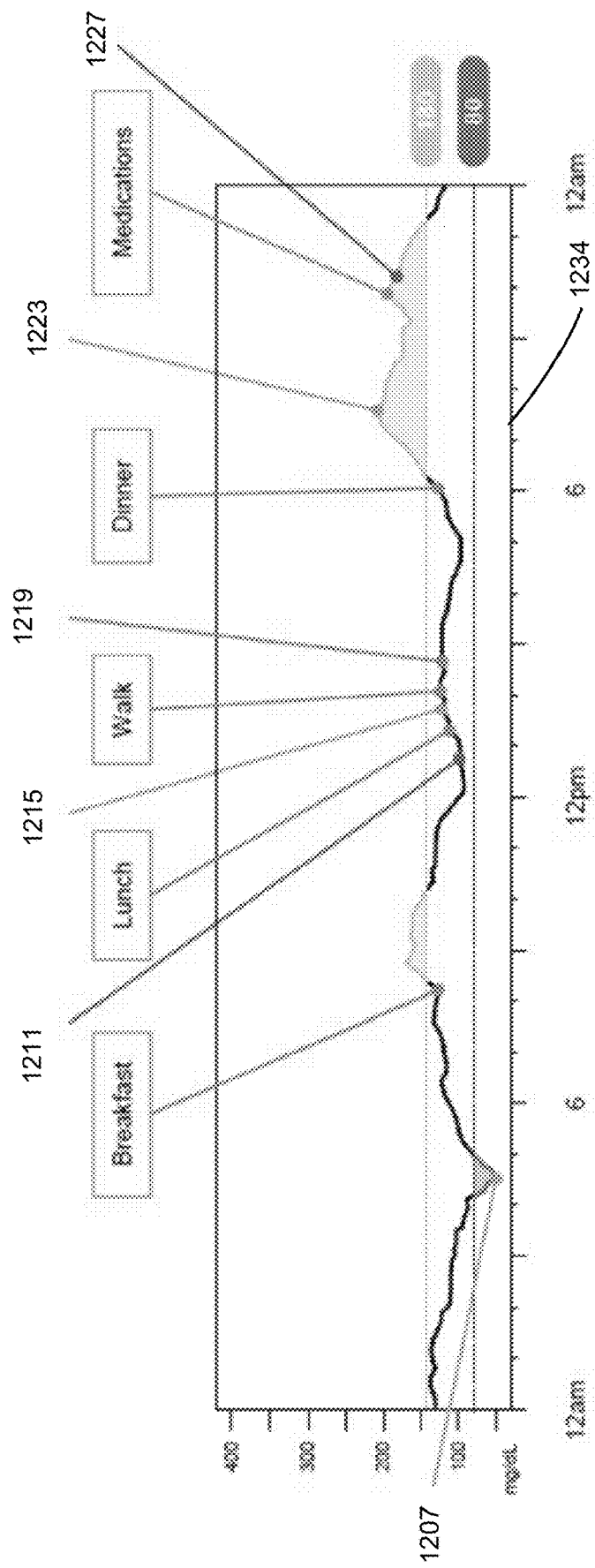
FIG. 12B is an enlarged view of a portion of the user interface shown in FIG. 12A.

The user interface 1202 may include a chart 1204, which may show glucose concentration levels 1236 (e.g., measured in mg/dL) plotted against a time axis 1234. The user interface 1202 may also show an upper bound 1230 and lower bound 1232 for a target range. In various examples, the target range may be set by a user (e.g. patient), or determined by a device or system (e.g., hand-held device 112 or 120 shown in FIG. 1), or may be provided by a coach (e.g., human coach or computerized "chat bot" coach.) In the illustrated example, the upper bound is set at 180 mg/dL and the lower bound is set at 80 mg/dL. In some examples, a range may be set (e.g., by a system or by default) for 70-160 mg/dL, and the range may be expanded (e.g., to 70-180 mg/dL) or contracted as is appropriate for a particular patient, which may be determined for example from a pattern of CGM or low-fidelity data or input from a user. An enlarged view of the chart is shown in FIG. 12B. In various examples, the glucose concentration level may be an estimated blood glucose concentration level (e.g., GCM data, or a level calculated based on other data), or the plotted glucose level may include blood glucose levels from a meter. The example chart 1204 shows a 24-hour time period (from 12 AM to 12 AM the next day), but, in various other examples, the chart may show shorter time periods (e.g., 1 hour, 3 hours, 6, hours, or 12 hours) or longer time periods (e.g., 2 days, 3 days, 1 week, 2 week, 1 month, or 3 months). For longer time periods, a plotted value may correspond to an average for a day or week, or the graph may show a range or distribution of values or averages (e.g., a bar showing high and low, and a point or line showing a median or mean.) While glucose concentration levels are shown, other types of analyte levels, or other types of sensor data may be shown instead of glucose concentration levels, or in addition to glucose concentration levels (e.g., on the same chart or on a different chart.)

The user interface 1202 may include a plurality of event indicators, which may show a physiological event, a meal event, an activity event, a medication event. For example, the user interface 1202 shows a glucose event 1206 around 4:30 AM, at which point the glucose concentration level reached a low point at 51 mg/dL with a steep downward trend indicated by two downward arrows. In some examples, especially where the user is known to be a heavy user of insulin, the event 1206 may correspond with an alert on a smart device (e.g., wearable device 120 or user device 132) to provoke a user to consume carbohydrates to avoid a potential low-blood glucose problem. The user interface shows a second glucose event indicator 1214 around 1:30 PM, at which time the glucose concentration level was moderate (129 mg/dL) and the trend was steady (indicated by a sideways arrow). The glucose event 1214 may, for example, correspond with a user-specified after-lunch report, or may occur at a time calculated by a system (e.g., mid-day or post-lunch report). The example user interface 1202 shows a third glucose indicator 1222 around 7:30 PM, at which point the glucose concentration level was high (203 mg/dL) and trending upward quickly, as shown in this example by two upward arrows. In some examples the glucose indicators may be shaded, colored, or otherwise visibly identified to indicate whether the glucose concentration level satisfies a glucose management condition, e.g., whether the glucose concentration levels are within a specified range.

The user interface 1202 may include a plurality of meal indicators, e.g., a breakfast indicator 1208, a lunch indicator 1212, and a dinner indicator 1220. The meal indicators 1208, 1212, 1220 may correspond to the user's meals. User meals can be identified from user input, such as a smartphone input that indicates a meal was consumed and may optionally include information about the meal such as meal content (e.g., carbohydrates, protein and fat, or food type such as "one slice of pizza and a glass of milk"). User meals, in some examples, are also identified from other types of input including, for example, geolocation data, motion data, etc. For example, geolocation data may indicate that the user is present in the user's kitchen, at a restaurant, or at another location where food is prepared and/or served. Also, for example, motion data can indicate user motion consistent with eating. Such motion can include, for example, the user repeatedly moving the user's hand to the user's mouth.

The user interface 1202 may also include an activity event, such as walk event 1216. In some examples, the walk event 1216 may be determined by a system based at least in part on activity data from an activity sensor (e.g., from a wearable device 120) or based on a physiologic sensor (e.g., heart rate sensor), or a combination thereof. In some examples, the walk event 1216 may be based at least in part on user input (e.g., input via a user device 132 indicating that a walk occurred.)

The user interface may include a medication event 1224, which may be based on user input (e.g., input received via a user device 132) or may be based on sensed or controlled event from a device (e.g., from an event sensor on an insulin injection device or medication information received from a pump.)

The user interface may also include guidance comments. For example, the user interface may include a guidance bubble 1210 that states that "You had a spike the last three days at 1 pm" and a second guidance bubble 1226 that states that "Medication is best taken before bedtime." In some examples, the guidance bubbles are provided in the morning, and the data event indicators appear as time passes through the day. When the guidance bubbles 1210, 1226 are provided prospectively, the guidance may prompt the use to act, e.g., to modify a breakfast meal content or to take a mid-day walk to address the recurrent glucose spike at 1 PM. In some examples, a guidance bubble 1210, 1226, etc., can be selected to launch chatbot functionality for providing guidance to the user.

In some examples, the user interface may include game features (e.g., awards or badges) to promote user engagement. For example, the user interface 1202 may present a badge 1218, which may show a still or animated walking person, and may also present a comment that "Post-meal walking skill unlocked!" to acknowledge an activity behavior by the patient. In some examples, a determination to award the post-meal walking skill may be made by a system (e.g., remote system connected via a network 124 or a processor in user device 132.) The user interface may also include a medication badge (Rx) 1228 that may be presented with a message "Medication optimization skill unlocked." In some examples, a system may determine to award the medication badge 1228 based upon satisfaction of a delivery condition, such as delivery of medication within a specified period of time before sleep (which may be detected by an activity sensor, posture sensor, physiological sensor(s), or any combination thereof.) In some examples, a machine learning technique can be used to relate game features to patient outcomes, such as desired levels of glycemic control. In this way, the system can arrange game features to improve patient results, thereby increasing the effectiveness of the system.

Figure 12C:
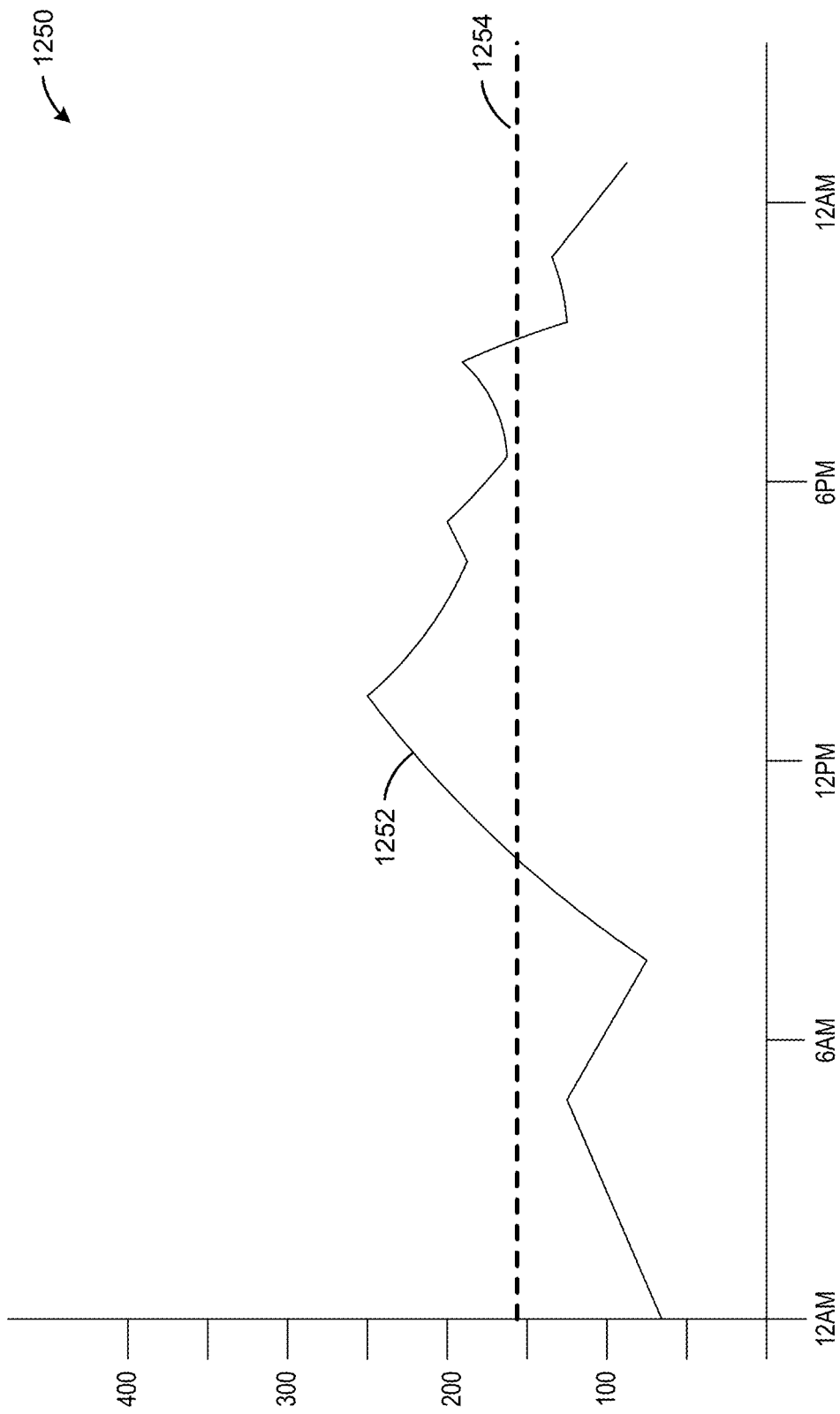
FIG. 12C is an illustration of an example user interface including a target A1C indicator.

In some examples, a user interface can provide a plot of glucose levels along with an indication of an average glucose level for achieving a particular A1C value. FIG. 12C is an illustration of an example user interface 1250 including a target A1C indicator 1254. The user interface 1250 includes a plot 1252 of blood glucose over time. The target A1C indicator 1254 indicates an average blood glucose corresponding to a desired A1C for the user. In the example of FIG. 12C, the A1C indicator 1254 is situated at a blood glucose level of 154 mg/dl, which corresponds to an A1C of 7.0. In some examples, a target A1C indicator, such as the example 1254, can be used in other user interfaces, such as the user interface 1202 d3escribed herein. Also, like the user interface 1202, the user interface 1202 may be presented on a user device, such as user device 132, or additionally or alternatively may be presented on hand-held smart device (e.g., smartphone) 112, tablet 114, computer 118, a wearable device 120, a peripheral medical device 122, or remote terminal 128.

Figure 13:
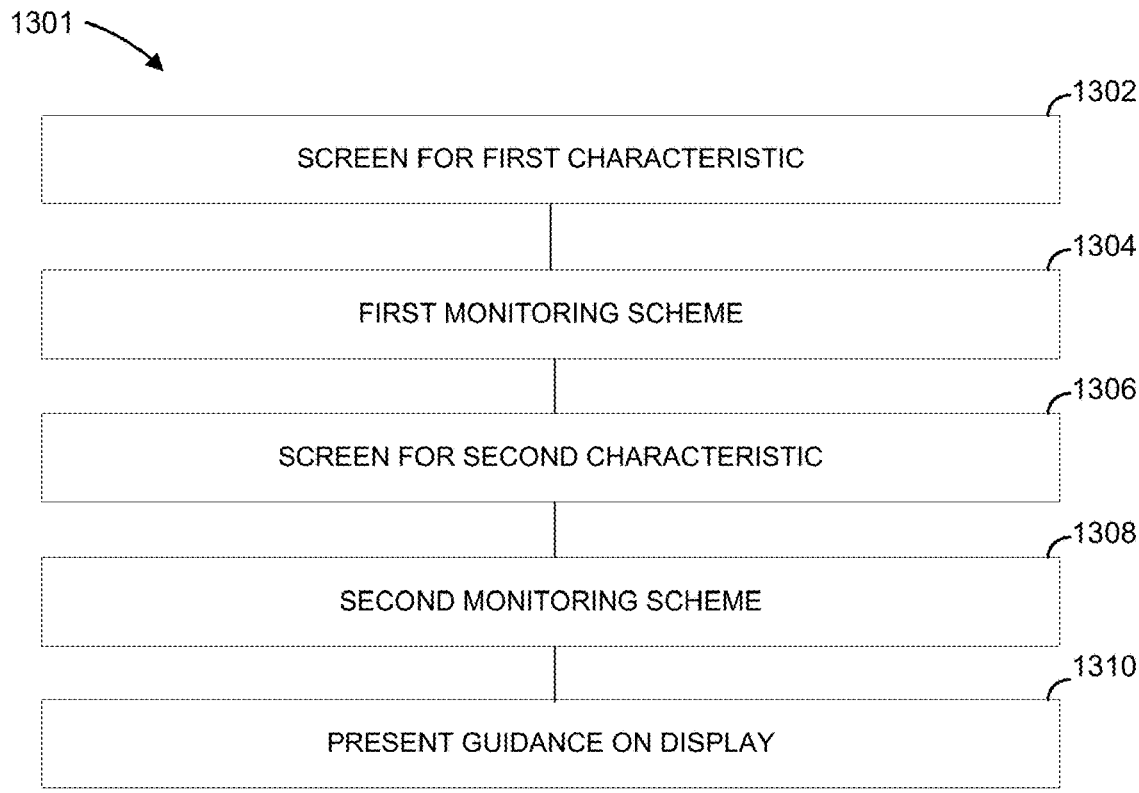
FIG. 13 is a flowchart illustration of a method of identifying or selecting a patient who may benefit from an enhanced disease management program.

FIG. 13 is a flowchart illustration of a method of identifying or selecting a patient who may benefit from an enhanced disease management program, such as intermittent CGM for management of type 2 diabetes or other high-fidelity monitoring, or low-fidelity monitoring (e.g., activity monitoring) with optional correlation to high-fidelity (e.g., CGM) information. In some examples, the method may include determining whether a patient improvement condition is likely to be satisfied by enhanced monitoring. For example, the method may include determining an estimated likelihood that the patient will benefit from enhanced monitoring scheme. The estimated likelihood may be a calculated value or percentage, such as 75%, 90%, or 95%, which may optionally be configurable by a user (e.g., patient or health system administrator.) The method may include a measurable improvement as an indicator that the patient will benefit (or has benefitted) from enhanced monitoring, such as a reduction in A1c, an achievement of an A1c goal (e.g., A1c under 7.0), or a reduction in glucose variability, or any combination thereof.

At 1302, a system, such as system 125, 126, or 127, may screen for a first characteristic. For example, the system may perform a first screening algorithm (e.g., on a processor) on stored data for a pool of participants (e.g., patients) to determine a group of individuals with diabetes or with the diabetic risk factors. The method may employ factors such as electronic health records, type II diabetes diagnosis codes, family history, weight, BMI, history of metabolic diseases, blood test results, A1c, fasting glucose levels, oral glucose tolerance, prescribed diabetes medications, or any combination thereof.

At 1304, a first monitoring scheme may be applied to obtain additional data for the determined group of individuals. For example, the method 1301 may include providing a first kit to participants in the determined group. The kit may be structured and configured to enable a participant of the determined group to perform low-fidelity monitoring of their health for a first duration with a first monitoring technique and obtaining first results. Information may be received from a device in the kit by system 127, or by another system or device.

In various examples, the low-fidelity monitoring may include single-point glucose monitoring, heart rate monitoring, activity monitoring, blinded continuous glucose monitoring, or any combination thereof.

At 1306, a system (e.g., system 127, or user device 132) may screen for a second characteristic. For example, the system may perform a second screening algorithm on the determined group to determine a cohort for participation in intermittent high-fidelity monitoring. The second screening algorithm may be based at least in part on the results obtained using the first monitoring scheme. In some examples, the intermittent high-fidelity monitoring may include continuous glucose monitoring. In some examples, the screening may be based at least in part on a factor of adherence (e.g., whether a user adhered to a monitoring plan) to use of the first scheme (e.g., low-fidelity monitoring technique). For example, a factor in determining to utilize high-fidelity monitoring may be the degree to which the patient complied with instructions or procedures for low-fidelity monitoring, such as wearing an activity monitor or taking blood glucose meter measurements according to a specified schedule.

At 1308, a second monitoring scheme may be applied. For example, the method 1301 may include providing a second kit to participants in the determined cohort. The second kit may be structured and configured to enable a participant of the determined cohort to perform high-fidelity monitoring of their health, for a second duration with a second monitoring technique, and obtaining second results. In some examples, the second kit may include a continuous glucose monitor. The second kit may be structured and configured based on the obtained first results. For example, in an example where the second monitoring scheme is continuous glucose monitoring, a quantity or type (or both) of glucose sensors that are provided in the second kit may be determined based on the obtained first results. In some examples, a determination may be made to include a number of a first type of sensors that use a first communication technology (e.g., NFC, which must be swiped by a smart device to pull glucose data), or a number of sensors of a second type that are designed for use with a longer-range transmitter (e.g., Bluetooth) that may provide glucose information to a wireless device (e.g., smart phone) without human interaction, or a blend of the first type of sensors and second type of sensors.

At 1310, the method may include providing guidance. For example, the method may include presenting guidance on a display of a user device, such as a handheld device (e.g., smartphone.) In some example, the guidance may be provided using chatbot functionality, as described herein. In some examples, the method may include performing communications between a server and a device in the first kit. The communications may, for example, be provided during the first monitoring. The communications may provide the guidance to the patient or caregiver (e.g., coaching information about steps to take to lower glucose level, such as exercise, or feedback on glucose control, such as an estimated average glucose concentration or variability or both for a specified time period.) The guidance may, for example, include diabetes management guidance that involves a lifestyle modification relating to diet or exercise, glucose level monitoring, or medication, or any combination thereof. In some examples, the guidance may include an indication of a duration or schedule of time for to employ high-fidelity monitoring, such as one week, or ten days, or one week per month.

The method may optionally further include providing a third kit to one or more participants in the determined cohort, the one or more participants determined according to, at least in part, the obtained second results. The third kit may be structured and configured based on the obtained second results. For example, the third kit may include a quantity of continuous glucose monitoring sensors, where the quantity or type (or both) of sensors is determined based at least in part on the obtained second results.

While a low-fidelity to high-fidelity progression is described above, the method may alternatively include a high-fidelity to low-fidelity progression. For example, the first monitoring scheme may include high-fidelity monitoring (e.g., using a CGM), the screening for a second characteristic at 1306 may be based at least in part on information from the high-fidelity monitoring, and the second monitoring may include low-fidelity monitoring, such as activity monitoring.

The method 1300 may be implemented in a specialized system, which may include hardware components, software components, or both, such as the system 2200 shown in FIGS. 22A, 22B, 22C, and 23. For example, patient data may be retrieved from electronic storage, analyzed using a process, e.g., to determine patients who may benefit from high-fidelity monitoring, and electronic instructions may be sent to a provisioning system to initiate delivery of one or more sensing kits to a specified patient or cohort of patients.

Figure 14:
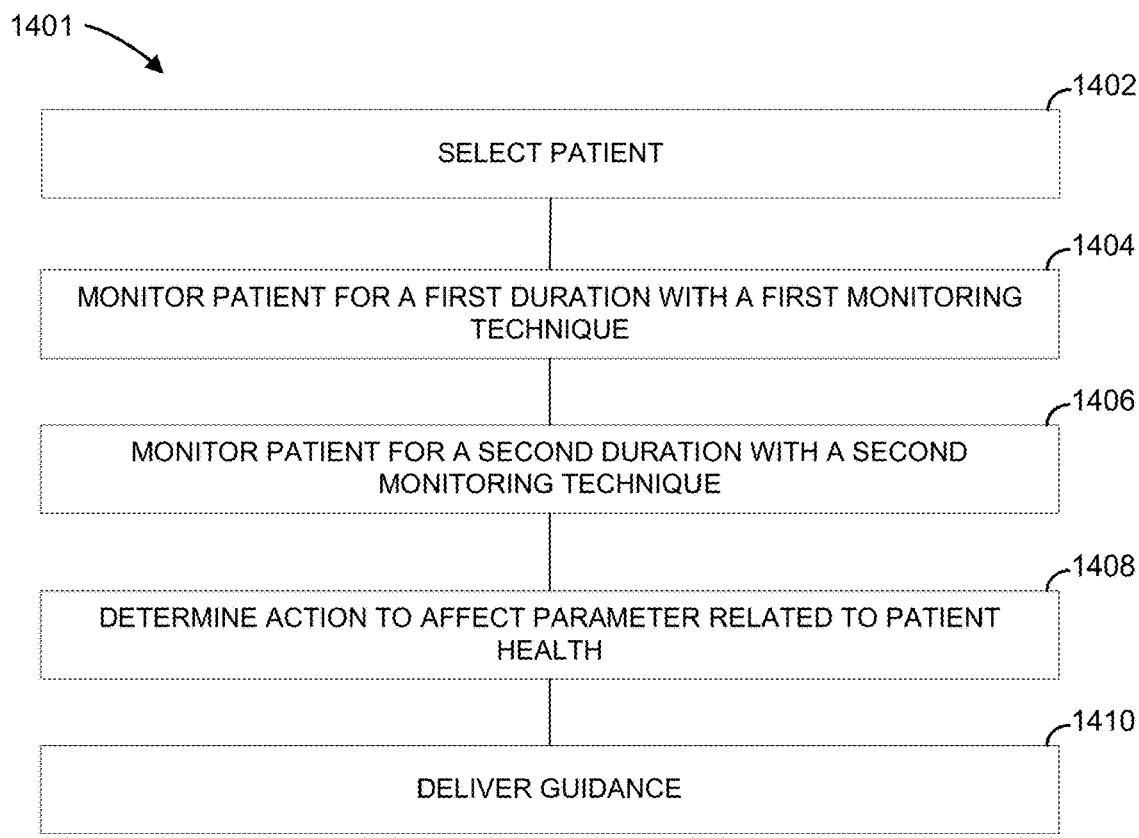
FIG. 14 is a flowchart illustration of an example method of managing a parameter related to patient health.

FIG. 14 is a flowchart illustration of an example method of managing a parameter related to patient health using intermittent high-fidelity monitoring. At 1402, a patient is selected. The selecting a patient may, for example, include determining a patient from a pool of patients likely to benefit from intermittent high-fidelity monitoring, the likelihood greater than a calculated value. The patient pool may, for example, represent a group of patients at a clinical practice, or in a specified insurance pool or program, or in a geographic location, or at a workplace, or any combination thereof.

At 1404, a patient may be monitored for a first duration (e.g. period of time) using a first monitoring technique, which may produce a first result (or set of results.) The first technique may, for example, include high-fidelity monitoring (e.g., using CGM) or low-fidelity monitoring (e.g., using a blood glucose meter.)

At 1406, the patient may be monitored for a second duration using a second monitoring technique, which may produce a second result (or set of results.) In various examples, the first duration may be a subset of the second duration or may overlap the second duration.

In some examples, the first technique may include high-fidelity monitoring, and the second technique may include low-fidelity monitoring, which may be determined at least in part by the results of the high-fidelity monitoring. In some examples, the first technique may be single-point glucose monitoring, or blinded continuous glucose monitoring (e.g., continuous glucose monitoring where the patient does not receive some or all of the estimated glucose concentration levels.) In some examples, the first technique may include activity monitoring using a wearable fitness tracker, such as a heart rate monitor, activity monitor, smart phone, smart glasses, or smart watch, or any combination thereof. In some examples, the second monitoring, the low-fidelity technique may include receiving user input data, such as medicament data meal data, exercise data, sleep data, or any combination thereof.

In other examples, the second technique may include low-fidelity monitoring, and the first technique may include high-fidelity monitoring, which may be determined at least in part by the results of the high-fidelity monitoring.

At 1408, an action the patient may perform may be determined based on the first result and second result. The action may be calculated to increase a likelihood of satisfaction of a management condition. For example, the action may be calculated to increase a parameter related to patient health by greater than a predetermined amount with a confidence greater than a predetermined confidence level. For example, the action may be calculated to increase a time-in-range, such as an amount (e.g., percentage or number of minutes or hours) that an estimated glucose concentration level is in a specified range. In another example, the action may be calculated to change (e.g., increase, or decrease) a glycemic variability by a specified amount.

At 1410, guidance may be delivered. For example, the guidance may be presented on a display. In various examples, the guidance may relate to a diet, exercise, glucose level monitoring, or medication. In some examples, the guidance may indicate the performance of a patient in satisfaction of a condition (e.g., goal) relating to diet, exercise, glucose level monitoring, or medication, or another health-related matter. Delivering the guidance may include performing communications between a server and a device associated with the patient. In some examples, delivering the guidance can include delivering a chat bot functionality to the device associated with the patient. The communications may occur during the first time period or during the second time period, or both, or after the second time period. In some examples, the communications may provide a coaching functionality to the patient.

In some examples, delivering the guidance may include displaying (or otherwise communicating via a device or system) an optimized duration of time for which the patient should employ high-fidelity monitoring.

In some examples, the method may include correlating the obtained first and second results, for example by determining a relation between the obtained first and second results at corresponding times of day, days of the week, locations, or other correlating factors. The method may further include calculating an estimated value for a high-fidelity monitoring technique at a given time based on the correlated value for the given time obtained by the low-fidelity monitoring technique. In some examples, the guidance delivered at 1410 may be based on the estimated value for the high-fidelity monitoring technique. In various examples, calculating an estimated value for a high-fidelity monitoring technique, or determining a correlation, may be based at least in part on population data corresponding to the patient, or physiologic or other data about the patient collected using a sensor, or user input regarding the patient, or any combination thereof.

Figure 15:
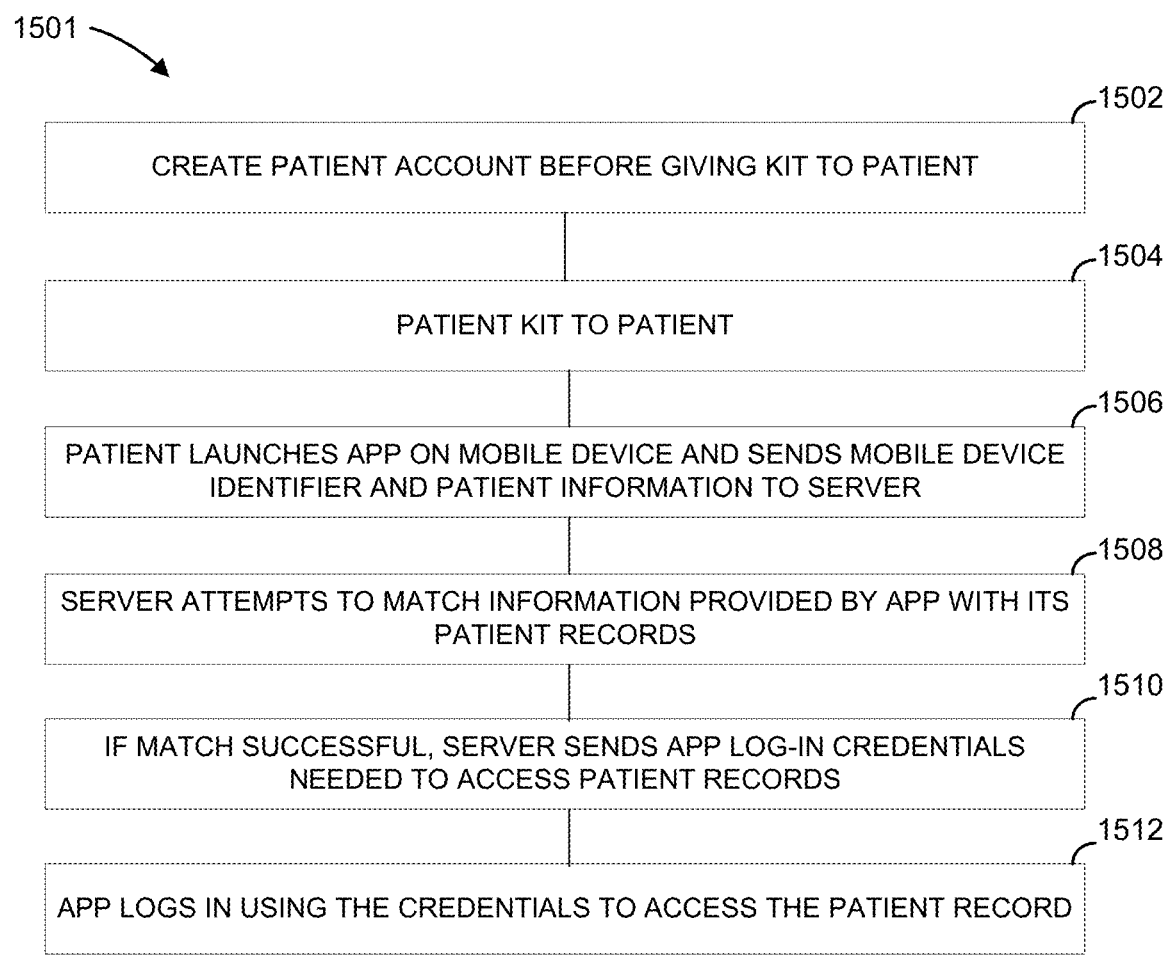
FIG. 15 is a flow chart illustration of an example login process.

FIG. 15 shows one example of a method 1501 in which a patient's user account may be set up on a server so that the patient is able to automatically log-in using the app on their mobile device while only entering a minimal amount of information.

In step 1502, prior to providing the kit to the patient, the patient account is set up on the patient's behalf in a database that is maintained on a server. Among other things that are provisioned in the patient account such as the patient name, data of birth (DOB), and so on, the patient account is provisioned with a unique identifier of the mobile device that is included with the kit that is to be provided to the patient. For example, the identifier may be the international Mobile Equipment Identity (IMEI) of the mobile device. If the mobile device that is used is provided by the user and is not part of the kit, a different mobile device identifier may be assigned and used as the unique identifier.

In step 1504, the patient is provided with the kit, including the mobile device. In step 1506, the user launches the app, which establishes communication with the server and automatically sends the unique identifier of the mobile device. The app will also send patient information that has also been pre-provisioned in the patient record, which is used to associate the patient with the mobile device. This information may include, for example, one or more of the following: the patient's email address, DOB, phone number, and so on.

In step 1508 the server attempts to match the unique identifier of the mobile device and the patient information to a patient record that is stored in its database. If the match is successful, then in step 1510 the server sends the app the credentials needed to log in or otherwise access the matching patient record in the database. The app then logs in using the credentials to access the patient record in step 1512.

The automatic log-in procedure described above has been illustrated for a new patient for which a user record needs to be created. The procedure may also be used for existing patients. For instance, if in step 1504 instead of providing a kit to a new patient, an existing patient is provided with a new transmitter, then in step 1502 instead of creating a new patient account, the identifier of the new transmitter will be entered into the patient's existing record. Thus, in this way the process shown in FIG. 15 allows both new and existing patients to automatically log-in and access their patient account record with minimal effort.

It should be noted that the functionality of the server employed in the automatic log-in procedure discussed above in some cases may be distributed among multiple servers which may or may not be controlled by the same entity. For instance, in one particular example one or more of the servers may be controlled and operated by a device manufacturer and one or more additional servers may be controlled and operated by a database provider.

Figure 16:
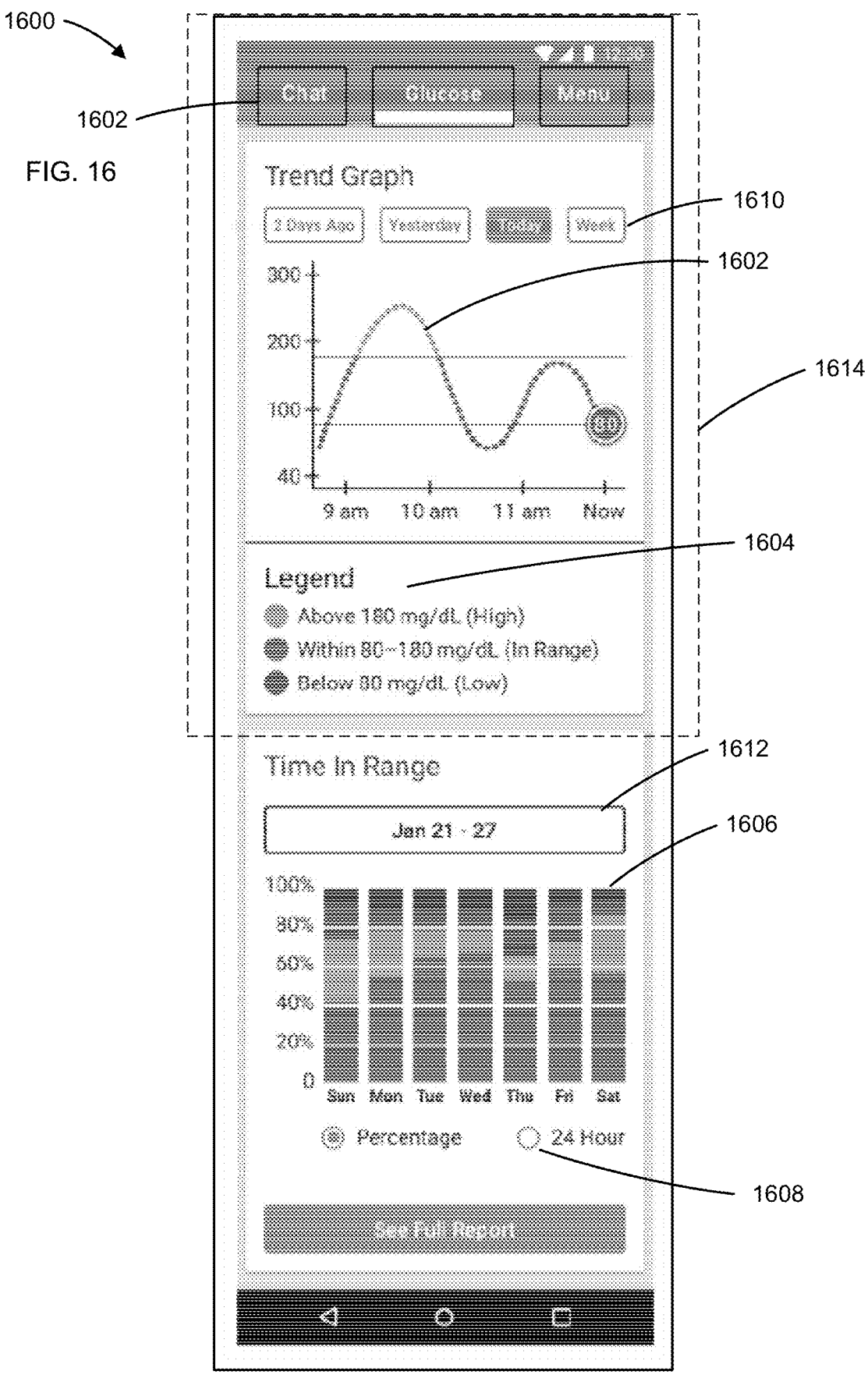
FIG. 16 is an illustration of an example user interface.
Figures 19, 20:
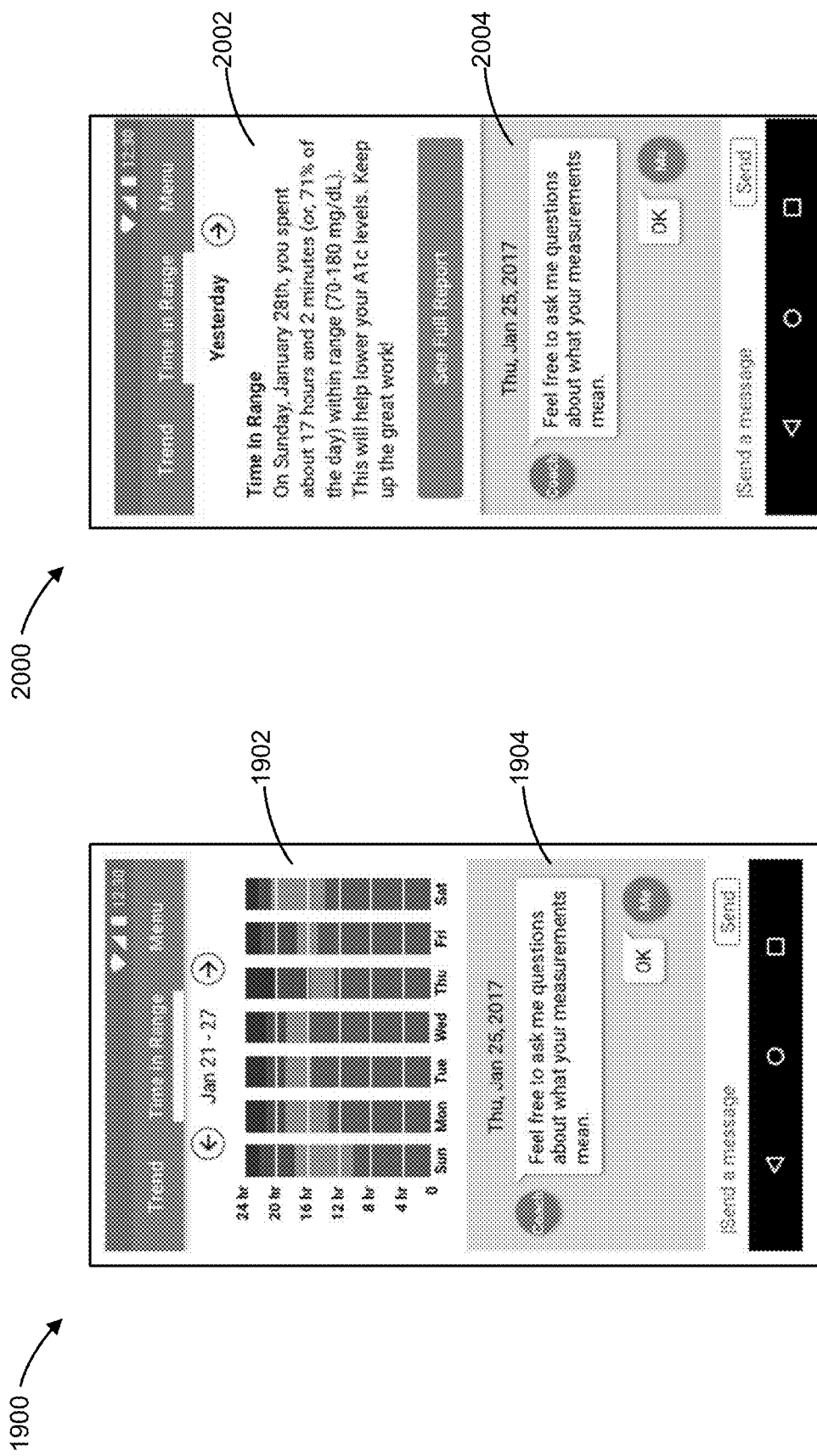

FIG. 16 is an illustration of an example user interface 1600, which may for example be presented on a display of a smart device such as hand-held device 112 or on a display of a wearable device 120. The user interface 1600 may include a trend graph 1602 that may show high-fidelity data (e.g., CGM data) plotted against time for a portion of a present day. The user interface screen shown in FIG. 16 may be accessed by selecting a button (labeled "Glucose") on the user interface. The user interface 1600 may include a legend 1604 that provides explanatory information about the plot. A time selector user interface element 1610 may allow a user to control the time period for which data is displayed (e.g., today, yesterday, two days ago, or an entire week.) The user interface 1600 may also provide a time-in-range chart 1606, which may for example show a percentage (as shown) or amount of time (e.g., minutes or hours) in range for a number of time periods (e.g., days in a week, as shown, or portions of a day, such as morning, afternoon, evening, night). The interface 1600 may include an input element 1608 that allows a user to choose a percentage-based display as shown in FIG. 16, or a time-based display 1902 as shown FIG. 19. A time selector user interface element 1612 may receive user input for the time-in-range chart, and may allow a user to select, for example, a specific week for which to show data, or a different size time periods (e.g., time-in-range for portions of a day, or for weeks, or for months.) In some examples, both the trend graph may be shown at the same time, or a scrollable portion 1614 (indicated by dashed lines) may be visible on a display screen, and the user interface may receive a user input (e.g., via a touch screen) to scroll or zoom to show the time-in-range graph in addition to or as an alternative to the trend graph.

In an intermittent monitoring example, the trend graph may be presented for time periods (e.g., days) when high-fidelity collected data (e.g., CGM data) is available, and the time-in-range chart may be provided for time periods (e.g., weeks) when low-fidelity collected data is available (with or without high-fidelity data).

Figure 17:
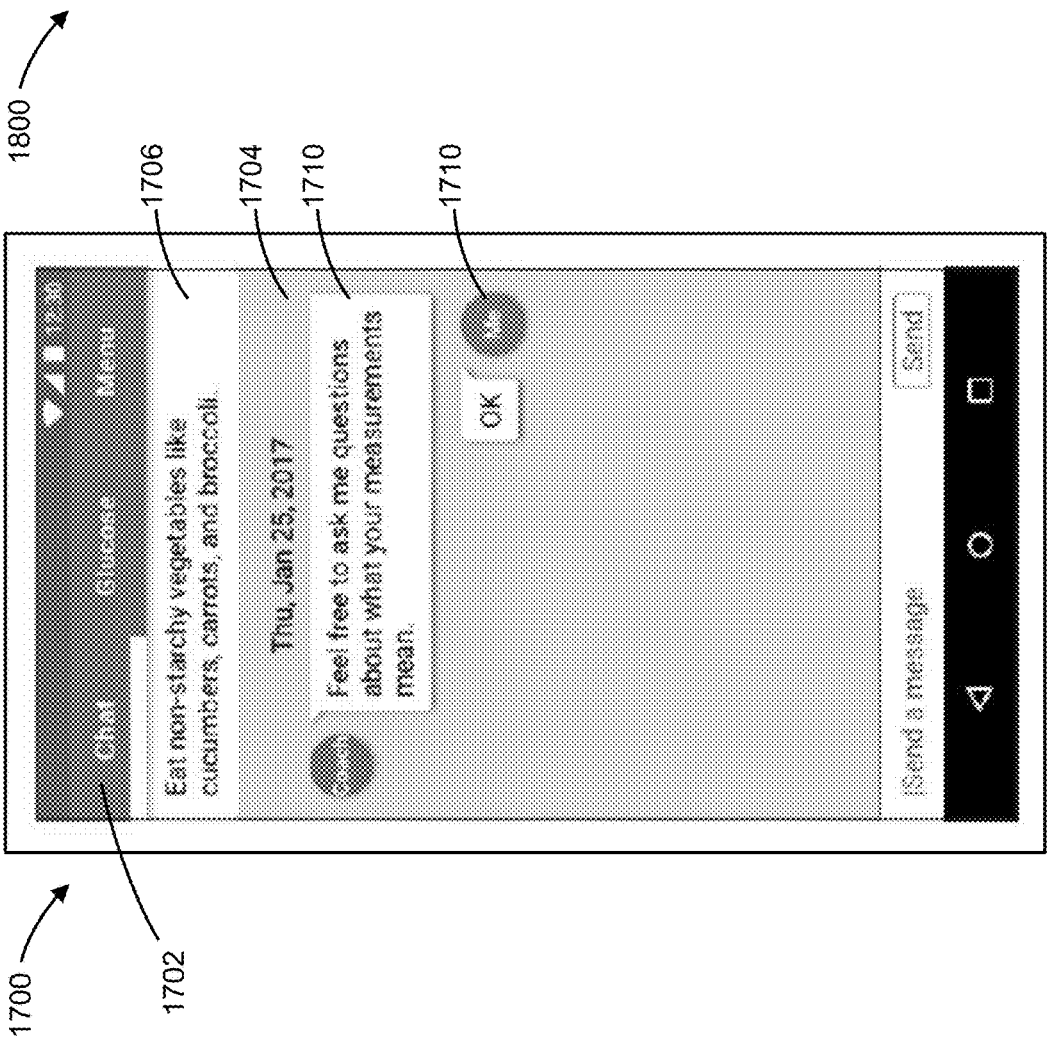

FIG. 17 is an illustration of an example chat user interface 1700, which may for example be presented on a display of a hand held device 112 or on a display of a wearable device 120. The chat user interface 1700 may be accessed by selecting a chat user interface element 1702, which may initiate a chat session in a chat window 1704 with a human coach or a chat bot coach. The chat user interface 1700 may also include a context field 1706. The context field 1706 may for include a guidance message, which may for example be provided in response to high-fidelity or low-fidelity collected data. The chat interface may present information 1708 from the coach and comments or questions 1710 from the user. Input from a user may be received via a virtual keyboard (not shown) or using a microphone and voice recognition software. For example, a user may ask "Why should I eat vegetables" and a coach (e.g., chat bot) may respond "Vegetables tend to help you keep your glucose in range because they have fewer simple carbohydrates that foods like bread or sweets." In some examples, the chat session may be conducted using a microphone and speaker in addition to or as an alternative to the on-screen chat shown in FIG. 17.

Figure 18:
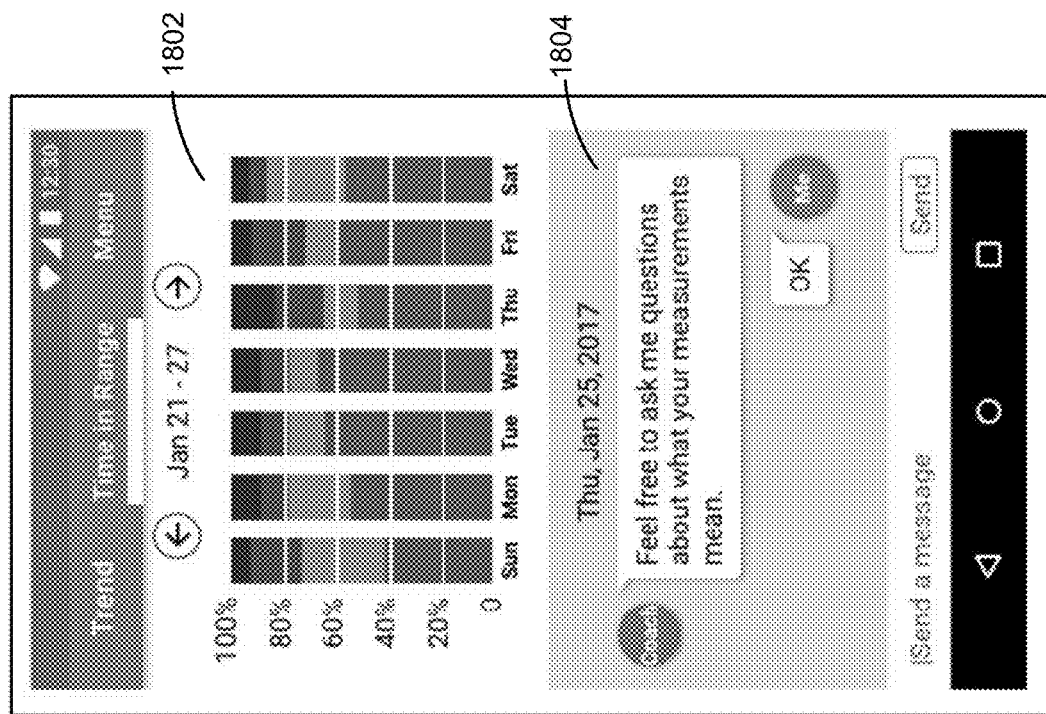
FIGS. 17-20 are illustrations of example chat interfaces.
Figure 21:
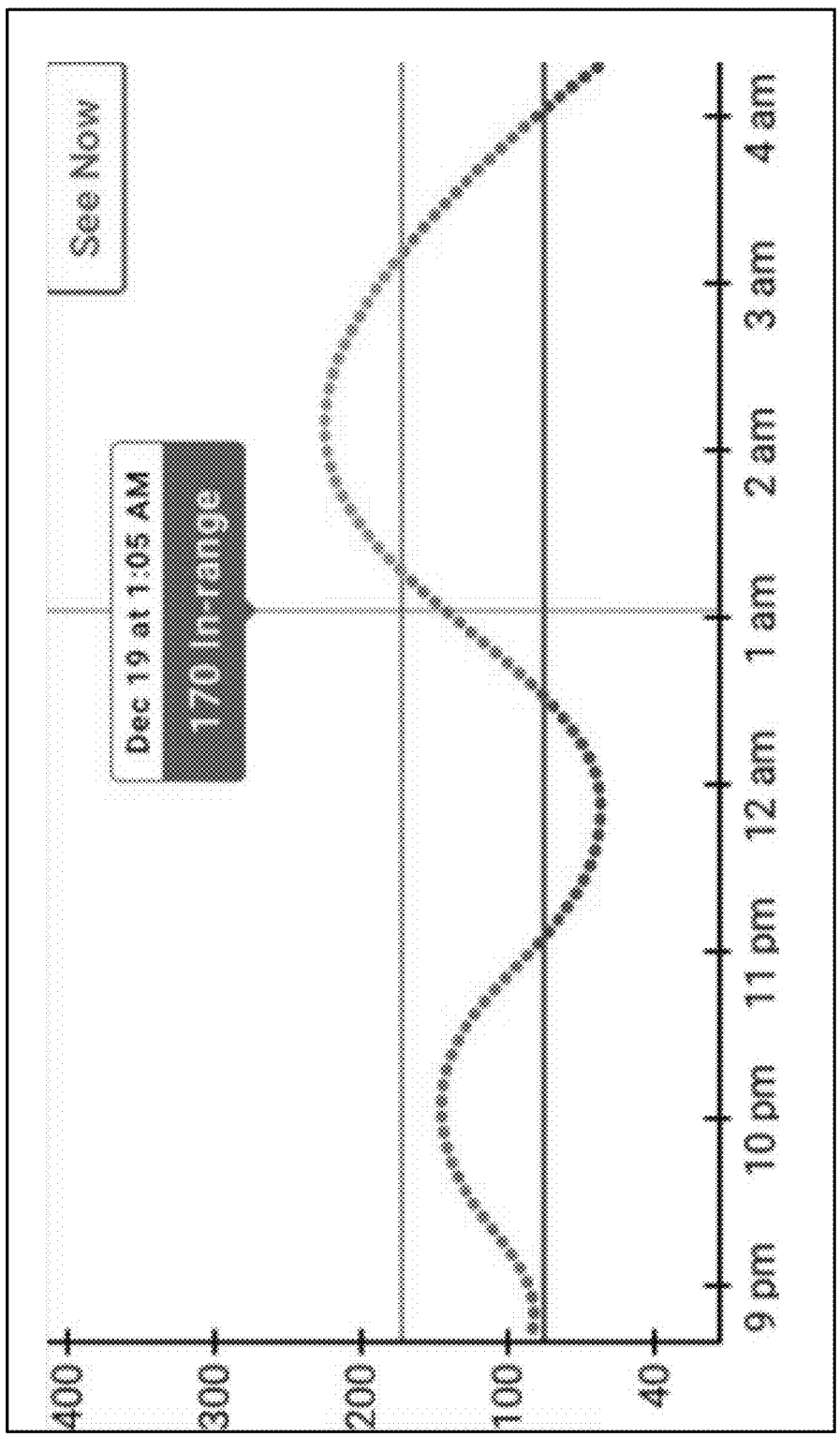
FIG. 21 is an illustration of an example trend graph.

FIG. 18 shows a chat interface 1800 with a chart in a context field 1802. The chart may, for example, be a time-in-range chart (as shown), such as a percentage-based chart shown in the context field in FIG. 18, or a time-based chart in the context field as shown in the user interface 1900 shown in FIG. 19, or the chart may be or a trend, as shown in FIGS. 16 and 21. In another example, a user interface 2000 may include a text message in the context field 2002. A user and coach may interact in the chat field 1804, 1904, 2004, for example to ask or answer questions with respect to the chart. In a device with space constraints, input from a user may advantageously be received via a microphone and voice recognition software to avoid conflicts in demands for screen space with the chat field 1804, keyboard (not shown) and context field 1802. For example, an auditor chat functionality (e.g., using microphone and speaker) may be initiated by selecting a chat button 1620 in the interface shown in FIG. 16. In some examples, a chat session may be triggered by sensed data, information about a patient, or other chat trigger condition. For example, a chat session may be triggered responsive to a trend that satisfies a trend condition or range condition, which may for example enable a patient or user to take corrective action (e.g., participate in an activity such as exercise or change a dietary choice or administer a medication). For example, a chat session may be triggered by an estimated glucose concentration level that is rising or falling quickly, or likely to trend far out of range, or out of range at a time or under circumstances where glucose would normally be in range, or out of range for more than a specified period of time (e.g., out of range for 12 hours), or out of range for more than a specified percentage of time over a specified period (e.g., more than 60% for a specified day or week.)

In some examples, the user interface 1600, 1700, 1800, 1900, 2000 shown in FIGS. 16-20 may adapt based on information about a user. For example, the user interface may adapt based upon preferences or characteristics about the sophistication or use of the interface by a user. In some examples, the user interface may provide fewer options, a larger display, or simpler information to accommodate a user who exhibits a tendency or preference toward less sophisticated interactions. In some examples, the user interface may adapt based upon an age or time (e.g., year) of birth of a user. For example, a user who satisfies a particular age condition (e.g., over 60, 65, or 70 years) may be presented with a user interface that has a specified appearance scheme (e.g., color scheme or high-contrast) or larger buttons or larger fonts.

FIG. 21 is an illustration of an example user interface 2000. The user interface 2000 may be a landscape mode view (e.g., width larger than length, which may be useful when a handheld smart device is turned on its side.) The user interface 2000 may be laterally scrollable to show data for time periods to the left (i.e. earlier) or to the right (i.e., later) of the data presently shown. For example, the data may "slide" to the right when a user touches the screen and swipes to the right, to show data for time before 9 PM, and the data may slide to the left responsive to a user swipe to the left, e.g., to show data for a time after 4 PM. The user interface 2100 may also include a user interface element 2102 (e.g., "See Now" button), and, responsive to a user selection of the user interface element 2102, that user interface may refresh, or slide left or right as appropriate, to show data for the current time. The slideable user interface may be useful in coaching, e.g., a user may receive an instruction from a coach to view data for a specific time or event (e.g. dinner), and subsequently receive an instruction to select the user interface element 2102 to return to current data.

Figure 22A:
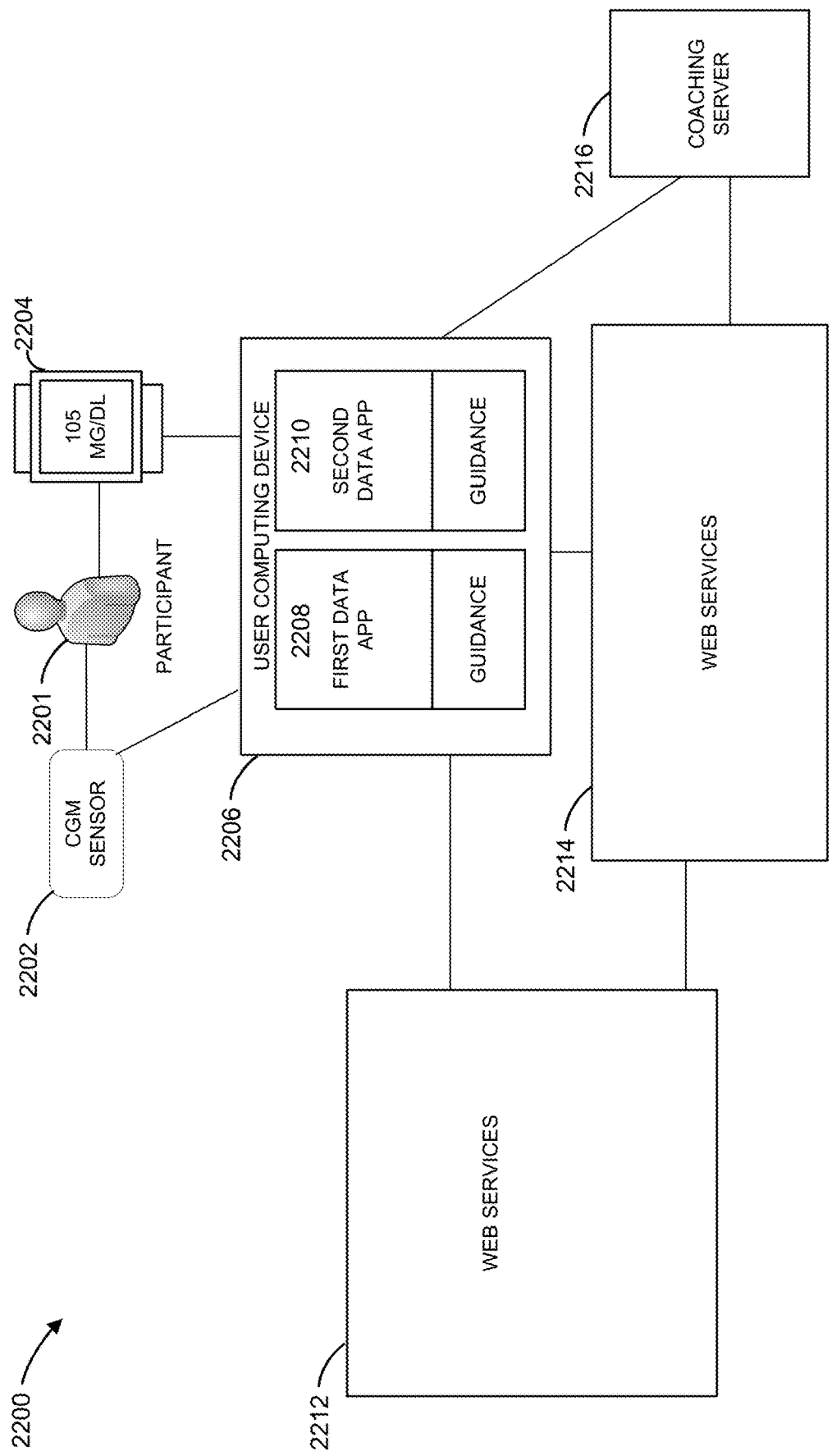
FIG. 22A is an illustration of an example system in which the methods, devices, and subsystems may be implemented.

FIG. 22A is an illustration of an example system in which various examples described herein may be used or applied. The system 2200 may include a continuous glucose monitoring sensor 2202 and activity sensor 2204 (e.g., a watch), which may be worn by a participant (e.g., patient) 2201 to generate glucose concentration information and activity information regarding the patient. The CGM sensor 2202 may provide activity information to a user computing device 2206 (e.g., smart phone or watch) and the activity sensor 2204 may provide activity information to the user computing device 2206, which may for example be a hand-held device (as shown) or a wearable device, such as a watch. While the user computing device 2206 and activity sensor 2204 are illustrated as separate devices, in some examples, the activity sensor 2204 may be part of the user computing device 2206 (e.g., the smart device may be a wearable device such as a watch that includes the activity sensor.)

One or more applications may run on the user computing device 2206 to provide glucose concentration information, activity information, or guidance to a patient. For example, a first application 2208 running on a smart device may provide information about glucose concentration levels, and optionally also provide guidance relating to managing the glucose concentration levels, and a second application 2210 running on the smart device may provide information about activity, and optionally also provide guidance relating to activity (e.g., "Consider a vigorous walk this afternoon" or to glucose concentration level management (e.g., "You may need to take steps to lower your glucose level today"), or to both (e.g., "Consider a vigorous walk this afternoon to help lower your glucose level today.") While two discrete applications are illustrated, in some examples the smart device may run a single application that combines the features described above (i.e., a single application may provide information on both glucose concentrations and activity and guidance relating thereto.)

The system may include one or more web services systems, which may for example include one or more servers configured to communicate over a network with or regarding the user computing device 2206, CGM sensor 2202, activity sensor 2204, or other devices. For example, a first web services system 2212 may collect information relating to continuous glucose management, and a second web services system 2214 may collect activity information and may optionally collect CGM information from the first web services system 2212. A third web services system 2216 may operate as a coaching server to facilitate interaction with a human or computerized coach via coaching guidance through the user computing device 2206 or phone call follow-up communications. In some examples, the coaching server 2216 may be or include the coaching server 2412 or coaching server 2512 shown in FIGS. 24 and 25 and described below. While the web services systems 2212, 2214 and coaching server 2216 are shown as three separate systems, they may alternatively be portions of a single system (e.g., subsystems), or a single system may perform tasks of two or more systems.

Figure 22B:
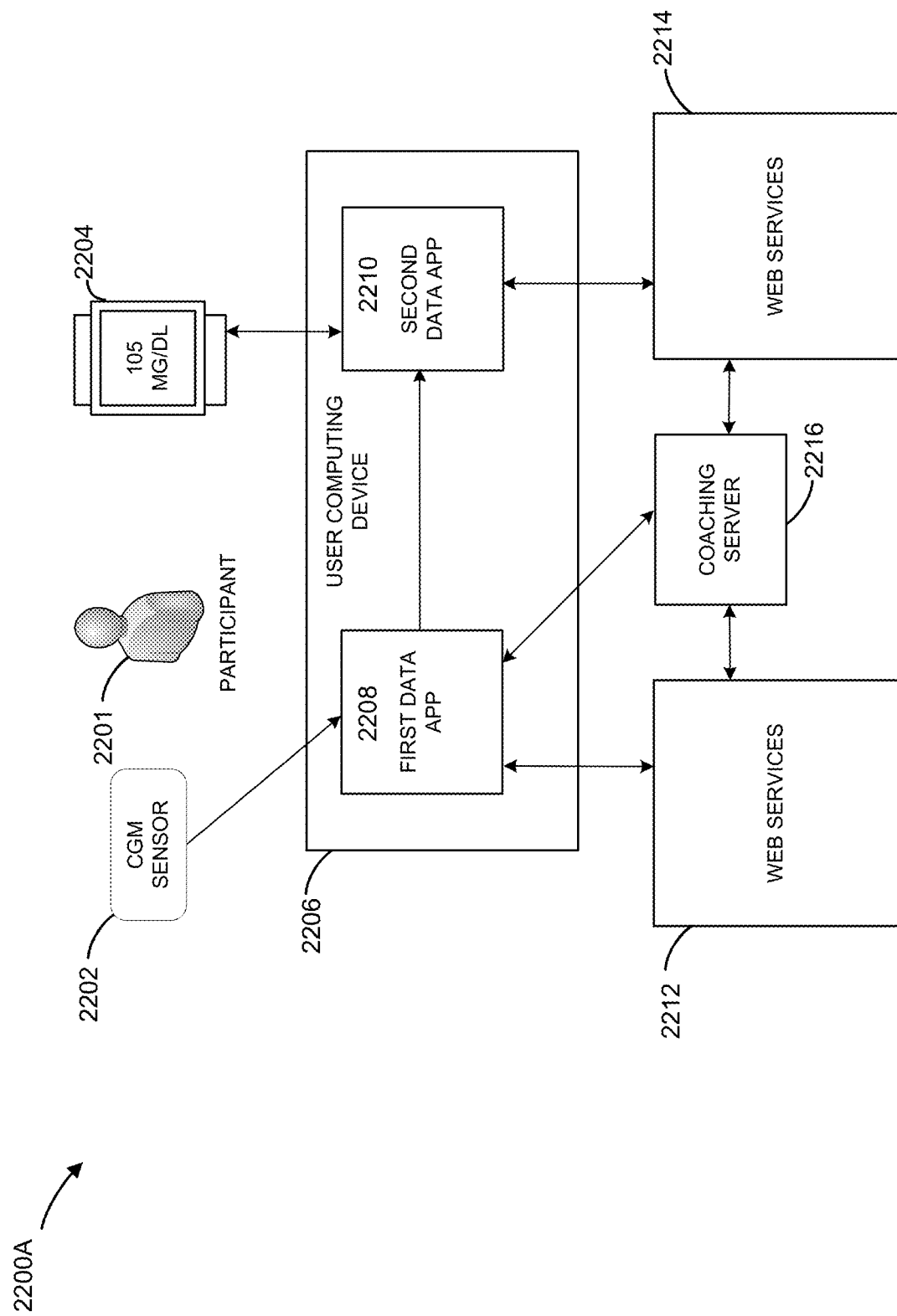
FIG. 22B is an illustration of an example system that is an arrangement of the system of FIG. 22A.

FIG. 22B is an illustration of an example system 2200A that is an arrangement of the system 2200 of FIG. 22A. In this example, the first data application 2208 is configured to establish a first communication link with the continuous glucose monitoring sensor 2202. The first communication link, in some examples, administered by the user computing device 2206, for example, by an operating system of the user computing device 2206. The first communication link can be a wireless communication link such as, for example, a Bluetooth, Bluetooth LE, or other suitable wireless communication link. The continuous glucose monitor sensor 2202 can transmit CGM data to the first data application via the first communication link including, for example, glucose data describing an estimated glucose value for the participant 2201. In some examples, the CGM data provided by the continuous glucose monitor sensor 2202 also includes metadata describing the participant 2201 and/or diagnostic data describing the performance of the continuous glucose monitor sensor 2202.

The second data application 2210 can be configured to establish a second communication link with the activity sensor 2204. The second communication link can be a wireless communication link, for example, similar to the first communications link. The activity sensor 2204 can provide the second data application with activity data describing activities of the participant 2201 via the second communication link. For example, an accelerometer or other suitable sensor of the activity sensor 2204 can capture data indicating motion or other activities of the participant 2201 and provide corresponding data to the second data application 2210 via the second communications link. The second data application 2210, in some examples, provides UI data to the activity sensor 2204 via the second communication link. For example, the activity sensor 2204 can include an output device such as, for example, a lamp, a display screen, a speaker, etc., to convey the UI data to the participant 2201. The UI data, for example, can describe the activities of the participant 2201, for example, as captured by the activity sensor 2204.

In some examples, the first data application 2208 is configured to communicate CGM data to the second data application 2210. The second data application 2210 can then provide the CGM data to the activity sensor 2204 as UI data to be provided to the participant via the output device of the activity sensor 2204. In this way, the activity sensor 2204 can provide the participant with an indication of glucose data such as the participant's current estimated glucose value and/or of metadata such as a direction in which the participant's glucose value is trending, past glucose values for the participant 2201, etc.

Communicating CGM data between the first data application 2208 and the second data application 2210, however, can raise data security issues. For example, CGM data may be at risk of being nefariously intercepted by another application (not shown) executing at the user computing device 2206.

To prevent CGM data from being intercepted, the first data application 2208 and second data application 2210 can be configured to communicate via a secure communication protocol. Examples of the secure communication protocol are described herein with respect to FIG. 22C.

The example system 2200A also shows links between the data applications 2208, 2210 and the respective web services systems 2212, 2214 and coaching server 2216. For example, the first data application 2208 may provide CGM data to the web services system 2212. The web services system 2212 may provide CGM data to the coaching server 2216. The second data application 2210 can provide activity data describing activities of the participant 2201 to the web services system 2214. The web services system 2214 can provide the activity data to the coaching server 2216. The coaching server 2216 can provide guidance to the participant 2201. The guidance can be in any of the forms described herein including, for example, as described in FIGS. 12A, 12B, 12C, via a chat bot such as illustrated at FIG. 17, etc. In various examples, the guidance is provided via the first data application 2208. For example, the first data application 2208 can provide a user interface for providing guidance, such as, for example, the user interface of FIGS. 12A, 12B, 12C, 17, etc.

FIG. 22C is a flowchart showing one example of a process 2270 that can be executed in the system 2200A of FIG. 22A to display CGM data at the activity sensor 2204. The process 2270 includes three columns 2271, 2273, 2275. The column 2271 includes operations executed by the first data application 2208. The column 2273 includes actions executed by the second data application 2210. The column 2275 includes actions executed by the activity sensor 2204.

At step 2272, the first data application 2208 receives CGM data from the continuous glucose monitor sensor 2202. The CGM data can include, for example, glucose data such as an estimated glucose value and/or metadata as described herein. At step 2274, the first data application 2208 generates a CGM message 2277. Generating the CGM message 2277 can include generating a data structure including the CGM data. The first data application 2208 can encrypt the data structure using a cryptographic key. Any suitable encryption technique can be used.

In some examples, the first data application 2208 also adds an error detection code to the CGM data. The error detection code is data that can be used to verify the CGM data. The first data application 2208 generates the error detection code based on the CGM data to be included in the CGM message 2277. The error detection code is a data value smaller than the CGM data that can be used by the second data application 2210, as described herein, to verify that CGM data has been accurately transmitted. Some error detection code techniques allow the second data application 2210 to correct transmission errors in the CGM data. Any suitable error detection technique can be used. In some examples, a cyclic redundancy check (CRC) technique is used. The error detection code can be encrypted or not encrypted.

At step 2274, the first data application 2208 sends the CGM message 2277 to the second data application 2210. For example, the first data application 2208 can provide the CGM message 2277 to an operating system of the user computing device 2206. The operating system can deliver the CGM message 2277 to the second data application 2210. In examples where the CGM data is encrypted, the it may not be readable by the operating system and/or any other applications that may intercept the CGM message 2277 between the first data application 2208 and the second data application 2210.

The second data application 2210 receives and processes the CGM message 2277 at step 2278. Processing the CGM message 2277 can include decrypting the CGM data included with the CGM message 2277. Decryption can be performed using a cryptographic key. For example, the second data application 2210 may have access to the same cryptographic key used by the first data application 2208 to encrypt the CGM data. In other examples, the first data application 2208 encrypts the CGM data using a public (e.g., non-secret) cryptographic key of the second data application 2210. The second data application 2210 can decrypt the CGM data using its private (e.g., secret) cryptographic key that is not shared. Processing the CGM message 2277 can also include using the error detection code to verify the accuracy of the CGM data in the CGM message 2277 and/or correct detected errors.

At step 2280, the second data application 2210 generates a device CGM message 2279. The device CGM message 2279 includes some or all of the CGM data for display by the activity sensor 2204. In some examples, generating the device CGM message 2279 also includes encrypting CGM data and/or adding an error correction code. The second data application 2210 sends the device CGM message 2279 to the activity sensor 2204, for example, utilizing a wireless transmitter of the user computing device 2206. For example, the second data application 2210 can send direct the device CGM message 2279 to the operating system of the user computing device 2206. The operating system can instruct a wireless transmitter of the user computing device 2206 to transmit the device CGM message 2279 to the activity sensor 2204.

The activity sensor 2204 receives the device CGM message 2279 at step 2282. The activity sensor 2204, in some examples, decrypts and/or performs error detection or correction on the CGM data included in the device CGM message 2279. At step 2284, the activity sensor 2204 provides an indication of some or all of the CGM data at an output device of the activity sensor 2204, as described herein. For example, the activity sensor 2204 can incorporate some or all of the CGM data into a user interface provided to the participant 2201.

Figure 23:
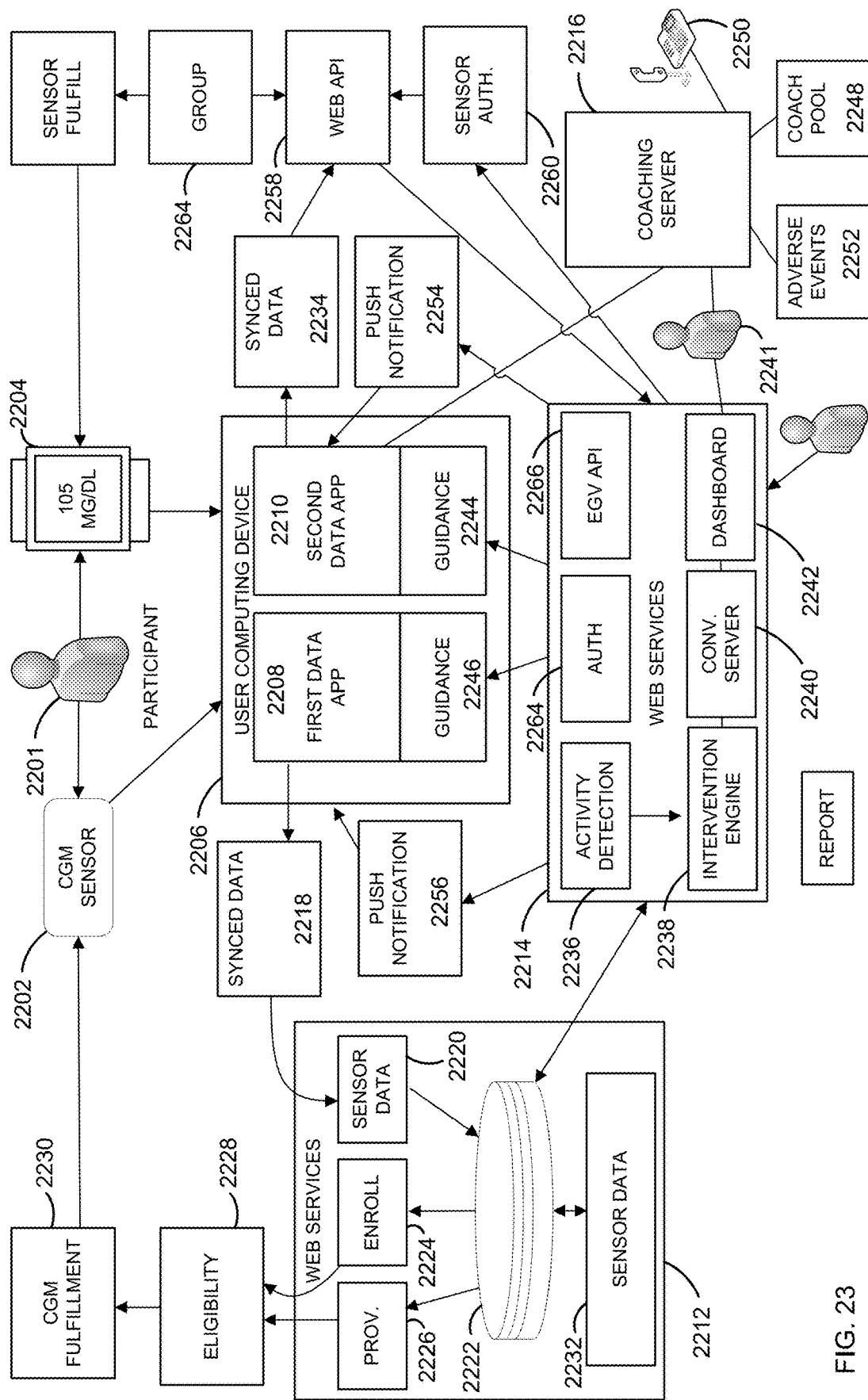
FIG. 23 is a more detailed illustration of the example system shown in FIG. 22A.

FIG. 23 is a more detailed illustration of the example system shown in FIG. 22A. In some examples, the first application 2208 may provide synced data (e.g., CGM data) 2218 which may be delivered (e.g., over a wireless or wired network) to a sensor data subsystem 2220 and passed on to a data services portion 2222 of the first web services system 2212. The first web services system 2221 may also include an enrollment subsystem 2224 and a provisioning subsystem 2226 that may provide information to an eligibility subsystem 2228, which may determine an eligibility of a subject (e.g., participant 2201) to receive a CGM sensor system, and may interact with a CGM fulfillment subsystem 2230 (which may be operated by a third party, e.g., a medical supply service) to deliver a CGM sensor to participant 2201. The data services portion 2222 of the first system 2212 may also receive another type of sensor data (e.g., low-fidelity data or blinded CGM data) from a second sensor data subsystem 2232, which may provide information that may be used to determine enrollment, provisioning, or configuration of the CGM sensor system.

The user computing device 2206 may provide activity data 2234 (e.g., via the second app 2210) to an external system such as the second system 2214, or to a web application program interface (API) 2258, which may facilitate communication with the second subsystem 2214. The second system 2214 may receive participant information, CGM information, or other information from the first system 2212.

The second system 2214 may include an activity detection system 2236, which may receive and process activity data 2234 to identify a problem state (e.g., insufficient activity), and may communicate with an intervention engine 2238, which may initiate a conversation server 2240, which may provide information to a coaching dashboard 2242. A coach 2241 may interact with the coaching dashboard 2242, e.g., to develop guidance for delivery to the participant 2201 via a guidance portion 2244 of the second app 2210 on the user computing device 2206 or via the guidance portion 2246 of the first app 2208. In some examples, the functionality of the coach 2241 is implemented using a coaching server, such as the coaching server 2216, and/or using chat bot functionality, as described herein. For example, the processes illustrated in FIGS. 26A-33 (described below) may be implemented on the user computing device 2206.

The coaching server 2216 may receive an identification of an eligible coach from a coach pool 2248 (e.g., administered by an insurance entity or other entity). The coaching sever may make a coach assignment for a particular participant, maintain call records, generate weekly coaching reports, facilitate communication with the user computing device 2206, or facilitate follow-up via a call center 2250. The coaching server 2216 may also generate a report 2252 of adverse events, if any, for regulatory, process improvement, or other purposes.

The second system 2214 (or the coaching server) may generate a push notification 2254 for delivery to the participant via the smart device (e.g., via second app 2210) or via the activity sensor (e.g., watch) 2204. The push notification 2254 may, for example, indicate that a new coach message is available. The second system 2214 may also generate a second push notification 2256, which may, for example, communicate CGM information, such as a message or guidance about glucose concentration level information, or information about provision, delivery, application (e.g., on the body of participant), replacement, scheduling (e.g., when or how long to wear), or use of a CGM sensor.

The second system 2214 may also include an authorization system 2262, which may for example provide authorization to the first app 2208, second app 2210, or both, or may provide information to an activity sensor authorization system 2260 for use of the API 2258 (e.g., to "activate" an activity sensor on the system.) The second system 2214 may also include a glucose level application program interface (API) 2266, which may receive glucose information (e.g., CGM information or sensor information or an estimate thereof) from the first system 2212 and may communicate the received information (e.g., 105 mg/dL) to the activity sensor 2204 for display to the participant.

The system may also include a group system 2264, which may for example include group information, such as an identification of participants, which may be used in the web API 2258 or for sensor fulfillment to facilitate delivery of an activity sensor 2204 to the participant 2201.

Any of the systems shown in FIGS. 22A and 23 may be implemented as a hardware system, a software module or application, or a combination thereof. The interaction of the various systems and subsystems may improve the delivery of guidance or sensors or both to the participant to improve patient management and promote positive clinical outcomes.

Figure 24:
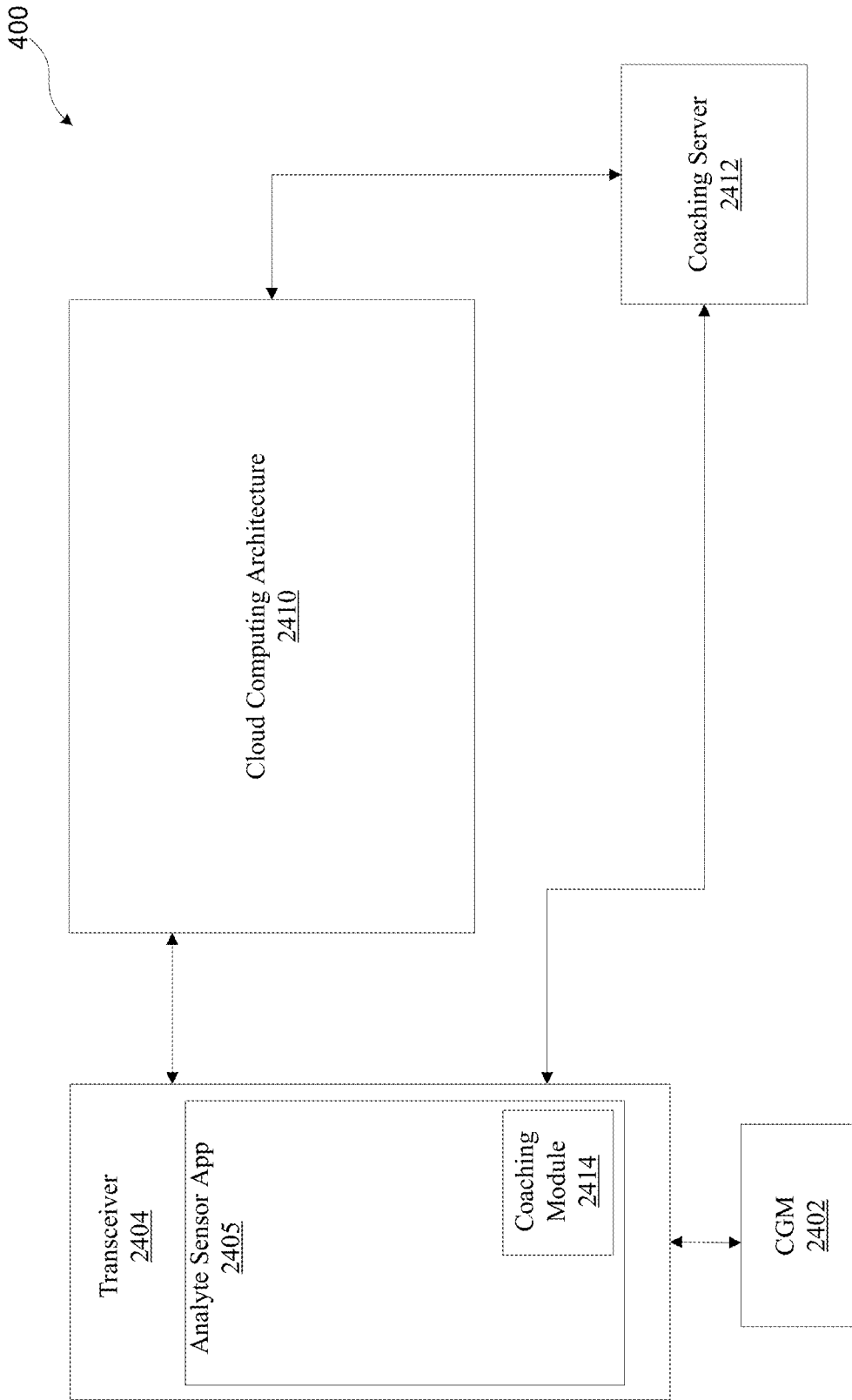
FIG. 24 illustrates an example system that may be used in connection with implementing embodiments of the disclosure.

FIG. 24 illustrates an example of a continuous glucose monitoring (CGM) system 2400 in which coaching personnel operate the coaching server 2412 to support and provide coaching services to patients who use the CGM system 2400. Some references to the coaching server 2412 may refer to the personnel operating the coaching server 2412. The CGM system 2400 can include a continuous glucose monitor (CGM) 2402 to transmit glucose monitoring data to a transceiver 2404. The transceiver 2404 can be a dedicated display device or a smart phone or other display device configured to send/receive data and communications within the CGM system 2400. The transceiver 2404 can transmit some or all patient's analyte data to a cloud computing architecture 2410 for future reference, further processing, record keeping or other purposes relevant to managing or improving patient's health.

The cloud computing architecture 2410 can include one or more health data servers configured to receive patient's analyte data. The transceiver 2404 and/or cloud computing architecture 2410 are capable of receiving patient's analyte data and generating self-referential data structures from which more meaningful patient analyte data may be displayed or analyzed. For example, the CGM 2402 readings can be used to generate a self-referential data structure for displaying patient's analyte data in a meaningful and easy to understand graphical display to be used by the patient and/or coaching personnel operating coaching server 2412. The display self-referential data structure can contain tables encoded with flagged analyte sensor data such that the self-referential data structure can be used to independently generate various analyte trend displays on demand without querying multiple databases to gather data needed to generate a desired graphical display.

In some aspects in accordance with the systems, devices and methods of the present disclosure, health-related and non-health related data are aggregated, structured, and/or transformed for intelligently producing outputs including new analytical data constructions, displays, and controls of the system's devices and devices of other systems. Such health-related information can include glucose and related data (for example, insulin, meal, activity, etc.), and non-health related data can include location data, user demographic data, etc. Implementations in accordance with such aspects of the present technology are perceived to improve the operation of the system, for example, by reducing complexities in data processing and data transmissions between devices, reducing the amount of data and processing algorithms to be stored and operated, and thereby speeding up the performance of the systems as described herein. Moreover, implementations in accordance with such aspects of the present technology are envisioned to improve the ability of users to manage their diabetes or other disorders with continuous analyte monitoring.

Some advantages of the described method and system can include the following. The self-referential data structure obviates the need for the processor to search for and recall the necessary information from various parts of the system to generate graphical displays. Otherwise, for example, without the self-referential data structures, the processor would have to search, query and/or call various parts of the system every time the user requests a different graphic or requests a modification of the displayed graphic. As such, the self-referential data structure improves the operation of the system by reducing complexities in data processing and data transmission between various parts of the system. For example, using the self-referential data structure, the system does not have to store or process additional algorithms, e.g., such as pattern recognition algorithms, to produce outputs such as displays to convey pattern information to the user. Additionally, self-referential data structures can reduce the amount and frequency of data to be transmitted for the purpose of generating graphical displays. Associated processing or graphing algorithms to be stored and operated are also accordingly reduced and the performance of the system is increased.

The transceiver 2404 can run an analyte sensor application 2405. The analyte sensor application 2405 can facilitate the connection between the coaching personnel 2412 and the patient using the CGM system 2400 as well as provide other services related to the CGM system 2400, such as providing alarms, displays, monitoring, storage and other functions. When appropriate legal and privacy permissions are obtained, the coaching personnel 2412 can have access to patients' data on transceiver 2404 or the cloud computing architecture 2410 to better support patients in management of their diabetes. The analyte sensor application 2405 can include a coaching module 2414, which can handle tasks associated with providing automated or semi-automated coaching to the patient.

Figure 25:
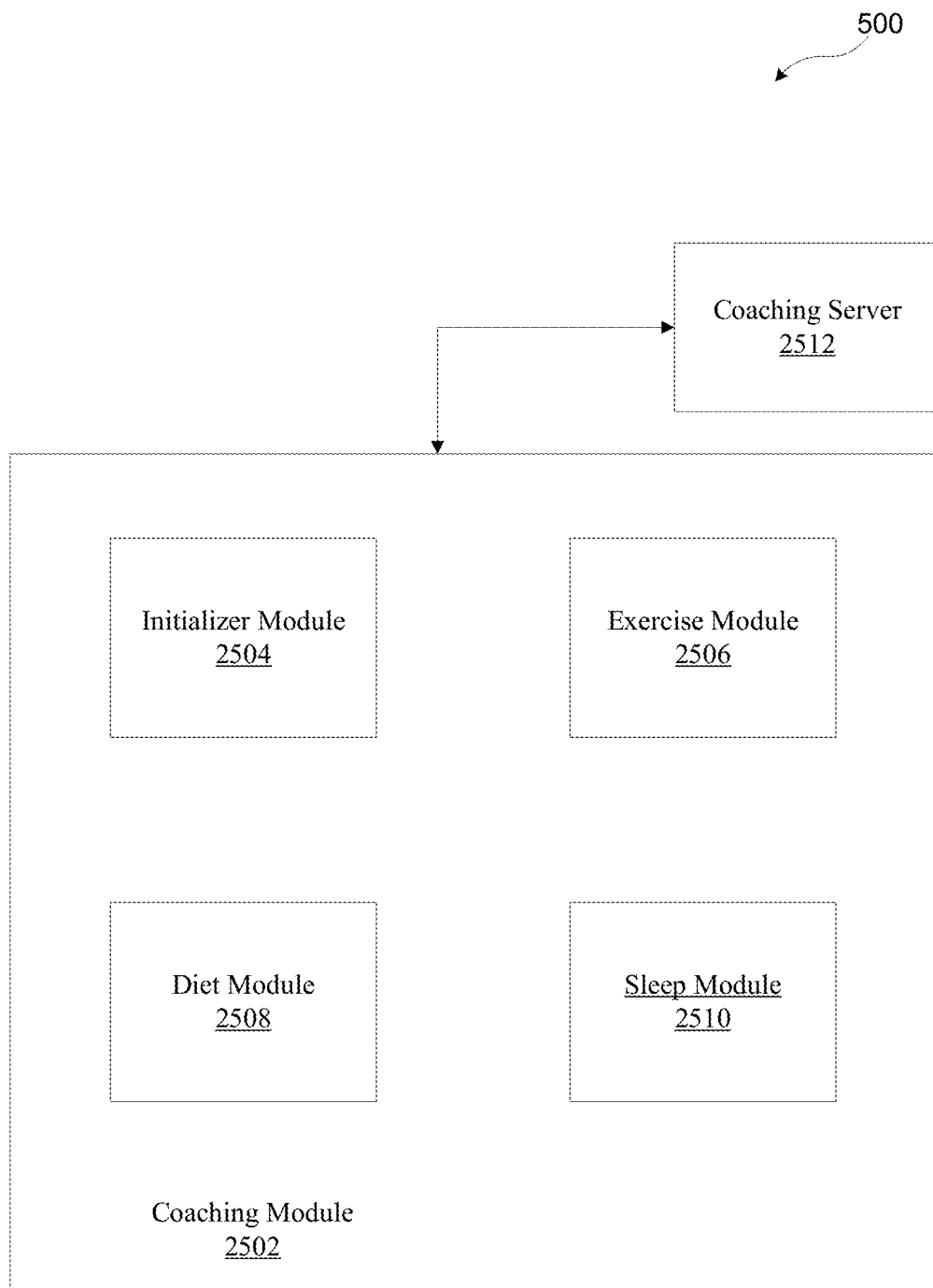
FIG. 25 illustrate an example of an automated or semi-automated coaching system, which can be used with the embodiment of FIG. 4.

FIG. 25 illustrates an example coaching system 2500, which can be used to implement automated and semi-automated coaching services for users of CGM system 2400. The coaching system 2500 can include a coaching module 2502. The coaching module 2502 can include subroutines, programs, algorithms providing coaching assistance to patients in one or more areas affecting the patient's health. For example, the coaching module 2502 can include an initializer module 2504 designed to introduce a patient to available sub-coaching modules and initiate the patient in one or more of those modules; an exercise module 2506 designed to encourage and coach the patient in engaging in movement and physical activity; a diet module 2508 designed to help the patient better understand the relationship between meal choices and blood glucose levels; and a sleep module 2510 designed to encourage and coach the patient in obtaining quality sleep while monitoring and managing glucose levels to avoid diabetic complications. The described sub-coaching modules are intended as examples and are not meant to be limiting. Persons of ordinary skill in the art can envision other sub-modules of the coaching module 2502, which can provide support, education, monitoring and coaching of different skills or activities beneficial to the management and improvement of diabetes. The coaching module 2502 can be in communication with a coaching server 2512 to provide coaching services to the patients of the CGM system 2400. The coaching server 2512 may be in part or in whole operated by human personnel trained in coaching diabetes patients.

The coaching module 2502 and its sub-modules provide coaching by proposing an activity, by creating a commitment to perform the activity (e.g., by scheduling a time and/or a place to perform the activity), by setting goals (e.g., by requesting the patient commit to performing the activity for a desired number of repetitions, or by refraining from an activity for a number of days, etc.), by monitoring the results (e.g., by examining one or more relevant glucose trend graphs), by eliciting alternative approaches to an activity in the case of suboptimal results (e.g., going for walks closer to the meal time if PPW glucose levels are not improving despite walks) and by repetition. The coaching module 2502 provides alarms, scheduling, reminder and follow up services to continuously encourage and monitor the patient's progress, interest and engagement. The coaching module 2502 can provide congratulatory messages in case of good results, encouraging and/or motivating messages when the results are mediocre, and it can alert the coaching personnel when the results are alarming or subpar.

Initializer Module

Figure 26A:
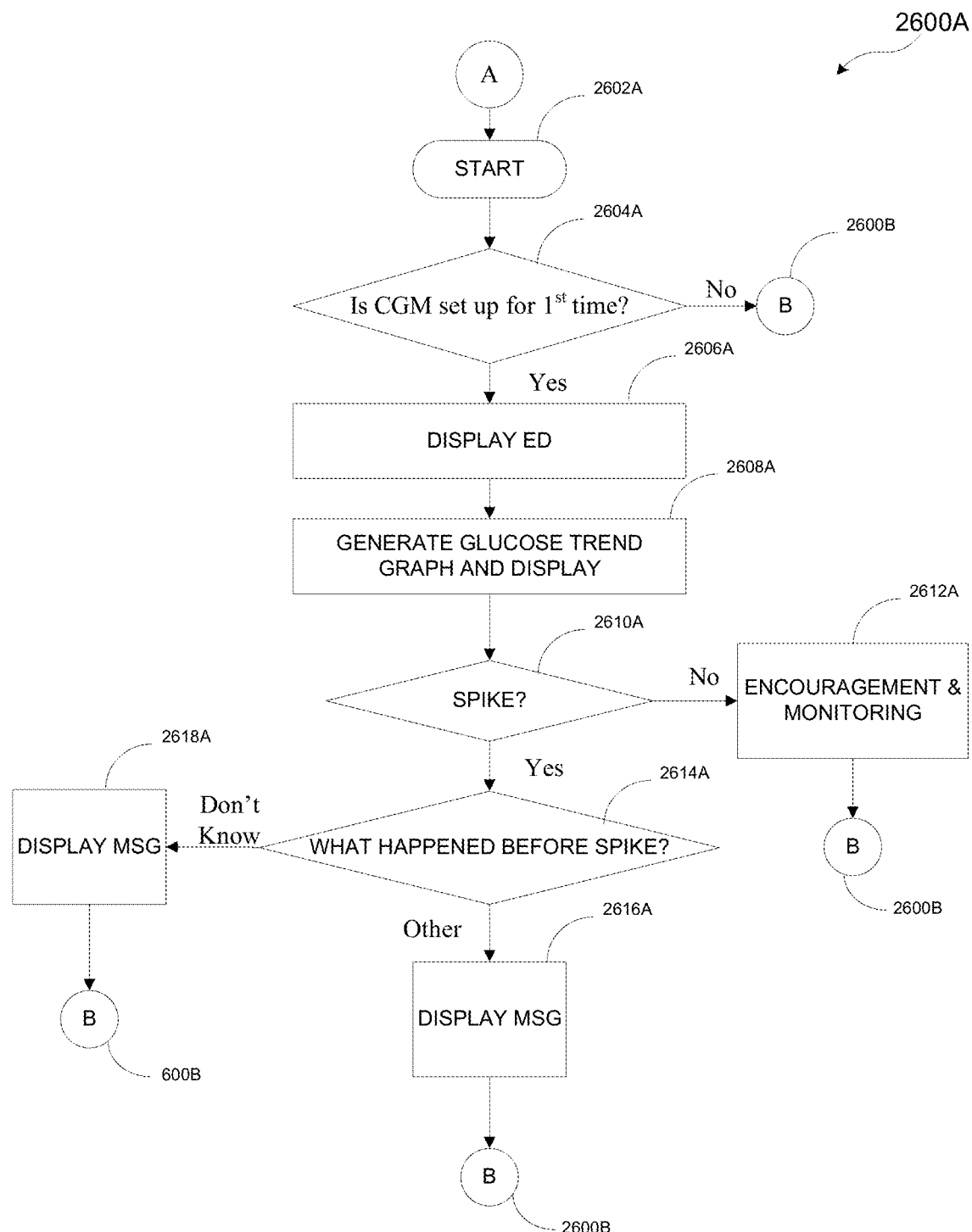
FIGS. 26A and 26B are flow illustrations of example processes to initiate a patient with automated or semi-automated coaching system of FIG. 5.

When a patient is newly set up with a CGM system 2400, an opportunity exists to also set up the patient with automated coaching and provide preliminary general or specific education on diabetes and techniques and approaches to living with diabetes. FIG. 26A illustrates an example process 2600A executed by the initializer module 2504. The process 2600A can start at the step 2602A via an action of the patient (for example, by inputting a desire to run or enroll in the coaching program via a touch screen or other input devices connected with the analyte sensor application 2405). The process 2600A can start automatically when the analyte sensor application 2405 detects a new patient. At the step 2604A, the process determines whether a new patient has set up a new CGM device. If the answer is no, the process 2600B of FIG. 26B will be executed. If the answer is yes, the process 2600A moves to the step 2606A by displaying a message containing general educational information about the blood glucose level, its meaning, its behavior and the aims of the coaching program. The coaching module 2502 and its sub-modules may use colloquial and/or simple conversational language to remove the possibility of confusion, elicit more interest in the coaching program and to create a friendly and relaxed attitude and relationship between the patients and the coaching program. For example, the displayed information at the step 2606A can include the following: "your blood sugar level doesn't remain constant, it changes. Sometimes it goes up, even way up; and sometimes it goes down."

The process then moves to the step 2608A by generating a graphical display of the patient's analyte data (e.g., a glucose trend graph related to the patient's glucose levels over the past few hours). Along with the graphical display of the patient's analyte data, the process can display an educational graphics demonstrating what may be considered a "spike" or excursion in analyte data. The educational graphics can include animation, text, or other visual indications to convey information to the patient, display the patient's glucose trend graph, and if not available, a sample general glucose trend graph to the patient. When available the initializer module 2504 can query and recall a self-referential dataset related to the patient's recent past and generate an analyte trend graph from the self-referential dataset and display that graph to the patient. The self-referential dataset may be recalled from the storage on the transceiver 2404 or the cloud computing architecture 2410.

In the step 2610A, the process can invite the patient to examine her analyte trend graph and determine whether a spike or excursion in the analyte data can be observed. If the answer is no, the process moves to the step 2612A by displaying a message or graphics congratulating the patient and encouraging the patient to continue to monitor her blood glucose levels and take healthy actions. The process then moves to the process 2600B of FIG. 26B. If at the step 2610A, the patient indicates observing a spike or undesirable excursion in the analyte data, the process 2600A moves to the step 2614A by asking the patient whether she can recall the events or circumstances before the spike or undesirable excursion occurred. The patient is therefore encouraged to think and recall the patient's choices, circumstances or environment and develop an awareness of what influences her health. If the patient recalls that the event E occurred prior to the spike, the process moves to the step 2616A and a message is displayed emphasizing the relationship between the event E and the patient's blood glucose level and encouraging the patient to take note of this relationship next time the event E occurs. The process then moves to the process 2600B of FIG. 26B. If the patient does not recall what occurred prior to the observed spike in the analyte data, the process 2600A moves to the step 2618A. A message is displayed encouraging the patient to utilize the tools and sub-modules provided by the coaching module 2502 to learn how various activities, circumstances and life events affect blood glucose levels. The process then moves to the process 2600B of FIG. 26B.

Consider an example in which a patient is experiencing early morning highs glucose events. The coaching module may access data (e.g., at the cloud computing architecture 2410, indicating that the patient has been prescribed medication to be taken in the early morning. The process 2600A can proceed as described above to step 2610A, where the early morning spikes are detected. At step 2614A, the coaching module 2502 can query the patient about whether the patient is still taking prescribed medication at the appointed time in the morning. If the patient is taking the medication, the coaching module 2502 can be configured to display a message of encouragement (for example, at step 2618A) or to further query the patient about other events that may have caused the spike. If the patient is not taking the medication, the coaching module 2502 can be configured to display a message, at step 2616A, encouraging the patient to resume taking the medication.

Figure 26B:
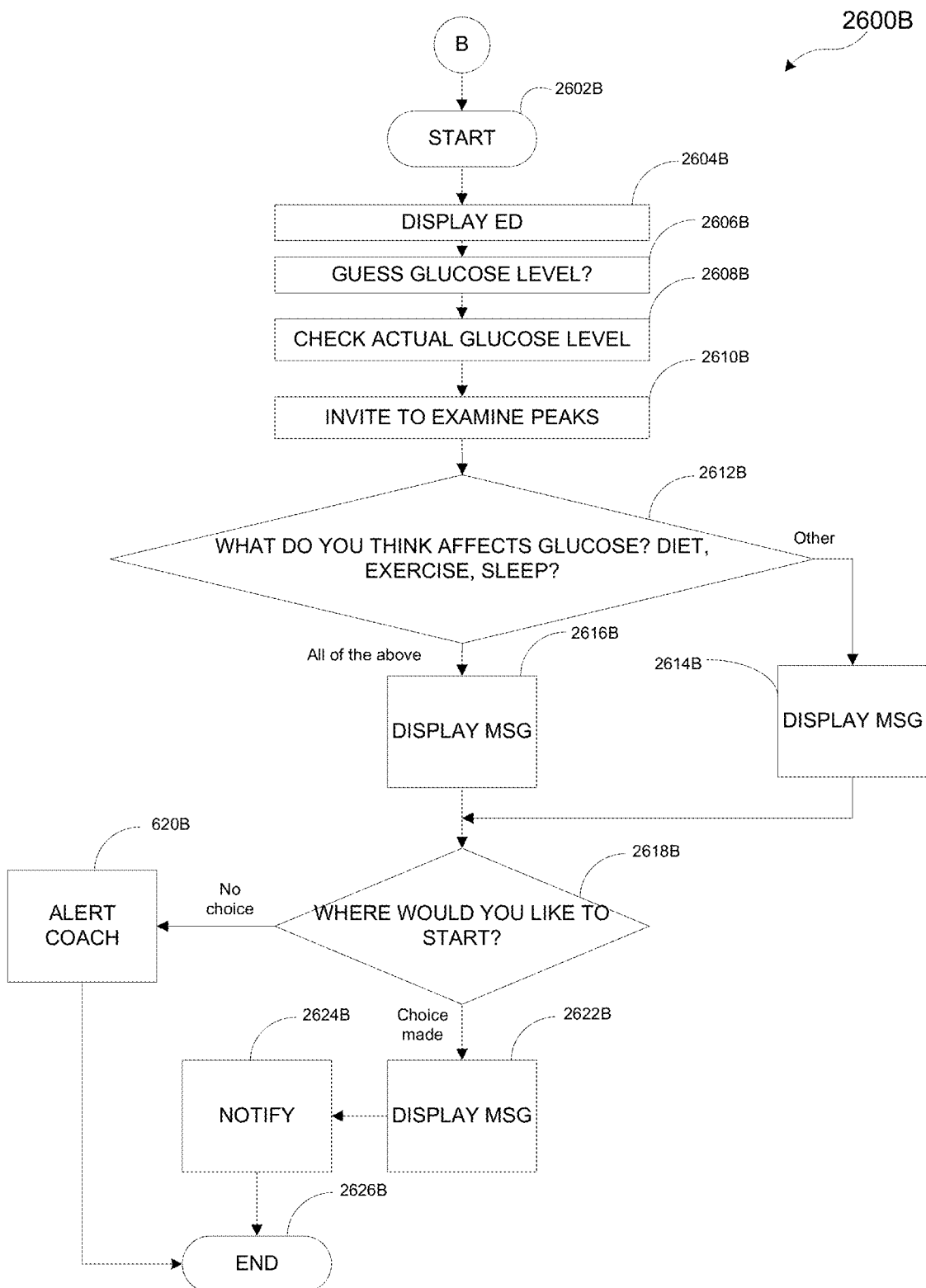

FIG. 26B illustrates an example process 2600B executed by the initializer module 504. The process starts at the step 2602B and moves to the step 2604B by displaying educational information on safe ranges of blood glucose level. The patient can be provided with information on multiple safe blood glucose levels depending on the circumstances the patient might encounter. For example, the displayed educational information can say "safe blood sugar ranges vary based on the individual's circumstances, but broadly blood sugar should be between 70 and 180 after a meal and it should drop below 130 in a couple of hours after a meal. Before bedtime it should be between 100 and 140." The displayed educational information on safe ranges can caution the patient to use custom ranges if they are prescribed by the patients' physician. The displayed educational information can further contain an introduction to tools available with the coaching module 2502 to support the patient in keeping her blood glucose levels in safe ranges.

The patient is further encouraged to check her blood glucose levels often, and more frequently after activities that affect blood glucose levels. For example, the patient is coached to check her glucose readings before and after taking a meal, physical activity, when stressed or before going to bed. Another recommended time to check one's glucose level is when calibrating the CGM 2402. If the patient can be accustomed to checking her blood glucose levels more frequently, the patient will have a better chance and increased opportunity to observe and learn the effects of various choices and activities on her blood glucose level. The process can move to the step 2606B by asking the patient to guess what her current blood glucose level might be. Fun and engaging questions can be used by the coaching module 2502 and its sub-modules to encourage further engagement from the patient. The patient can input an estimate of her current blood glucose level via an interesting and engaging graphical display, for example a sliding bar, scroll bar, text and arrows or other visuals designed to work with touch screens or voice recognition technology. The process then moves to the step 2608B by presenting the patient with her recent glucose trend graph, which can include an indication of actual current glucose level. The patient is invited to examine the trend graph and observe her current blood glucose level and its recent levels.

Next the process moves to the step 2610B inviting the patient to examine the glucose graph to see whether any spikes or excursions in the glucose data can be observed. Next the process moves to the step 2612B by asking the patient what activities affect blood glucose level. The patient can be presented with multiple choices, for example, "diet, exercise, sleep or all of the above." In this example, all of the provided answers are true, so the correct response is "all of the above." If the patient responds with an answer other than "all of the above," the process moves to the step 2614B displaying an encouraging message indicating that all choices affect blood glucose level and that the coaching module can coach the patient through each activity step by step. The process then moves to the step 2618B. If the patient responds by indicating that all the listed activities affect blood glucose, the process moves to the step 2616B by displaying a congratulatory and encouraging message to the patient for choosing the right answer. The displayed message can state that the coaching module can coach the patient through learning and understanding each listed factor and its effect on the patient's blood glucose level. The process then moves to the step 2618B asking the patient which activity or skill the patient would like to learn about first. If the patient makes no choice or indicates a lack of interest or motivation, the process moves to the step 2620B and a coaching alert ticket is generated and transmitted to the coaching personnel via coaching server 2512. The process then ends at the step 2626B. If the patient indicates an interest by choosing one of the activities or skills presented, the process moves to the step 2622B by displaying a message congratulating the patient on her enthusiasm. The process then moves to the sub-module chosen by the patient. For example, if exercise, diet or sleep are chosen, correspondingly, the exercise module 2506, the diet module 2508 or the sleep module 2510, respectively, are recalled and executed by the coaching module 2502. The process then moves to the step 2624B and the coaching server 2512 is updated to reflect the patients chosen activity module. In some embodiments, the coaching personnel operating the coaching server 2512 can manually assign a sub-coaching module and update the coaching server 2512 accordingly. The process then ends at the step 2626B.

Generally, the coaching module 2502 can be configured to generate a coaching alert ticket and notify the coaching personnel when the patient's responses and interactions with the patient indicate a lack of interest, motivation or commitment. Living with diabetes can be challenging. Responses showing lack of interest and commitment can be indicators of depression or a sign that the patient may need psychological or mental help to deal with challenges of living with diabetes. As part of generating a coaching alert ticket, the coaching module 2502 or its sub-modules can gather relevant contextual information to assist coaching personnel to efficiently and promptly attend to the patient. For example, depending on the activity for which the patient demonstrates a lack of enthusiasm, the coaching module 2502 can present questions to the patient and obtain answers relevant to providing coaching and counseling on that activity.

The coaching module can further annotate, label and categorize the patient's contextual information so the coaching personnel can more efficiently and effectively provide counseling and coaching services. For example, if the patient has initiated and predicted a healthy activity but has failed to achieve her predicted goals, the contextual information used for building the coaching alert ticket can include a label stating, "committed but unable to achieve." On the other hand, if the patient refuses to schedule an activity and her response indicate a lack of confidence in the proposed activity, the contextual information can include a label stating, "the patient does not believe in the proposed activity." The coaching personnel operating the coaching server 2512 can examine the contextual information labels for efficient and timely review of the patient's history and her present issues. In some embodiments, the coaching personnel operating the coaching servers 2512 can specialize in particular areas of providing coaching and assistance to the patients. For example, some coaching personnel may specialize in and possess special training in providing counseling and coaching to patients that lack discipline in monitoring their diets. The contextual information labels can be used to route coaching alert tickets to coaching personnel specializing in handling the underlying issue.

An overall theme informing the interactions between the coaching module 2502 and the patient is to encourage engaging with the CGM system 2400 and the coaching module 2502, by for example using the tools provided and observing the analysis and recommendations of the tools in relation to the patient's blood glucose levels. Such engagement can increase the patient's understanding of the disease and improve the patient's intuitive response to her condition.

Exercise Module

Figure 27:
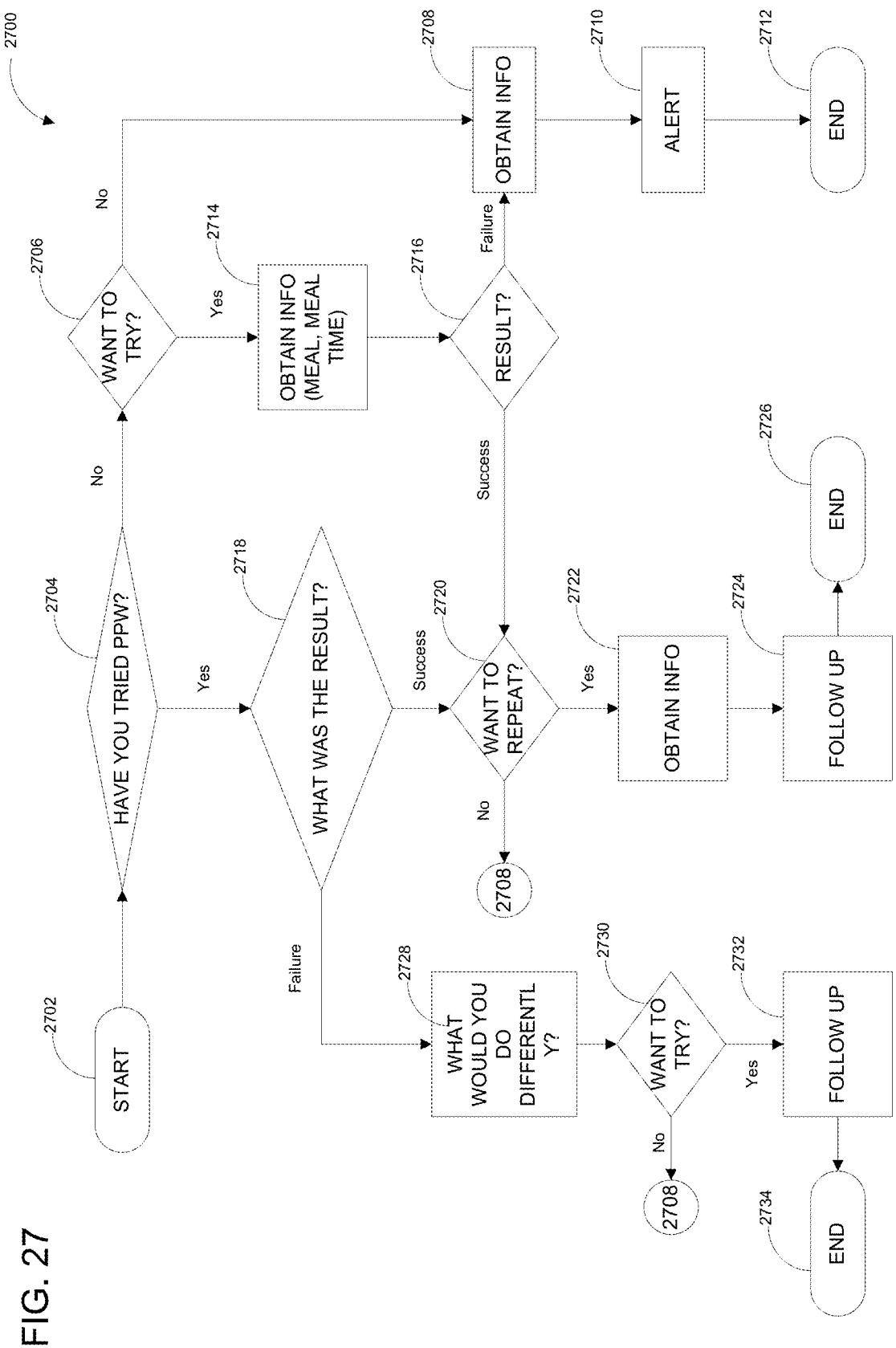
FIG. 27 is a flow chart illustration of an example process to initiate an exercise module.

The coaching module 2502 can include an exercise module 2506 to encourage and coach patients to engage in physical activity and observe the benefits and correlation between physical activity and improved glucose levels. FIG. 27 illustrates a process 2700 which can initiate a patient with an automated or semi-automated coaching system submodule focused on exercise and physical activity. Movement and physical activity beneficial to diabetes patients can be as simple as going for walks after meals. As Post Prandial Walk (PPW) can be an area of focus for coaching, process 2700 of FIG. 27, process 2800 of FIG. 28 and process 2900 of FIG. 29 will be described in relation to PPW. Persons of ordinary skill in the art can envision other types of physical activity or movement which can be implemented using the processes 2700, 2800 and 2900 without departing from the spirit of the described technology.

The process 2700 starts at the step 2702. The exercise module 2506 can educate the patient on the beneficial effects of physical movement on blood glucose level and recommend exercise as a method of keeping blood glucose levels within a safe range. The process moves to the step 2704, where the patient is asked about her prior experience with a recommended physical activity such as PPW. If the patient indicates she has not tried PPW, the process moves to the step 2706 asking if the patient would like to choose a meal in the future to practice PPW. If the patient indicates a lack of interest, the process moves to the step 2708, where additional contextual information is obtained from the patient, or from the patient's records in the cloud computing architecture 2410 and/or the transceiver 2404. At the step 2710 a coaching alert ticket is generated and transmitted to the coaching server 2512 and the coaching personnel are notified. The process ends at the step 2712. The same process can be repeated, and a coaching alert ticket generated and transmitted if at any time the patient's responses indicate a lack of interest or motivation for managing or improving her health.

If the patient indicates an interest in trying PPW, the process moves to the step 2714, where the patient is asked to choose a meal for practicing PPW and time by which the exercise module 2506 can check back with the patient on the result. A follow up reminder is scheduled based on the patient's response. When the time for follow up comes, the process moves to the step 2716 and the patient is asked whether the patient could practice PPW as scheduled and what the results were. If the patient's response indicates a failure to practice or unexpected results after having practiced PPW, the process can perform the steps 2708 and 2710 to collect information, build and transmit a coaching alert ticket. The process ends at the step 2712. If the result of the PPW was a success, the process moves to the step 2720 asking the patient if she would like to repeat the success attained by scheduling more PPW sessions.

The success or failure of the PPW sessions can be determined from presenting questions to the patient and presenting multiple choice option responses such as "what happened to your blood sugar level?", "went up more slowly," "didn't go as high as expected," "didn't change," "went up a little," or "went up a lot." A group of possible patient's responses can be categorized as success and if those responses are detected, the process 2700 can be routed based on a successful result. Similarly, some responses may be categorized as failed results and if those responses are detected, the process 2700 can be routed accordingly. In some embodiments, the success or failure of PPW or other proposed activity may be determined by querying the patient's records in the cloud computing architecture 2410, the transceiver 2404 or both to automatically determine whether the patient's glucose levels were in a safe region after the scheduled PPW session. Alternatively, to encourage the patient to learn to interpret her glucose trend graph or other available glucose data, the patient might be asked to determine the success or failure of the PPW sessions by examining her glucose data manually. The stored analyte data in the CGM system 2400 can be used as a secondary check and the patient can be prompted to reevaluate her response or the stored data if discrepancies are detected. Similarly, whether the patient could practice PPW may be determined by presenting a textual or graphical question to the patient or by querying the transceiver 2404, for example for global positioning system GPS data if the transceiver 2404 is retrofitted with that option.

If the patient does not indicate an interest in scheduling more PPW sessions, the process can perform the steps 2708 and 2710 to collect information, generate and transmit a coaching alert ticket. The process then ends at the step 2712. If the patient indicates an interest in repeating the achieved success by scheduling more PPW sessions, the process moves to the step 2722 and schedules a future PPW session based on the patient's desired time and meal. The process then moves to the step 2724 where the scheduled PPW session is used to execute a follow-up process 2800 as will be described in relation to FIG. 28. The process 2700 then ends at the step 2726.

As described, in the step 2704 of the process 2700, the patient is asked whether she has tried PPW before? If the patient's response is yes, the process moves to the step 2718 asking the patient what the result of the patient's prior experience with PPW has been. If the patient indicates a failure or unexpected result, the process can move to the step 2728 asking the patient whether there is anything the patient can do differently to make PPW more successful. The patient can respond by free text or by interacting with a menu or other visual interface, such as choosing from a drop-down menu or radio buttons from a menu of prepopulated responses (e.g., "take a longer walk," "walk more quickly," "walk closer in time to eating"). The process can move to the step 2730 asking the patient whether she would like to try one or more of the alternative approaches the patient has just indicated. If the patient responds with lack of interest, the process can perform the steps 2708 and 2710 to collect information, generate and transmit a coaching alert ticket. The process then ends at the step 2712. If the patient responds positively, the process can move to the step 2732 and schedule a future PPW session based on the patient's desired time and meal. The scheduled PPW session is used to execute the follow-up process 2800 as will be described in relation to FIG. 28. The process 2700 then ends at the step 2734.

Figure 28:
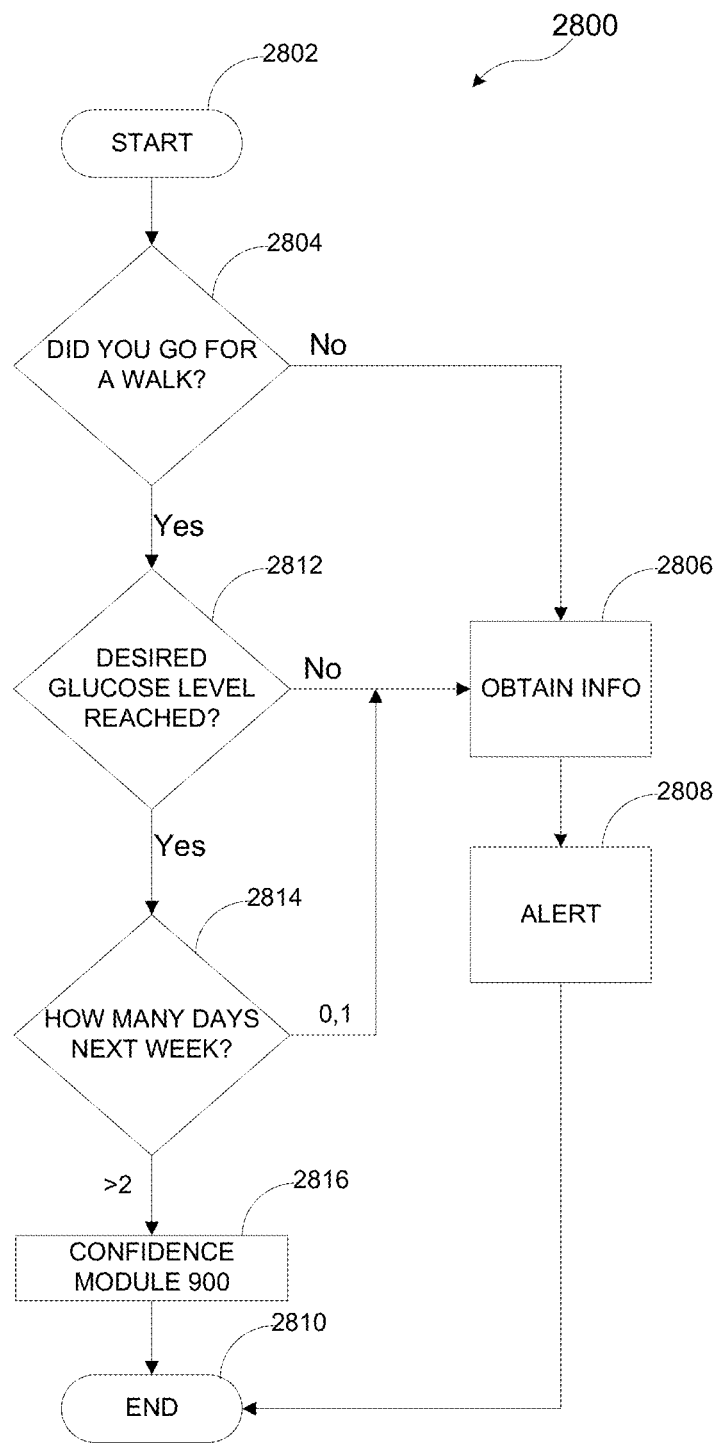
FIG. 28 is a flow chart illustration of an example process to implement a follow up module.

FIG. 28 illustrates a process 2800 for performing follow-ups on the progress of the patient who has been introduced and scheduled for PPW or other recommended activity beneficial to diabetes management. The process 2800 starts at the step 2802. After a prescheduled time for a PPW session has arrived or after a predetermined time after a scheduled time, the process moves to the step 2804 asking the patient whether she could practice PPW as scheduled. If the patient responds negatively, the process can perform the steps 2806 and 2808 to collect context information, built and transmit a coaching alert ticket. The process then ends at the step 2810.

If the patient indicates she could practice PPW as scheduled, the process moves to the step 2812 asking the patient whether her blood glucose level was within safe or desirable ranges after a PPW session. If the answer is no, the process performs the steps 2806 and 2808 to collect information, build and transmit a coaching alert ticket. The process then ends at the step 2810. If the answer is yes, the process moves to the step 2814 asking the patient how many days she predicts she can practice PPW. If the patient's response is less than a minimum threshold (e.g., 0 or 1 day), the process can perform the steps 2806 and 2808 to collect information, build and transmit a coaching alert ticket. The process then ends at the step 2810. If the answer is equal or more than a minimum threshold (e.g., 2 days), the process can move to the step 2816 where the number of predicted days for PPW activity is saved and transmitted to a confidence assessor/booster process 2900 as will be described in relation to FIG. 29. The process then ends at the step 2810.

Consider an example in which a patient has an acceptable A1C level, as indicated previously and stored at the cloud computing architecture 2410. In this example, the patient also has indicated previously, at step 2806 of a previous execution of the process 2800, that an injury has preventing the patient from performing desired exercise. This data may also be stored in the cloud computing architecture and used in a subsequent execution of the process 2800. For example, at step 2804, the patient can be queried about whether his injury has healed in addition to whether the patient has been able to take the PPW.

Figure 29:
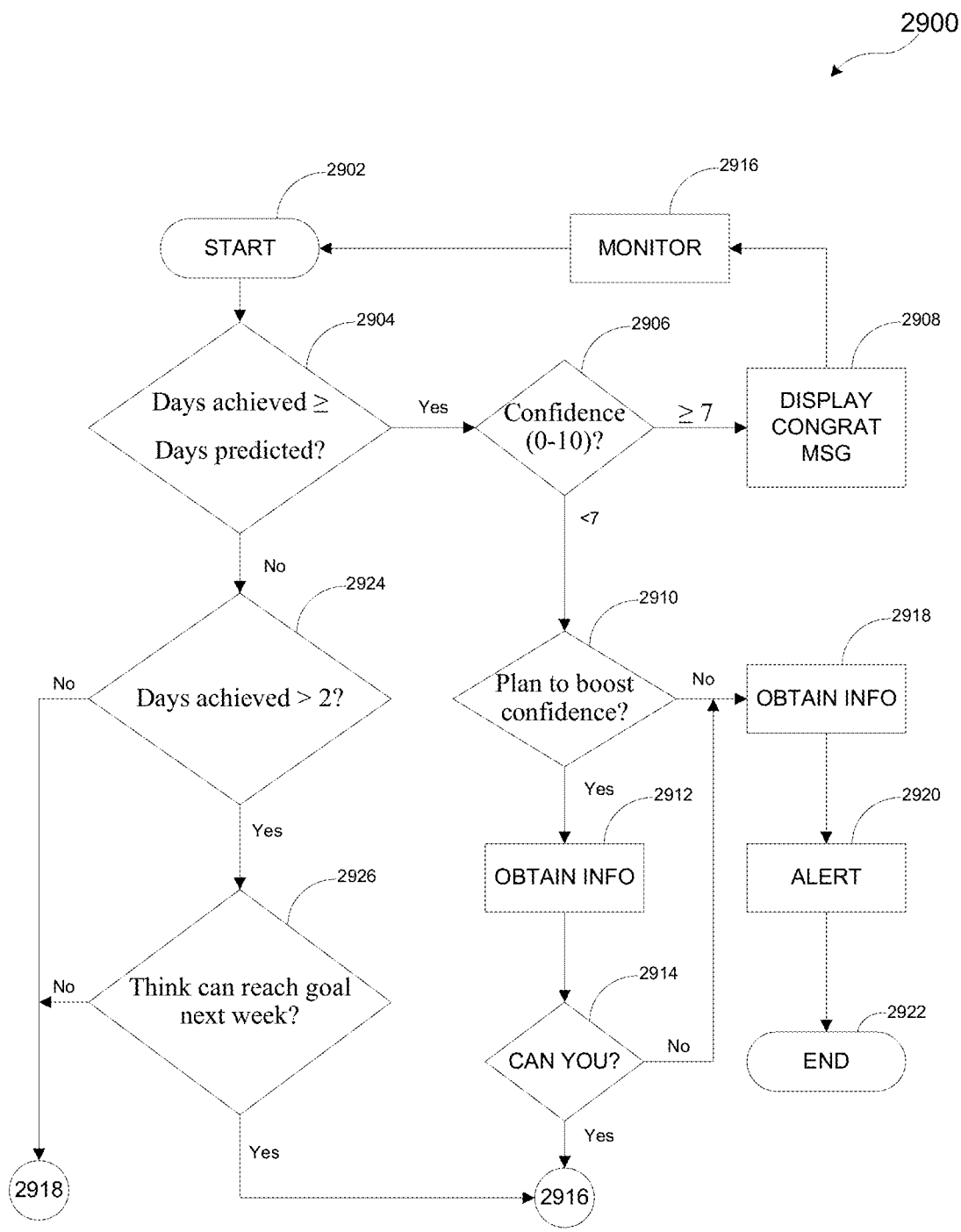
FIG. 29 is a flow chart illustration of an example process to implement a confidence assessor/booster module.

FIG. 29 illustrates an example process 2900 which can be executed by the exercise module 2506 to further follow up, assess or boost the patient's confidence in PPW practice or other proposed activity beneficial to diabetes. The process starts at the step 2902. The exercise module 2506 can keep track of the number of days in which the patient practices PPW. The process moves to the step 2904 to determine whether the days the patient practiced PPW are equal or greater than the days the patient predicted she would practice PPW. If the answer is yes, the process moves to the step 2906 asking the patient on a predetermined scale (e.g. on a scale of 0-10) how confident the patient is that she can practice PPW over the next 7 days. If the patient's confidence level is more than a predetermined minimum confidence number (e.g., 7), the process moves to the step 2908 displaying a message congratulating the patient on her resolve and commitment. Then the process can return to the step 2902 and repeat the process 2900 after one week or another predetermined period. If the patient's confidence level in her ability to practice PPW is less than the predetermined confidence number (e.g. less than 7), the process can move to the step 2910 and ask whether the patient can do anything to increase her confidence level for being able to achieve the scheduled number of PPW practices. If the answer is no, the process performs the steps 2918 and 2920 to collect information, build and transmit a coaching alert ticket. The process ends at the step 2922. If the answer is yes, the process moves to the step 2912 asking the patient to input the patient's plan for succeeding in practicing the scheduled number of PPWs. The process can move to the step 2914 asking the patient whether she believes she can follow through with the plan. If the answer is yes, the process moves to the step 2916 where the patient's PPWs are tracked daily or obtained after a predetermined time (e.g., one week) and then the process moves to the step 2902 and the process 2900 is repeated. If the answer is no, the process can perform the steps 2918 and 2920 to collect information, build and transmit a coaching alert ticket. The process then ends at the step 2922.

If, at the step 2904 it is determined that the days the patient practiced PPW is less than the scheduled number, the process moves to the step 2924. If the number of days the patient practiced PPW is less than or equal to a predetermined minimum number (e.g., less than or equal to 2 days), the process performs the steps 2918 and 2920 to collect information, build and transmit a coaching alert ticket. The process then ends at the step 2922. If the number of days the patient practiced PPW is more than the predetermined minimum number (e.g., more than 2 days), the process moves to the step 2926 asking the patient whether she believes she can achieve the scheduled number of PPW practice days. If the answer is yes, the process moves to the step 2916 where the patient's PPWs are tracked daily or obtained after a predetermined time (e.g., one week) and then the process moves to the step 2902 and the process 2900 is repeated. If the answer is no, the process performs the steps 2918 and 2920 to collect information, build and transmit a coaching alert ticket. The process then ends at the step 2922.

Figure 30:
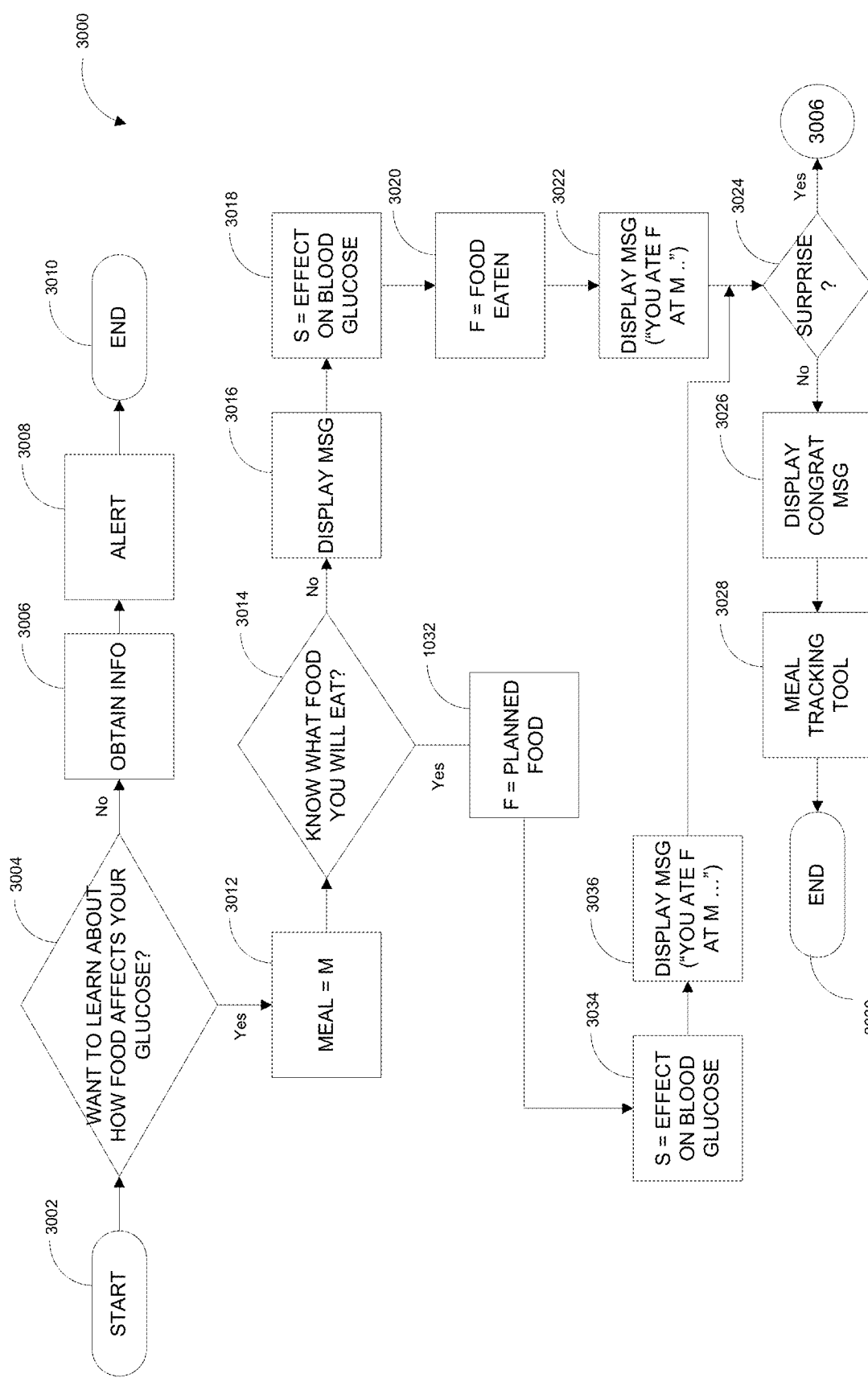
FIG. 30 is a flow chart illustration of an example process to implement a diet module.

The coaching module 2502 can include a diet module 2508 to encourage and coach patients to understand and learn the effects of their diet choices on their blood glucose levels and diabetes. FIG. 30 illustrates a process 3000 which can initiate a patient with an automatic or semi-automatic coaching system sub-module focused on diet. The process 3000 starts at the step 3002. At the step 3004, the patient is asked whether she would like to learn how different foods and diet choices can affect her blood glucose levels. If the answer is no, the process performs the steps 3006 and 3008 to collect information, build and transmit a coaching alert ticket. The process then ends at the step 3010. If the answer is yes, a message to the patient is displayed encouraging the patient's interest and engagement. The message can further remind the patient on the connection and correlation between diet and blood glucose levels. The message can encourage the patient to continue to review her blood glucose readings to learn more about how different diet choices affect her glucose readings.

The process moves to the step 3012 asking the patient to choose a meal time M to start learning about the effects of diet on blood glucose levels. The patient's chosen meal time M, can be stored and a reminder scheduled to follow up with the patient. The process moves to the step 3014 asking the patient whether she knows what she will be eating for the chosen meal. If the answer is no, the process moves to the step 3016 displaying an encouraging message and informing the patient that she can track what she eats and observe the effects on her blood glucose level using the tools provided in the CGM 2400 system. Shortly or a predetermined time after the scheduled meal time M, the process moves to the step 3018 where the patient is asked what the effect of consuming the meal was on her blood glucose level. The patient can enter text or choose an answer from an array of possible scenarios, such as "went way up and stayed there," "went up but came down quickly," "did not change much," or "went down." The patient's response can be stored in a variable, S. The process moves to the step 3020 asking what the patient ate at the scheduled meal M. The patient can enter free text or choose from a menu of available options to describe the meal she has had, and her answer can be stored in a variable F.

The process moves to the step 3022 displaying a message linking the patient meal M and her blood glucose level S via a text block or other graphical or visual displays. The message can be a sentence populated with the values stored in the variables M, F and S. For example, the message can be constructed from the sentence "you ate <F> at the meal <M> and your blood glucose level <S>." If F=chocolate cake, M=breakfast and S=went way up and stayed there, the displayed message can read: "you ate chocolate cake at the meal breakfast and your blood glucose level went way up and stayed there." Various messaging formats and scenarios can be employed to strengthen the patient's understanding and learning the effects of food and diet on her blood glucose level.

The process then moves to the step 3024 asking whether the patient is surprised by the result. If the answer is no, the process can move to the step 3026 where the patient is congratulated for keeping track of her glucose level after a meal and invited to continue checking her glucose levels after a meal. The process then moves to the step 3028 where the patient is invited to work with a meal tracking tool to track more meals and their effects on her glucose levels. The meal tracking tool will be described in relation to the process 3100 of FIG. 31. The process then ends at the step 3030. If the patient is surprised by the result of her glucose reading and her answer in the step 3024 is yes, the patient may need additional or individualized coaching on the types of foods and diets and their effect on diabetes. The process can perform the steps 3006 and 3008 to collect information, build and transmit a coaching alert ticket. The process then ends at the step 3010.

If at step 3014, the patient knows what she will be having for a scheduled meal time M, the process moves to the step 3032 storing the patient's planned meal in a variable F. Shortly, or a predetermined time after a scheduled meal time M, the process moves to the step 3034 and the patient is asked what the effect of consuming food F at meal M was on the patient's blood glucose level. The patient's response can be stored in a variable S. The process moves to the step 3036 displaying a message constructed from variables M, F and S. For example, the message can be constructed from the sentence "you ate <F> at the meal <M> and your blood sugar <S>" and variables F=grilled fish, whole wheat toast and garden salad, M=Lunch and S=went down. The displayed message can read: "you ate grilled fish, whole wheat toast and garden salad at lunch and your blood sugar went down." Next the process moves to the step 3024 to encourage the patient to use the meal tracking tool of FIG. 31 to deepen her understanding of the correlation between diet and blood glucose.

Figure 31:
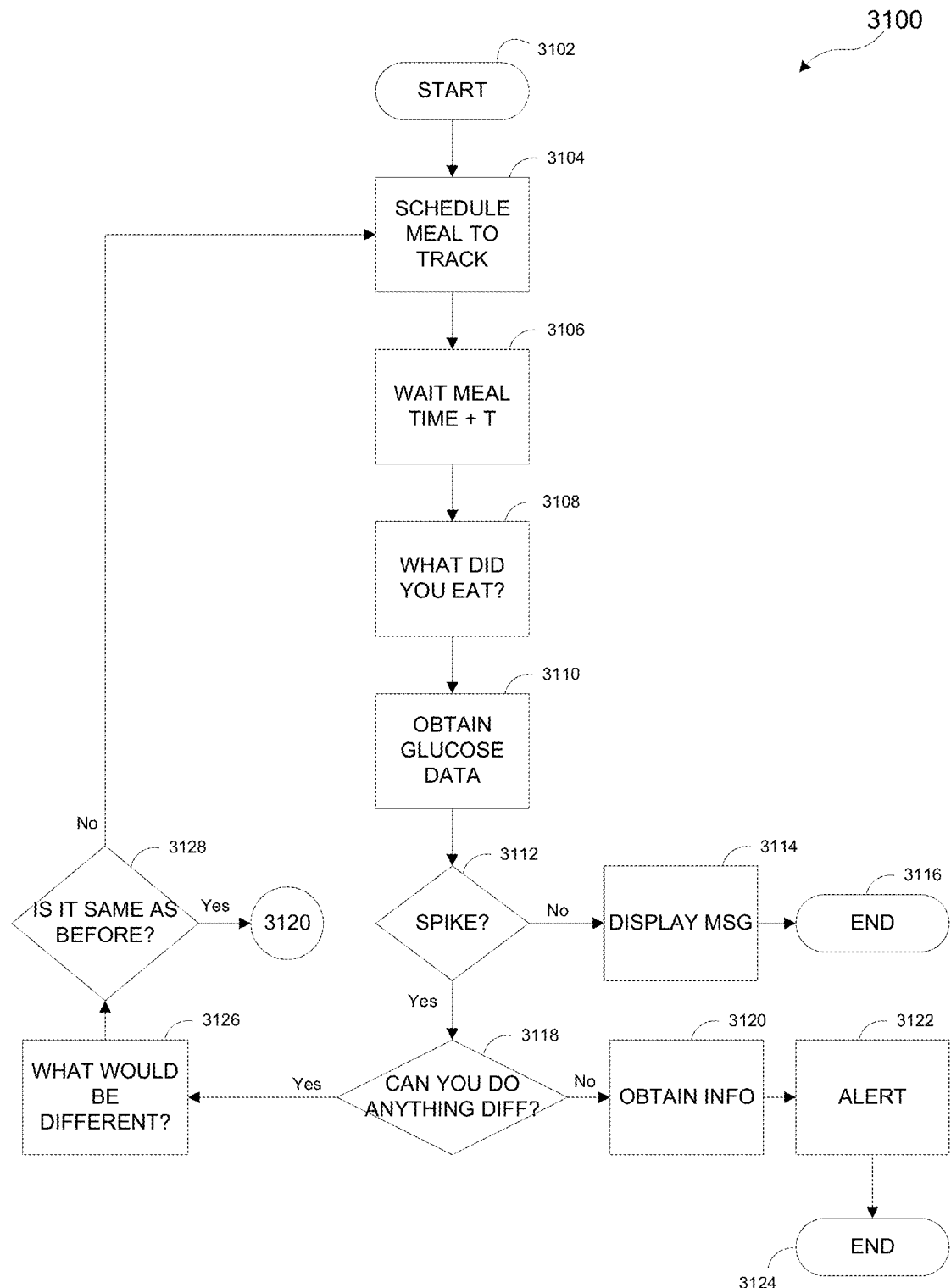
FIG. 31 is a flow chart illustration of an example process to implement a meal tracking module.

FIG. 31 illustrates an example process 3100 which can be executed by the diet module 2508 to implement a meal tracking tool to encourage and coach patients in understanding the relationship between their diet and their blood glucose level. The process 3100 starts at the step 3102 via an input from the user indicating an interest in starting the operations of the tool or by a complementary process or tool such as the process 3000. The process 3100 moves to the step 3104 asking the patient to schedule a meal M to track. The patient's choice is stored, and a reminder is scheduled for a predetermined period T after the scheduled meal M. T can be for example 1 to 2 hours. The process moves to the step 3106 waiting a predetermined time T after the meal M. The process moves to the step 3108 asking the patient what she ate at the scheduled meal M and storing the patient's response in a variable F. Next, the process moves to the step 3110 where the patient's glucose data is obtained for a period before meal M and a time period after the meal M plus the predetermined time T. The glucose data for the relevant time period can be obtained from the patient, where the patient examines a glucose trend graph of the relevant time or obtained from other parts of the CGM system 2400 such as the transceiver 2404 or the cloud computing architecture 2410. The glucose data is presented to the patient and the process moves to the step 3112 asking whether the patient observes a spike or undesirable excursion in the glucose data. In other embodiments, the diet module can automatically examine and scan the glucose data for excursions by comparing the stored glucose values to a high or low threshold. If there is no spike or undesirable excursion in the glucose data, the process moves to the step 3114 displaying a message encouraging the patient to continue checking her blood glucose level and learn how to eat safely. The message can for example read: "OK, each time you check your glucose after eating, you'll learn more about how to eat safely and enjoy food."

If the patient observes a spike or excursion in the blood glucose level and her response in the step 3112 is yes, the process moves to the step 3118 asking the patient whether she can eat another food that might have a better effect on her blood glucose level. If the patient shows a lack of interest or knowledge about what can be done differently, the process can perform the steps 3120 and 3122 to collect information, build and transmit a coaching alert ticket. The process then ends at the step 3124. If the patient responds with indicating an ability to make a better meal choice, the process moves to the step 3126 asking more questions of the patient to help determine the patient's resolve and interest. For example, at the step 3126, the patient can be asked to input in the system what the patient can do differently next time (e.g., what the patient meal choice might be in the future). The process moves to the step 3128, where it is determined whether the patient's planned choice is similar or different than her prior choice leading to an undesirable excursion in blood glucose level. If the patient's planned choice is same or similar to her previous choice, the process can perform the steps 3120 and 3122 to collect information, build and transmit a coaching alert ticket. The process then ends at the step 3124. If the patient's choice is different than her prior choice indicating a plan aimed at maintaining safe blood glucose level, the process can move to the step 3104 to schedule follow up meal tracking sessions and the process 3100 is repeated.

Figure 32:
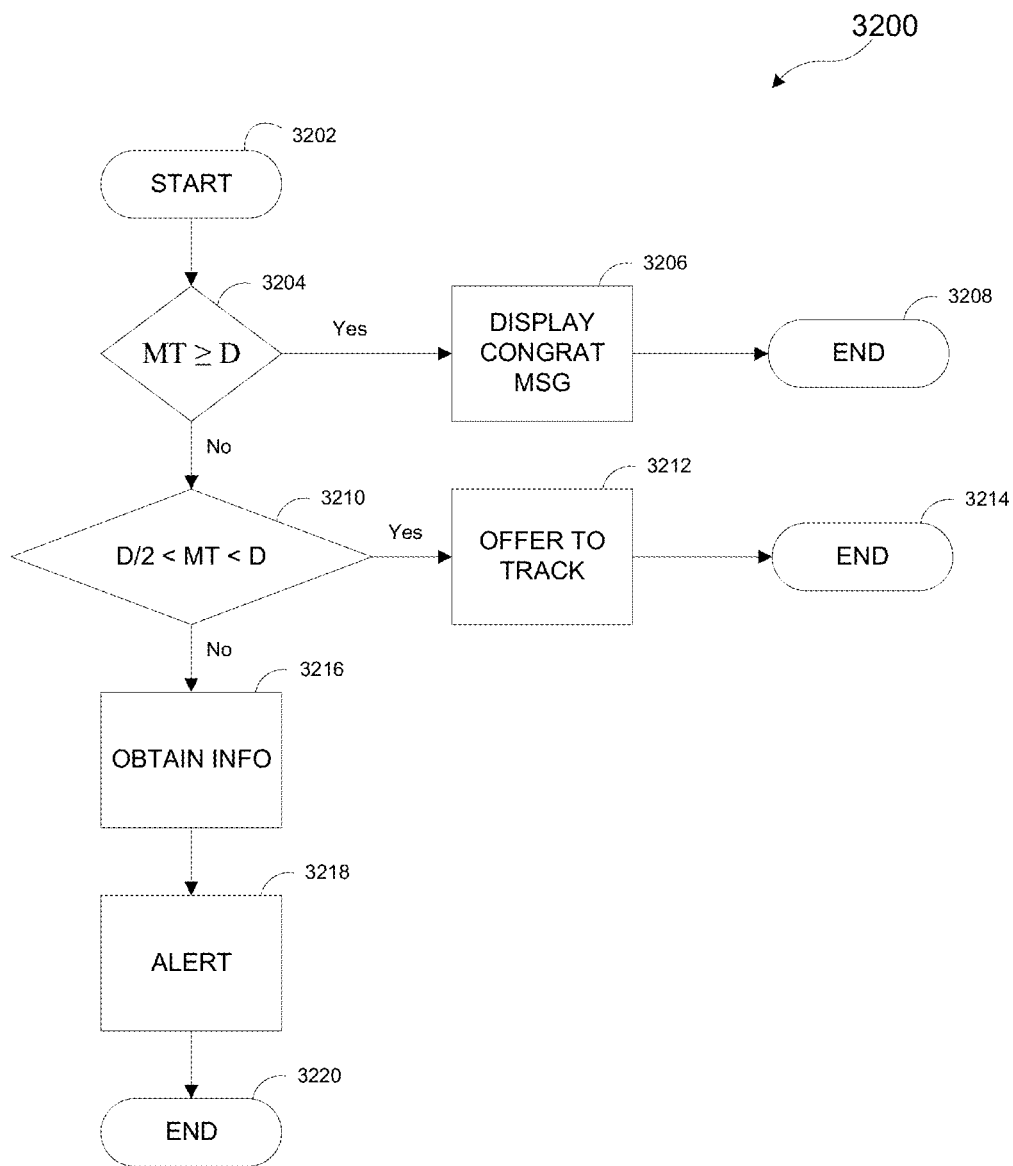
FIG. 32 is a flow chart illustration of an example process to implement a module designed to encourage the use of the embodiment of FIG. 11.

FIG. 32 illustrates an example process 3200 which can be implemented in the diet module 2508 to encourage and coach patients to increase their efforts in monitoring their blood glucose after meals by using the meal tracking tool described in relation to FIG. 31. The process 3200 can be run automatically on a predetermined time interval (e.g., weekly) or run manually by the patient starting at the step 3202. The meal tracking tool implemented via the process 3100 can be configured to keep track of and store the number of times the tool was used and/or the number of meals the patient tracked in a variable MT (Meals Tracked). The system can by default designate a desirable number of tracked meals in a variable D or query the patient, a patient's guardian or health care professional and/or the coaching personnel for the number of meals a patient is expected to track and store that value in the variable D. At the step 3204, the patient's Meals Tracked MT is compared against the desired or expected number of meals to be tracked D. If the Meals Tracked MT is equal to or exceeds the expected tracked meals D, the process moves to the step 3206 displaying a congratulatory message and the process ends at the step 3208. At the step 3210, if the Meals Tracked MT is less than the expected number D, but more than half of the expected number D, the process moves to the step 3212, where the diet module 2508 can be configured to send reminders, offers and invitations to the patient to track meals and check glucose data. The process then ends at the step 3214. If the meals tracked MT are less than or equal to half of the desired number D, the patient might need more individualized coaching to increase her efforts in tracking meals and checking glucose data. The process can perform the steps 3216 and 3218 to collect information, build and transmit a coaching alert ticket. The process then ends at the step 3220.

Sleep Module

Figure 33:
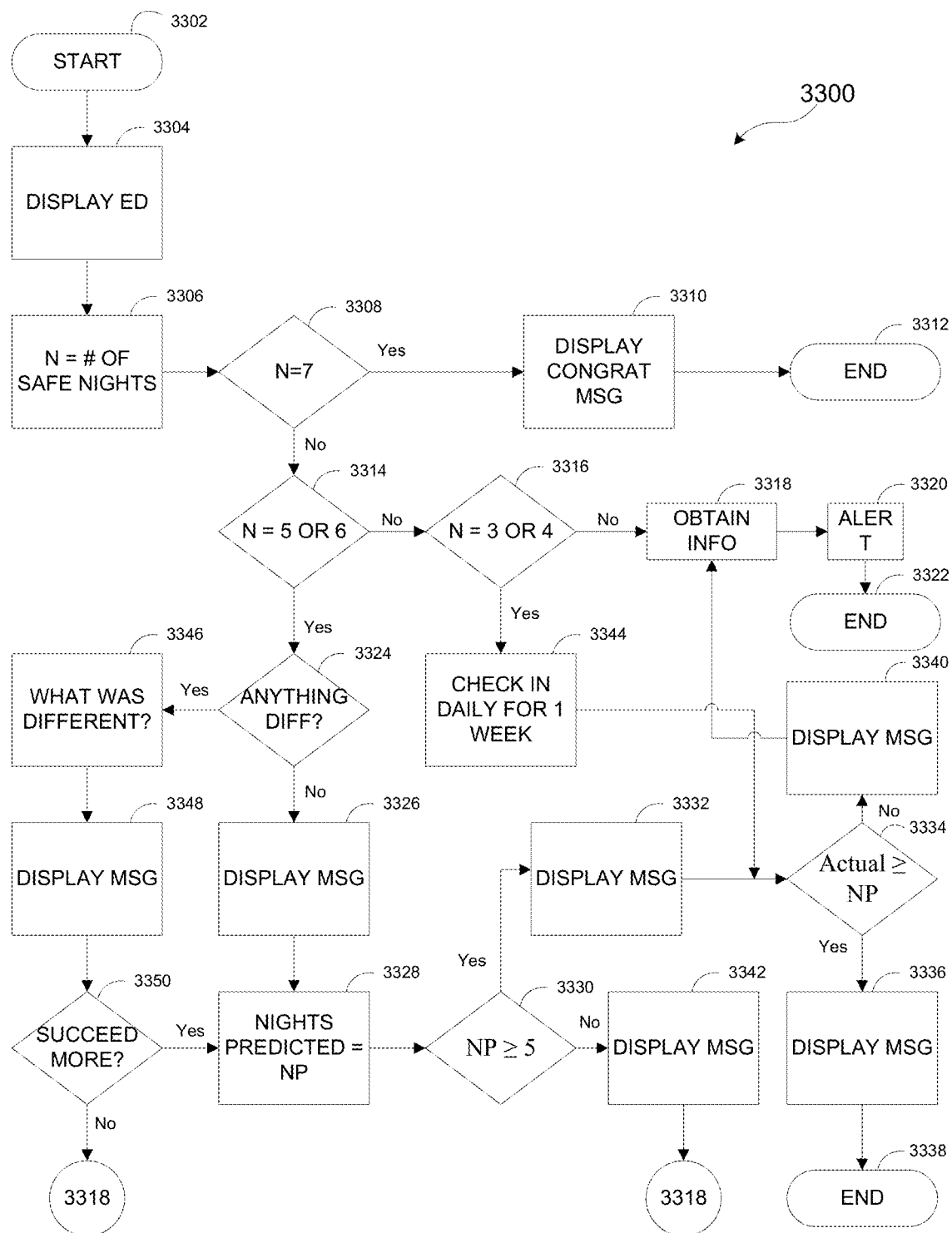
FIG. 33 is a flow chart illustration of an example process to implement a sleep module.

FIG. 33 illustrates an example process 3300 which can be implemented by the sleep module 2510 to encourage and coach patients to monitor their night time glucose behavior and better understand the beneficial effects of proper sleep on their blood glucose level. The process 3300 starts at the step 3302. At the step 3304, the process displays general and/or patient-specific data on the relationship of sleep and blood glucose. For example, such a display may read: "the better you sleep, the safer/healthier you will be. Keeping your glucose in range (e.g., 100 to 140 mg/dL) during sleep will help you sleep better and improve how you are handling diabetes." The process then moves to the step 3306. A glucose trend graph is generated from the self-referential data structures stored in the CGM system 2400 and presented to the patient. The patient is asked to examine the glucose trend graph of the past 7 nights and determine how many nights the patient's glucose levels were in a safe range during the first few hours of sleep. In some embodiments, the sleep module 2510 may automatically determine whether the patient's glucose level has been safe during a relevant period. In some examples, a machine learning technique, as described herein, can be used to generate a model of the relationship between patient sleep and blood glucose.

In the context of providing automated coaching, encouraging the patient to examine her glucose trend graph and learn how to read and correctly interpret glucose data and graphs may be more desirable than purely determining unsafe glucose excursions. Other safety and monitoring tools and modules within the CGM 2400 can more appropriately undertake those tasks. As such, within the context of providing automated coaching, the ability of the CGM system to automatically analyze the patient's glucose data can be used secondarily and to double check the patient's analysis and determination. The patient's analysis and interpretation of her glucose data can be matched against the automated analysis of the CGM system 2400 and if discrepancies are detected, the patient, the coaching personnel or other involved individuals can be notified.

At the step 3308, if the number of nights the patient's glucose level has been within a safe range, the process moves to the step 3310, where a message is displayed congratulating the patient on her approach and inviting her to continue checking night time or sleep time glucose levels and trends. The process ends at the step 3312.

At the step 3314, it is determined whether the patient's nightly glucose levels have been safe for at least 5 or 6 nights. If the answer is no, the process moves to the step 3316 to determine if the patient's nightly glucose levels have been safe for at least 3 or 4 nights. If the answer is no, the patient might need more individualized or immediate coaching assistance to better manage her blood glucose levels at sleep time. The process performs the steps 3318 and 3320 to collect information, build and transmit a coaching alert ticket. The process then ends at the step 3322.

If at the step 3314, it is determined that the patient's nightly glucose levels have been in safe ranges for at least 5 or 6 nights, the process moves to the step 3324, asking the patient whether there was something the patient had done differently in nights that her glucose stayed in safe ranges. If the patient does not recall or does not know, the process moves to the step 3326 displaying a message inviting the patient to track the nightly glucose levels for the next 7 days (or other period as may be desired based on the patient's age, history or other factors). The process moves to the step 3328 asking the patient how many nights she believes her glucose levels will stay within a safe range. The patient's response is stored in a variable NP (Nights Predicted). At the step 3330, if the Nights Predicted are more than or equal to 5 nights, the process moves to the step 3332. A message is displayed congratulating the patient on her engagement and commitment to health.

After a week delay, the process moves to the step 3334 and the patient is asked to check her blood glucose levels for the past 7 nights. If the patient's nightly glucose levels stayed within a safe range for more than or equal to the Nights Predicted NP, the process moves to the step 3336, a congratulatory message is displayed, the patient is encouraged to continue tracking night time glucose levels and the process ends at the step 3338. If the number of nights the patient's nightly glucose level remained in safe ranges is less than the Nights Predicted NP, the process moves to the step 3340 where an encouraging message is displayed acknowledging the challenges the patient might have faced and inviting the patient to discuss those challenges with her coach. The process performs the steps 3318 and 3320 to collect information, build and transmit a coaching alert ticket. The process then ends at the step 3322.

If at the step 3330 the patient predicts that her glucose levels would stay within safe ranges for less than 5 nights, the process moves to the step 3342 displaying a message inviting the patient to discuss with her coach possible challenges that might affect her ability to maintain safe nightly glucose levels. The process then performs the steps 3318 and 3320 to collect information, build and transmit a coaching alert ticket. The process ends at the step 3322.

If at the step 3316, the patient's nightly glucose levels have been within safe ranges for at least 3 to 4 nights, the process moves to the step 3344. The patient is monitored more closely by the sleep module 2510. For example, at step 3344, the patient can be prompted each morning or at some time before her sleep time whether she predicts that her nightly glucose levels will be in a safe range for that night. The process is repeated over a week period or other desirable period and the Nights Predicted NP are counted and stored. The process then moves to the step 3334.

If at the step 3324, the patient knows what had changed for her to be able to maintain safe nightly glucose, the process moves to the step 3346, where the patient is asked about what made the difference between the safe nights and other nights. The patient's response is recorded. At the step 3348 a message is displayed congratulating the patient on her proactive and engaged attitude. The process moves to the step 3350 asking the patient whether she is ready to achieve the same level of success again in having safe nightly glucose levels for the next week. If the patient's response is yes, the process moves to the step 3328. If the patient's response is no, the patient might have less confidence in her ability to maintain safe nightly glucose levels. She may need more individualized coaching to increase her confidence level. The process performs the steps 3318 and 3320 to collect information, build and transmit a coaching alert ticket. The process ends at the step 3322.

The information gathered to provide automated or semi-automated coaching (e.g., information gathered in the processes 2600A, 2600B, 2700, 2800, 2900, 3000, 3100, 3200 and 3300) can be obtained from the patient as described above or can be obtained or inferred from other data available in the CGM system 2400. For example, the patient's actions during prescheduled activities can be inferred from Global Positioning System (GPS) data of the transceiver 2404 or the patient's glucose data stored on the transceiver 2404 or the cloud computing architecture 2410. The patient can be asked to confirm whether an automatic determination of the events is correct. For example, the coaching module 2502 can automatically detect an in-range blood glucose level for a period after a PPW session. The coaching module 2502 can present a glucose trend graph of the relevant period to the patient and request the patient to confirm glucose levels were within range during that period. If appropriate permissions are obtained, the coaching module 2502 can determine a patient went for a walk during a period scheduled for PPW activity by consulting GPS data stored on the transceiver 2404. The coaching module can confirm this determination with the patient.

In some examples, an analyte sensor system can be configured to execute a high-fidelity data collection where captured data is retrieved after collection. This can be useful for patients who do not have access to a wireless network and/or do not regularly carry a smart device or other user computing device. After-collection data retrieval can also minimize or eliminate the need for the user to set up a smart device to communicate with the analyte sensor system. This can allow clinicians to provide patients with access to the analyte sensor with fewer training costs.

Figure 34:
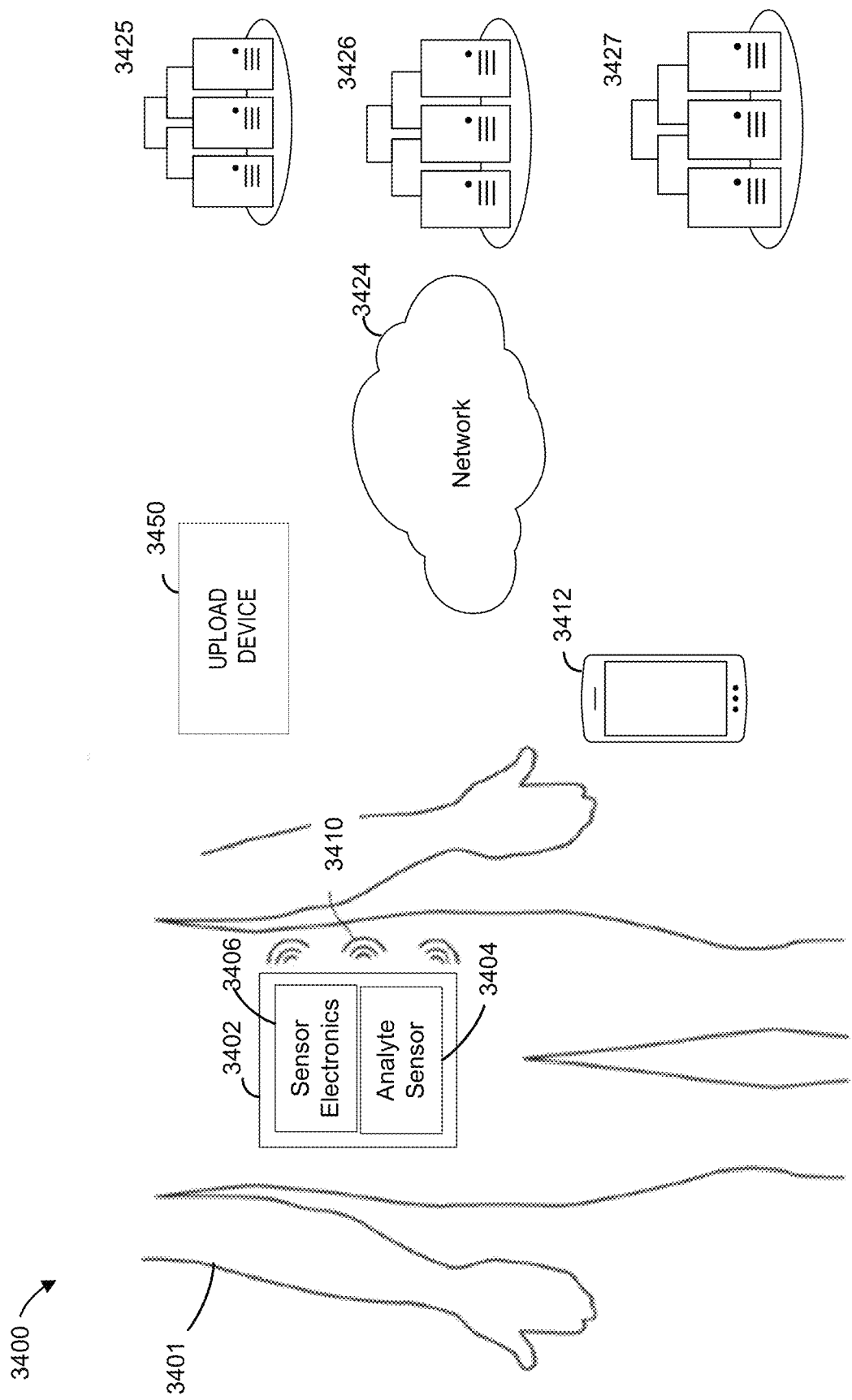
FIG. 34 is an illustration of an example system that can include an analyte sensor system configured to upload captured analyte data after collection.

FIG. 34 is an illustration of an example system 3400 that can include an analyte sensor system 3402 configured to upload captured analyte data after collection. The analyte sensor system 3402 may be coupled to a host 3401, similar to the host 101 of FIG. 1. The analyte sensor system 3402 can be similar to the analyte sensor 102 of FIG. 1. For example, the analyte sensor system 3402 can include an analyte sensor 3404, such as a glucose sensor. Sensor electronics 3406 may be similar to the sensor electronics 106 of FIG. 1. Sensor electronics 3406 can include data storage hardware for storing analyte data captured by the analyte sensor 3404. Sensor electronics 3406 can also be programmed to upload captured analyte data after collection, for example, as described herein with respect to FIGS. 35-37.

The example system 3400 includes an optional smart device 3412 that can be used, similar to the hand-held device 112, to communicate with the analyte sensor system 3402, via one or more wireless communication signals 3410. The smart device 3412 can provide the host 3401 with an indication of analyte data detected by the analyte sensor system 3402, for example, as that data is collected. In some examples, the analyte sensor system 3402 operates in a blinded mode and the smart device 3412 may be omitted.

The example system 3400 also includes an upload device 3450. The upload device 3450 can be or include any suitable computing device configured to communicate with the analyte sensor system 3402 (e.g., the sensor electronics 3406 thereof) via the wireless communication signals 3410. The upload device 3450, in some examples, is remote from the host 3401 while analyte data is collected by the analyte sensor system 3402. In some examples, the analyte sensor system 3402 (or just the sensor electronics 3406 thereof) are removed from the host 3401 after data collection and physically transported to a location of the upload device 3450. For example, the upload device 3450 can be located at a pharmacist, a clinician's office, or other suitable location. The upload device 3450 can couple to the sensor electronics 3406 and retrieve collected analyte data. The upload device 3450, in some examples, provides the downloaded analyte data to one or more of server systems 3425, 3426, 3427 via network 3424. Server systems 3425, 3426, 3427 can be similar to the server systems 125, 126, 127 described herein.

Figure 35:
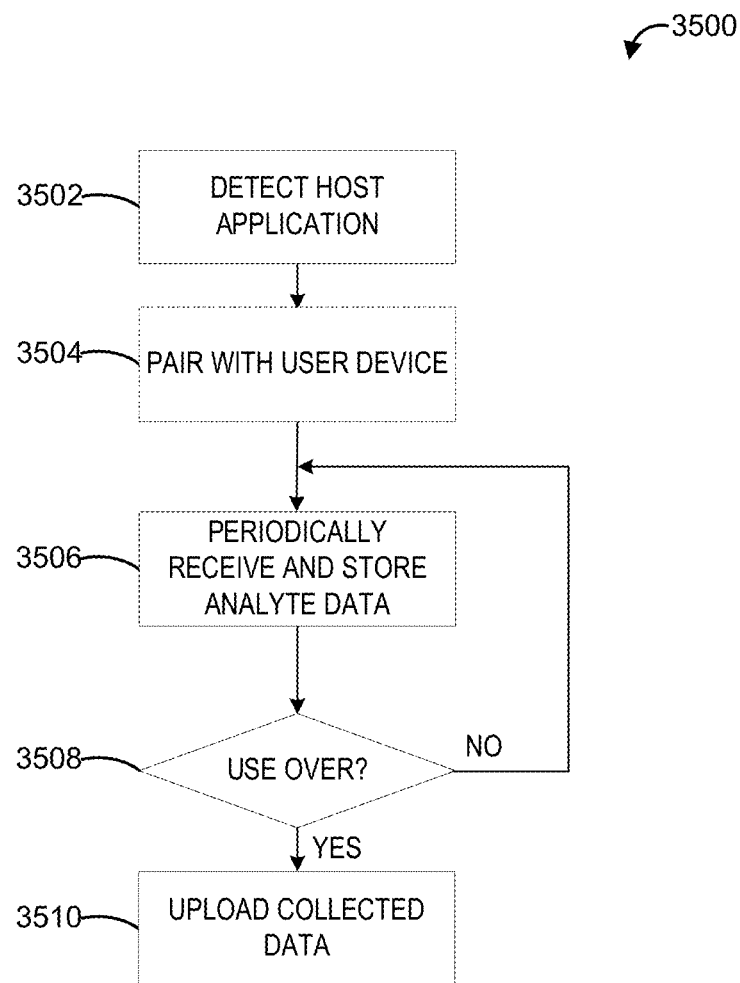
FIG. 35 is a flowchart showing one example of a process that can be executed by the analyte sensor system of FIG. 34 to collect and upload analyte data.

FIG. 35 is a flowchart showing one example of a process 3500 that can be executed by the analyte sensor system 3402 (e.g., the sensor electronics 3406 thereof) to collect and upload analyte data. At step 3502, the sensor electronics 3402 detect that the analyte sensor system 3402 has been applied to the host 3401. The detection may occur, for example, when the analyte sensor 3404 begins to provide analyte data. In some examples, the sensor electronics 3402 detects that the analyte sensor system 3402 has been applied to the host 3401 when the analyte sensor 3404 provides sensor readings above a threshold value for two different time periods. Consider an example in which the analyte sensor 3404 is a glucose sensor that is configured to capture an estimated glucose value for the patient every thirty (30) seconds. The sensor electronics 3406 may detect application of the analyte sensor system 3402 when the analyte sensor 3404 detects an estimated glucose value above a threshold value (e.g., 60 mg/dL) for two different thirty (30) second periods. In some examples, the sensor electronics 3406 detects application of the analyte sensor system 3402 when the analyte sensor 3404 detects an estimated glucose value above a threshold value (e.g., 60 mg/dL) for two consecutive thirty (30) second periods.

In some examples, the sensor electronics 3406 receive a serial number of other sensor identifier of the analyte sensor 3404, for example, to properly calibrate analyte data received from the analyte sensor 3404. The sensor electronics 3406 can receive the sensor identifier in any suitable manner. In some examples, the sensor electronics 3406 establish a wireless communication link with the analyte sensor 3404. The analyte sensor 3404 provides the sensor identifier via the wireless link. Any suitable type of wired or wireless communication link can be used such as, for example, a Bluetooth LE connection, a near field communication (NFC) connection. Also, in some examples, the analyte sensor 3404 includes a radio frequency identifier (RFID) circuit. The sensor electronics 3404 can illuminate the RFID circuit with electromagnetic radiation, which may cause the RFID circuit to broadcast the sensor identifier. At optional step 3504, the sensor electronics 3406 can establish a wireless communication session with the smart device 3412, for example, as described herein. Step 3504 may be omitted in examples where blinded analyte measurement is performed.

At step 3506, the sensor electronics 3406 periodically receive analyte data from the analyte sensor 3404 and store the received analyte data, for example, at data storage hardware in communication with the sensor electronics 3406. Analyte data can include analyte values and/or metadata describing the host 3401 and/or diagnostic data describing the performance of the analyte sensor 3404. The sensor electronics can receive and store analyte data at any suitable period such as, for example, every thirty (30) seconds, every five (5) minutes, or any other suitable period. In some examples, the sensor electronics 3406 are programmed to prompt the analyte sensor 3404 to provide analyte data. For example, such prompting can occur once per period. In examples where the sensor electronics 3406 have a communication session with the smart device 3412, the sensor electronics 3406 may also transmit some or all of the collected analyte data to the smart device 3412 for display (e.g., to the host 3401).

At step 3508, the sensor electronics 3406 determine if the use of the analyte sensor 3404 is over. The use may be over, for example, if a sensor use period has expired. For example, the analyte sensor 3404 can be configured for use during a defined use period (e.g., one week, ten (10) days, etc.). The use of the sensor can be over if the sensor has been in use for the full use period. In other examples, use of the sensor can be over if the analyte sensor 3404 has become disengaged from the host 3401 or otherwise fails. For example, the sensor electronics 3406 can determine that the analyte system 3404 has failed if it fails to receive analyte data within a defined range for more than a threshold number of measurements.

If the analyte sensor 3404 use is not over, the sensor electronics 3406 may continue to periodically receive and store analyte data at step 3506. If the use is over, the sensor electronics 3406 can enter an upload routine at step 3510. Example upload routines are described herein with respect to FIGS. 36 and 37.

Figure 36:
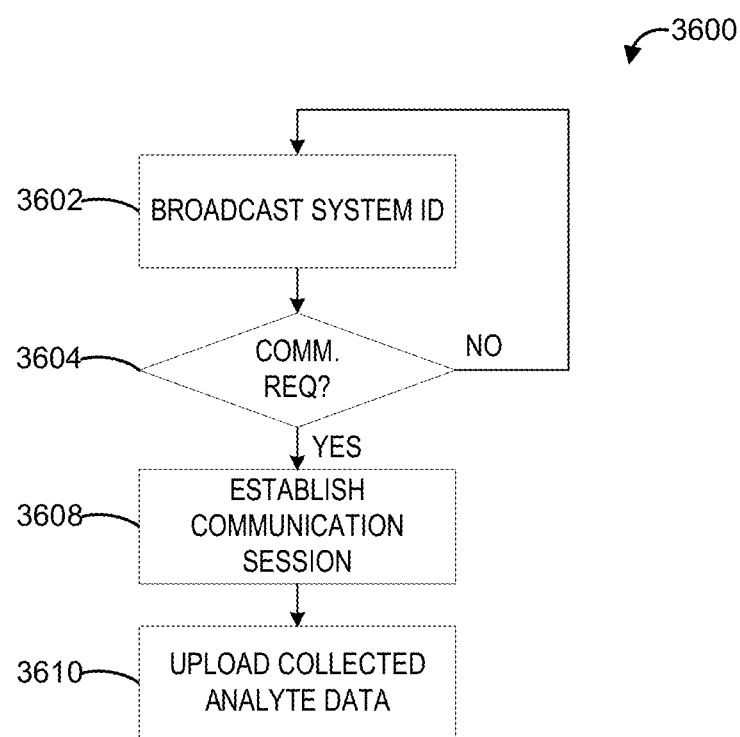
FIG. 36 is a flowchart showing one example of a process that can be executed by the sensor electronics to upload collected analyte data.

FIG. 36 is a flowchart showing one example of a process 3600 that can be executed by the sensor electronics 3406 to upload collected analyte data. The process 3600 is one example way that the sensor electronics 3406 can upload collected analyte data at step 3510 of the process 3500.

When the sensor use is over, in some examples, the analyte sensor device 3402 (or in some examples, just the sensor electronics 3406) are mailed or otherwise physically transported to a site where the upload device 3450 is present. In the example of FIG. 36, the sensor electronics 3406 begin broadcasting system identification data at step 3602. The system identification data can identify the sensor electronics 3406, the analyte sensor 3404 or both. The system identification data can be broadcast using any suitable wired or wireless communication technology including, for example, Bluetooth, Bluetooth LE, MICS, NFC, etc.

When the sensor electronics 3406 are within range of the upload device 3450, the upload device 3450 can receive the transmitted system identification data and use the system identification data to establish a communication link (e.g., a wireless communication link) with the sensor electronics. At operation 3604, the sensor electronics determines if it has received a request to establish a communications link, for example, with the upload device 3450. If no such request is received, the sensor electronics 3406 can continue to broadcast the system identification data at step 3602.

If a communication request is received at operation 3604, the sensor electronics 3406 establish a communication link, for example, with the upload device 3450 at step 3608. In some examples, establishing the communication link includes authenticating the upload device 3450. For example, the communication request from the upload device 3450 can include authentication data for authenticating the upload device 3450. The communication link can be according to any suitable wired or wireless technology including, for example, Bluetooth, Bluetooth LE, MICS, NFC, etc. Upon establishing the communication link, the sensor electronics 3406 can begin uploading collected analyte data to the upload device 3450 at operation 3610. The upload device 3450 may, in turn, upload the uploaded analyte data to one or more of the servers 3425, 3426, 3427 for further consideration. For example, the analyte data collected in this manner may constitute high-fidelity data that can be used, for example, in conjunction with low-fidelity data, as described herein.

Figure 37:
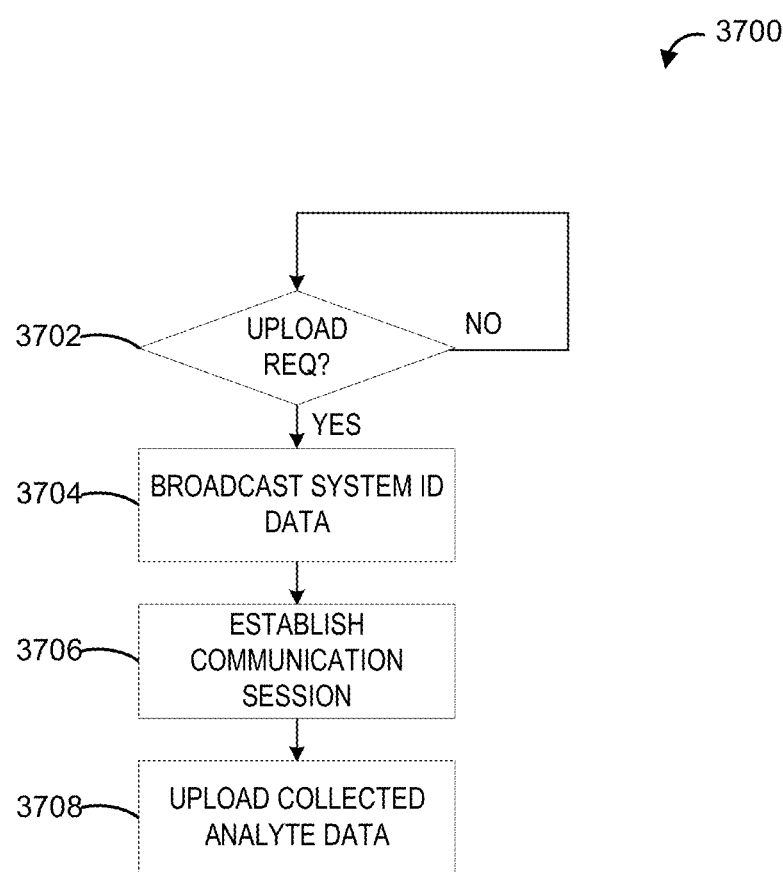
FIG. 37 is a flowchart showing another example of a process that can be executed by the sensor electronics to upload collected analyte data.

FIG. 37 is a flowchart showing another example of a process 3700 that can be executed by the sensor electronics 3406 to upload collected analyte data. The process 3700 is another example way that the sensor electronics 3406 can upload collected analyte data at step 3510 of the process 3500. As described herein, when sensor use is over, the analyte sensor device 3402 (or in some examples, just the sensor electronics 3406) are mailed or otherwise physically transported to a site where the upload device is present.

In the example of FIG. 37, when the sensor use is over, the sensor electronics 3406 determines, at 3702, whether it has received an upload request (e.g., from the upload device 3450). The upload request can be sent using any suitable wired or wireless communication protocol. In some examples, a wireless protocol such as NFC is used, although other protocols such as Bluetooth, Bluetooth LE, MICS, etc. can also be used. If no upload request is received, the sensor electronics 3406 continue waiting for an upload request at operation 3702.

If an upload request is received at operation 3702, the sensor electronics 3406 broadcasts system identification data at step 3704. At step 3704, the sensor electronics establishes a communication session with the upload device 3450 using the system identification data. For example, the upload device 3450 can receive the system identification data and retrieve authentication data for the sensor electronics 3406 using the system identification data. The upload device 3450 can use the authentication data to establish the communication session. When the communication session is established, the sensor electronics 3406 upload stored analyte data to the upload device 3450 at step 3708. The upload device 3450 may, in turn, upload the uploaded analyte data to one or more of the servers 3425, 3426, 3427 for further consideration. For example, the analyte data collected in this manner may constitute high-fidelity data that can be used, for example, in conjunction with low-fidelity data, as described herein.

While the methods and systems are often described herein in terms of estimated blood glucose concentration levels, such as levels determined by a CGM that estimates a blood glucose concentration level from a measurement of subcutaneous fluid, the methods and systems may also be applied to other types of concentration levels, such as actual blood glucose concentration level, or levels of other analytes in blood or other body fluids or substances. The methods and systems may also be applied to other physiologic states or conditions for which management is desirable for health or other reasons.

Each of these non-limiting examples can stand on its own or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method of monitoring a patient, comprising:
obtaining low-fidelity data of the patient using a low-fidelity monitoring technique over a first time period;
processing the low-fidelity data of the patient using a machine learning model to generate an output indicating whether the low-fidelity data indicates high-fidelity data collection is justified for the patient; and
responsive to the output indicating that high-fidelity data collection is justified for the patient, monitoring high-fidelity data of the patient using a high-fidelity monitoring technique over a second time period, wherein the high-fidelity monitoring technique comprises monitoring glucose data of the patient using a continuous glucose monitor device.

2. The method of claim 1, wherein the low-fidelity monitoring technique comprises at least one of single point glucose monitoring, blinded continuous glucose monitoring, or an optical monitoring technique.

3. The method of claim 1, wherein the low-fidelity monitoring technique comprises activity monitoring by a wearable fitness tracker.

4. The method of claim 3, wherein the wearable fitness tracker comprises at least one of a wearable heart rate monitor, activity monitor, smart phone, smart glasses, or smart watch.

5. The method of claim 1, wherein the low-fidelity monitoring technique comprises receiving user input data comprising at least one of medicament data, meal data, exercise data, or sleep data.

6. The method of claim 1, further comprising determining a goal for the patient based on the low-fidelity data.

7. The method of claim 6, wherein the goal includes a dietary goal, an exercise goal, a glucose level monitoring goal, or a medication goal.

8. The method of claim 6, wherein the determining the goal for the patient is based at least in part on the low-fidelity data obtained using the low-fidelity monitoring technique over the first time period.

9. The method of claim 1, further comprising providing a coaching functionality to the patient over the first time period, the coaching functionality comprising automated messages transmitted from a server to the continuous glucose monitor device, wherein the coaching functionality is based on at least one of patient profile data or the low-fidelity data of the patient.

10. The method of claim 1, wherein the machine learning model comprises a supervised learning model.

11. The method of claim 10, wherein the machine learning model is trained using labeled training data that includes sets of low-fidelity data and labels indicating whether each set of low-fidelity data justifies high-fidelity data collection.

12. The method of claim 1, wherein the machine learning model comprises an unsupervised learning model.

13. The method of claim 12, wherein the machine learning model is trained using unlabeled low-fidelity data.

14. The method of claim 1, wherein the machine learning model is a reinforcement learning model.

15. The method of claim 14, further comprising training the machine learning model by:
- obtaining low-fidelity data;
- generating a determination of whether the low-fidelity data justifies high-fidelity data collection; and
- obtaining feedback indicating whether the determination is correct.

16. A system comprising:
- a low-fidelity system configured to collect low-fidelity data relating to a patient over a first time period;
- a machine learning model configured to receive the low-fidelity data of the patient and generate an output indicating whether the low-fidelity data indicates high-fidelity data collection is justified for the patient; and
- a continuous glucose monitor device configured to collect high-fidelity data relating to the patient responsive to the output indicating that high-fidelity data collection is justified for the patient.

17. The system of claim 16, wherein low-fidelity system includes an activity sensor.

18. The system of claim 16, wherein low-fidelity system includes a blood glucose meter.

19. The system of claim 16, wherein the continuous glucose monitor device includes a continuous glucose monitor.

20. A machine-readable medium comprising instructions thereon that, when executed by at least one processor, cause the at least one processor to perform operations comprising:
- obtaining low-fidelity data of a patient using a low-fidelity monitoring technique over a first time period;
- processing the low-fidelity data of the patient using a machine learning model to generate an output indicating whether the low-fidelity data indicates high-fidelity data collection is justified for the patient; and
- responsive to the output indicating that high-fidelity data collection is justified for the patient, monitoring high-fidelity data of the patient using a high-fidelity monitoring technique over a second time period, wherein the high-fidelity monitoring technique comprises monitoring glucose data of the patient using a continuous glucose monitor device.

* * * * *